(12) United States Patent
Tipgunlakant et al.

(10) Patent No.: US 9,994,889 B2
(45) Date of Patent: Jun. 12, 2018

(54) ADVANCED MICROPLATE, MICROTITER, AND MICROARRAY TECHNOLOGIES WITH PER-WELL FLUIDICS, GAS EXCHANGE, ELECTRONIC SENSORS, AND IMAGING FOR CELL CULTURE AND OTHER APPLICATIONS

(71) Applicants: Pooncharas Tipgunlakant, San Francisco, CA (US); Lester F. Ludwig, San Antonio, TX (US)

(72) Inventors: Pooncharas Tipgunlakant, San Francisco, CA (US); Lester F. Ludwig, San Antonio, TX (US)

(73) Assignee: NRI R&D PATENT LICENSING, LLC, San Antonio, TX (US)

( * ) Notice: Subject to any disclaimer, the term of this patent is extended or adjusted under 35 U.S.C. 154(b) by 0 days. days.

(21) Appl. No.: 13/844,621

(22) Filed: Mar. 15, 2013

(65) Prior Publication Data

US 2014/0273191 A1    Sep. 18, 2014

(51) Int. Cl.
*C12Q 1/02*    (2006.01)
*C12M 1/34*    (2006.01)
(Continued)

(52) U.S. Cl.
CPC ........ *C12Q 1/025* (2013.01); *B01L 3/502715* (2013.01); *C12M 23/12* (2013.01);
(Continued)

(58) Field of Classification Search
CPC ...... C12Q 1/025; C12Q 1/02; G01N 35/1074; G01N 15/06; G01N 15/0656;
(Continued)

(56) References Cited

U.S. PATENT DOCUMENTS

2003/0049862 A1\* 3/2003 He .................. B01L 3/5025
506/16
2003/0190608 A1\* 10/2003 Blackburn ........... B01J 19/0093
435/6.11

(Continued)

*Primary Examiner* — Michael L Hobbs
(74) *Attorney, Agent, or Firm* — Procopio, Cory, Hargreaves & Savitch LLP

(57) ABSTRACT

Arrangements for per-well fluidics, gas exchange, and electronic sensors for microplate, microtiter, and microarray technologies are presented. In example implementations, each individual well within in a conventional or specialized microplate can be fully or partially isolated with capping or other arrangements which can include conduits for controlled introduction, removal, and/or exchange of fluids and/or gases. Conduit networks can include small controllable valves that operate under software control, and microscale pumps can also be included. Conduit interconnections can include one or more of controllable-valve distribution buses, next-neighbor interconnections, and other active or passive interconnection topologies. Cap arrangements can include or provide one or more sensors of various types, including but not limited to selective gas sensors, chemical sensors, temperature sensors, pH sensors, biosensors, immunosensors, molecular-imprint sensors, optical sensors, fluorescence sensors, bioFETS, etc. Incubator interfacing and imaging are also described. The invention can be used for living cell culture or other applications.

24 Claims, 51 Drawing Sheets

(51) Int. Cl.
  *G01N 15/06* (2006.01)
  *G01N 33/50* (2006.01)
  *B01L 3/00* (2006.01)
  *C12M 1/32* (2006.01)
  *C12M 3/06* (2006.01)

(52) U.S. Cl.
  CPC ............. *C12M 23/16* (2013.01); *C12Q 1/02* (2013.01); *G01N 15/06* (2013.01); *G01N 15/0656* (2013.01); *G01N 33/5017* (2013.01); *B01L 3/5025* (2013.01); *B01L 2300/046* (2013.01); *B01L 2300/047* (2013.01); *B01L 2300/049* (2013.01); *B01L 2300/0645* (2013.01); *B01L 2300/0654* (2013.01); *B01L 2300/0829* (2013.01); *B01L 2300/10* (2013.01); *B01L 2300/1822* (2013.01); *B01L 2300/1827* (2013.01); *B01L 2400/0487* (2013.01); *G01N 2015/0681* (2013.01); *G01N 2015/0693* (2013.01)

(58) Field of Classification Search
  CPC ....... G01N 33/5017; G01N 2015/0681; G01N 2015/0693; C12C 1/025; C12C 1/02; B01L 3/502715; B01L 3/5025; B01L 2300/046; B01L 2300/47; B01L 2300/049; B01L 2300/0645; B01L 2300/0654; B01L 2300/0829; B01L 2300/10; B01L 2300/1822; B01L 2300/1827; B01L 2400/0487; C12M 23/12; C12M 23/16
  USPC .......................................... 435/288.4; 506/43
  See application file for complete search history.

(56) References Cited

U.S. PATENT DOCUMENTS

| | | | |
|---|---|---|---|
| 2005/0266582 A1* | 12/2005 | Modlin | B01L 3/502723 436/164 |
| 2007/0020689 A1* | 1/2007 | Caracci | G01N 35/028 435/287.2 |
| 2007/0237685 A1* | 10/2007 | Bergman | B01L 3/5025 422/400 |
| 2008/0261220 A1* | 10/2008 | Cracauer et al. | 435/6 |
| 2009/0197277 A1* | 8/2009 | Beard et al. | 435/6 |

* cited by examiner

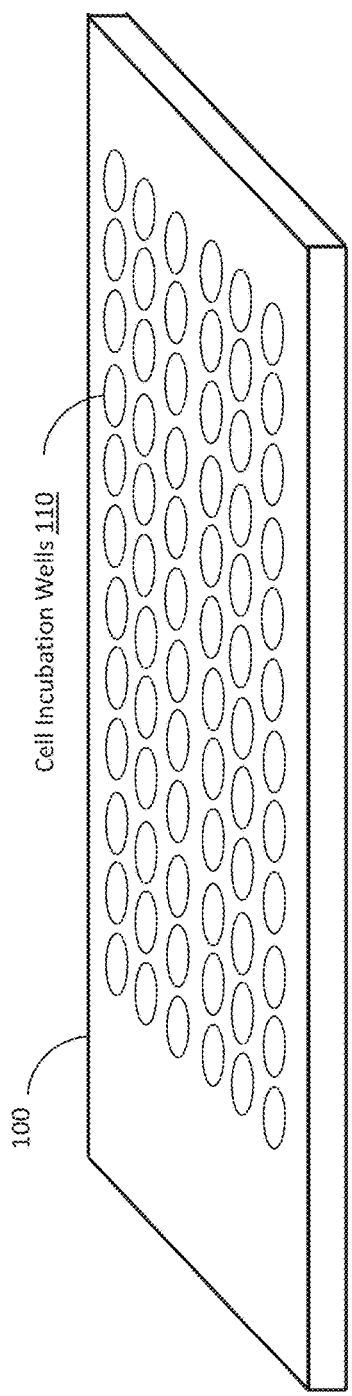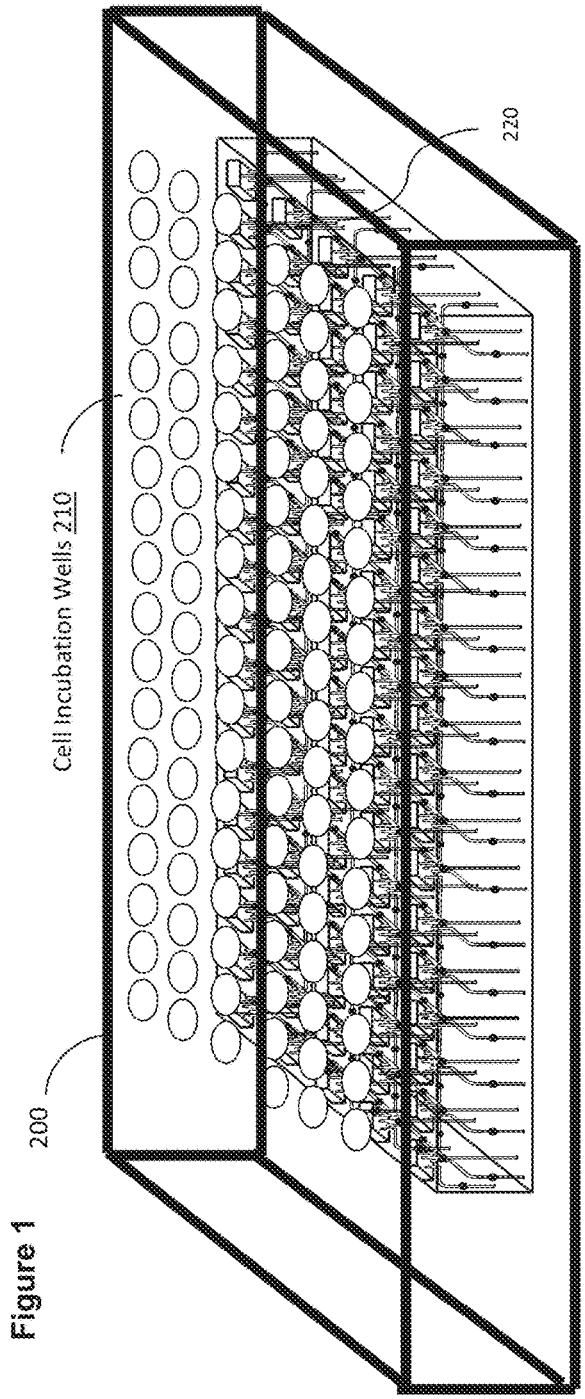

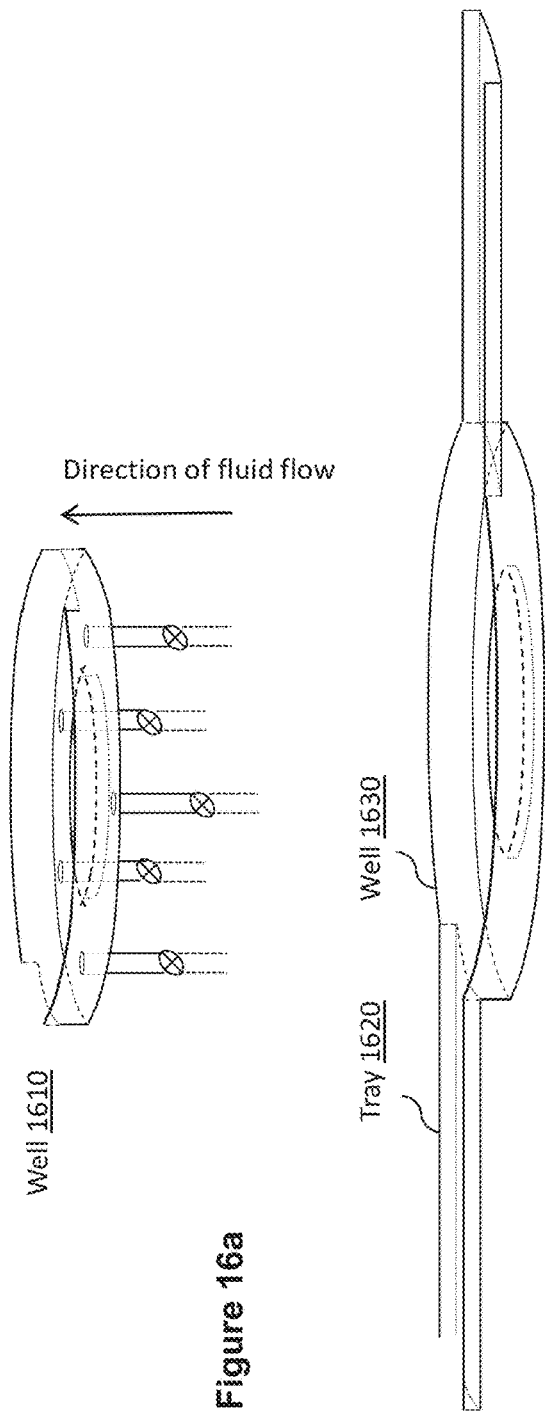
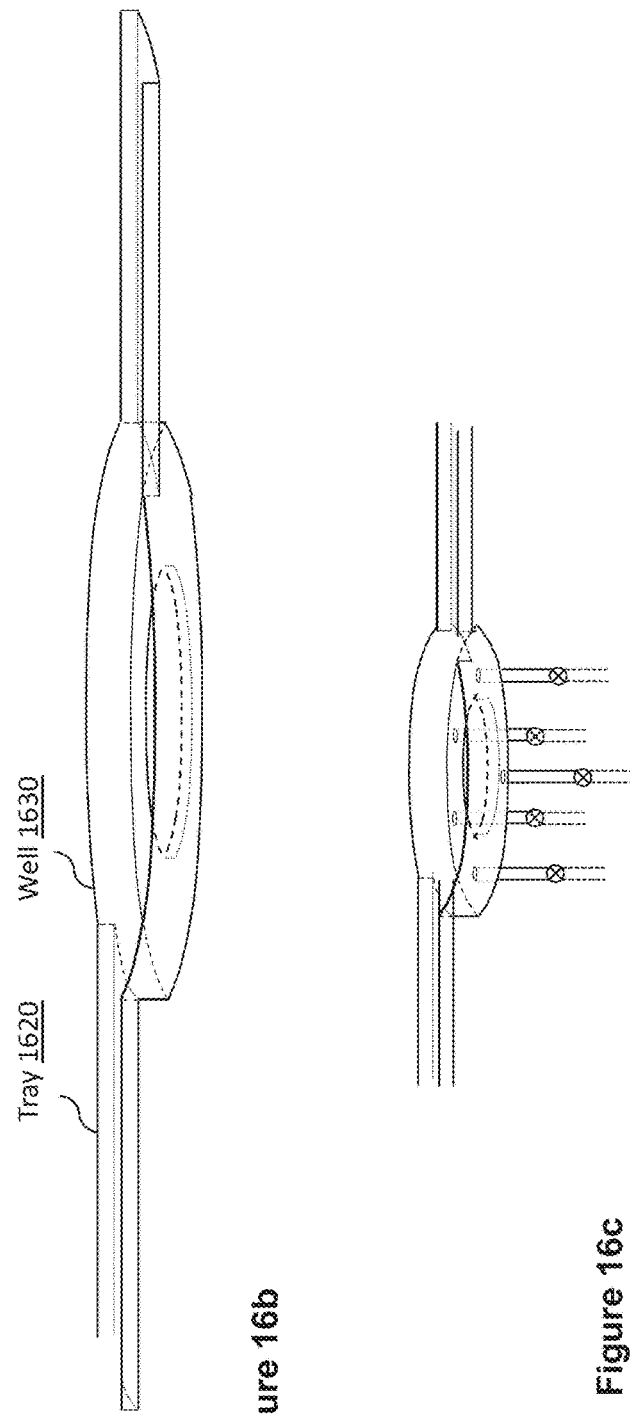
Figure 16a — Well 1610, Direction of fluid flow
Figure 16b — Tray 1620, Well 1630
Figure 16c

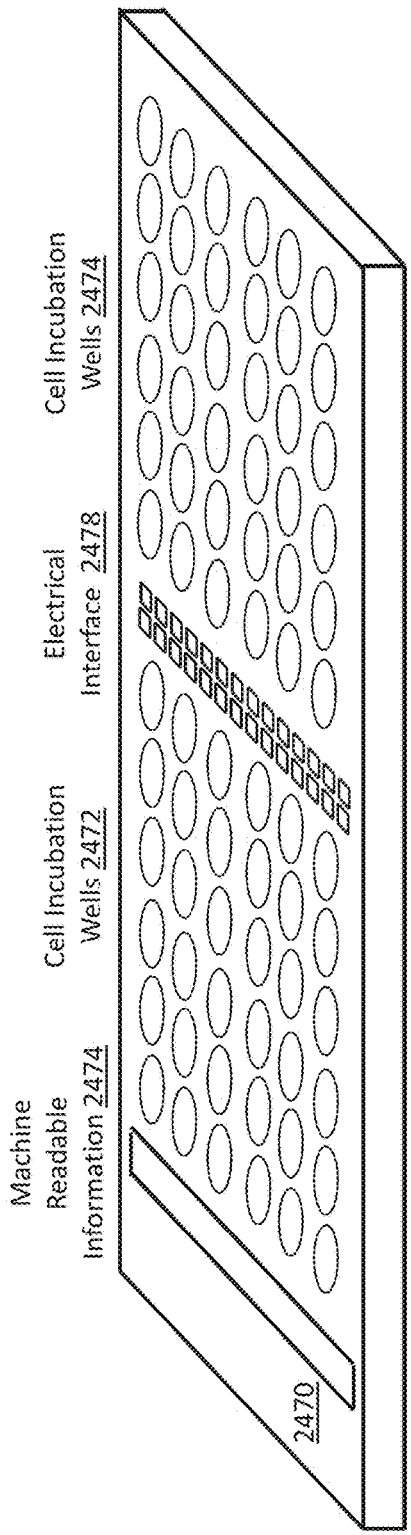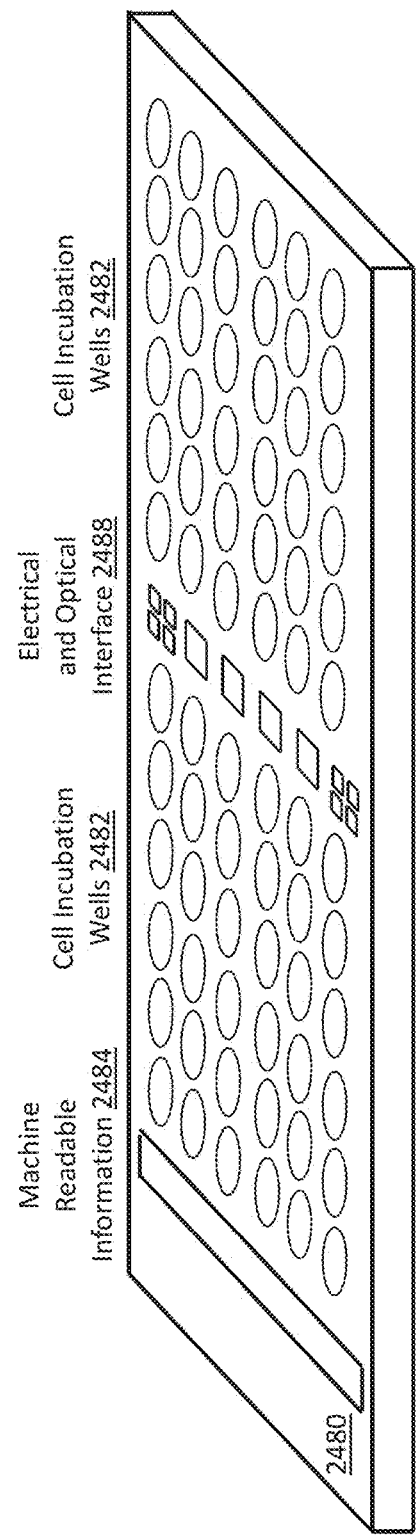
Figure 24c
Figure 24d

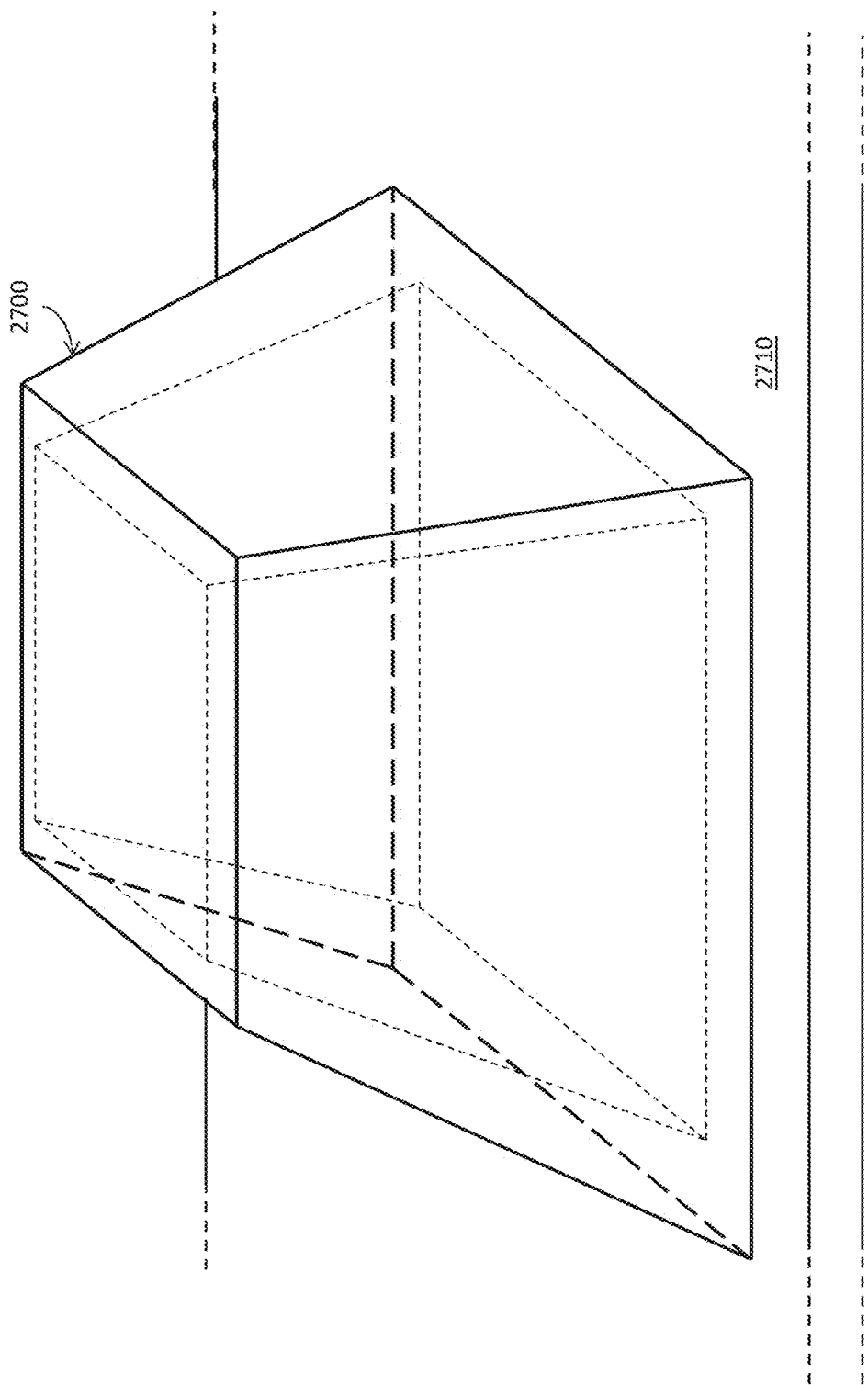

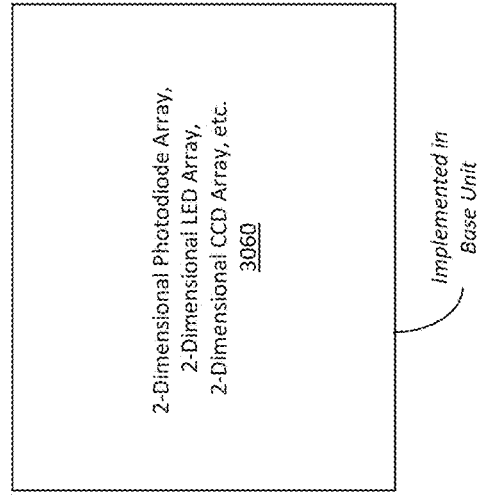
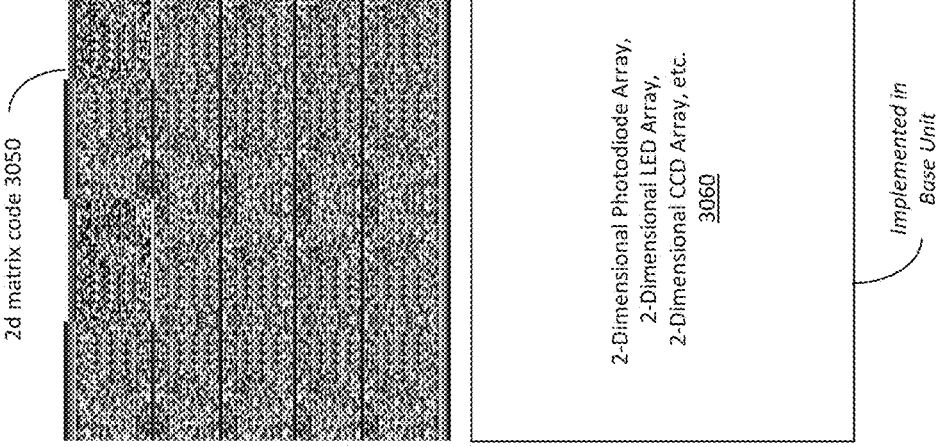
Figure 30c
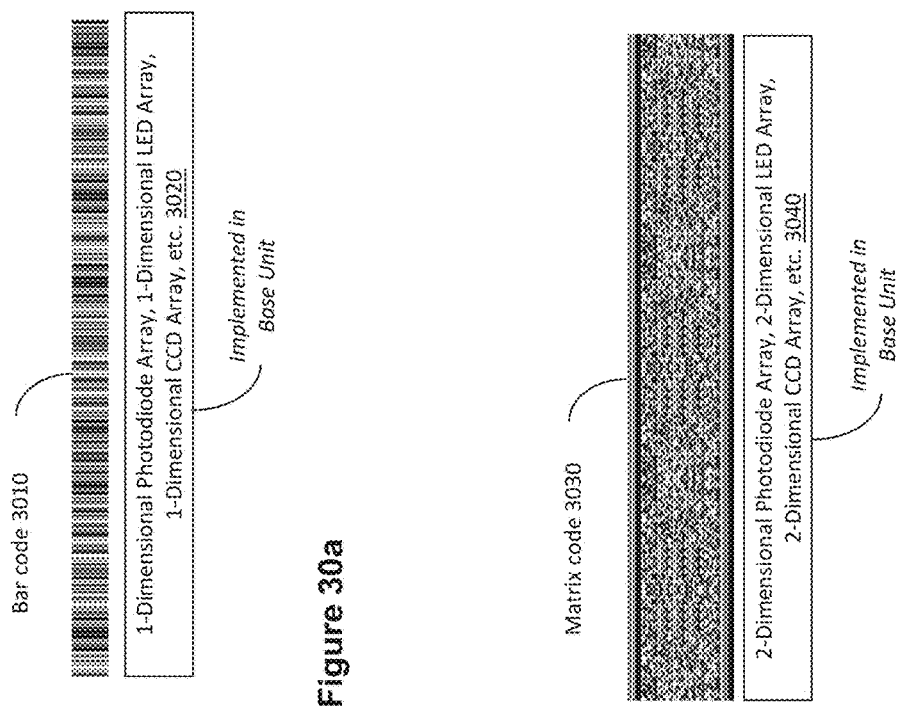
Figure 30a
Figure 30b

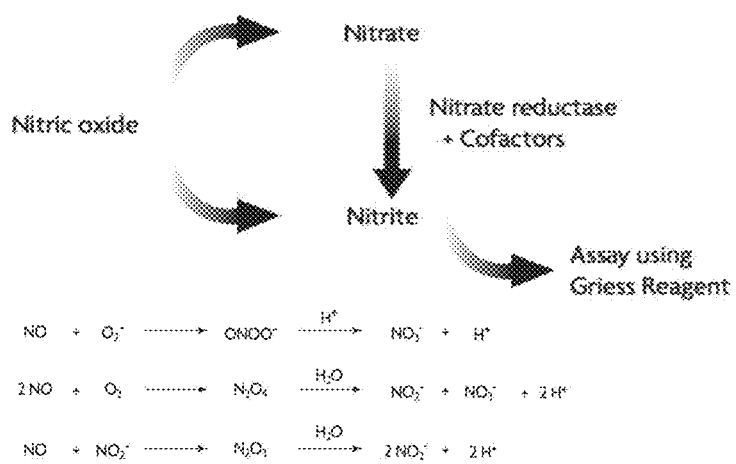
Figure 41 Principle of NO quantitative kit.
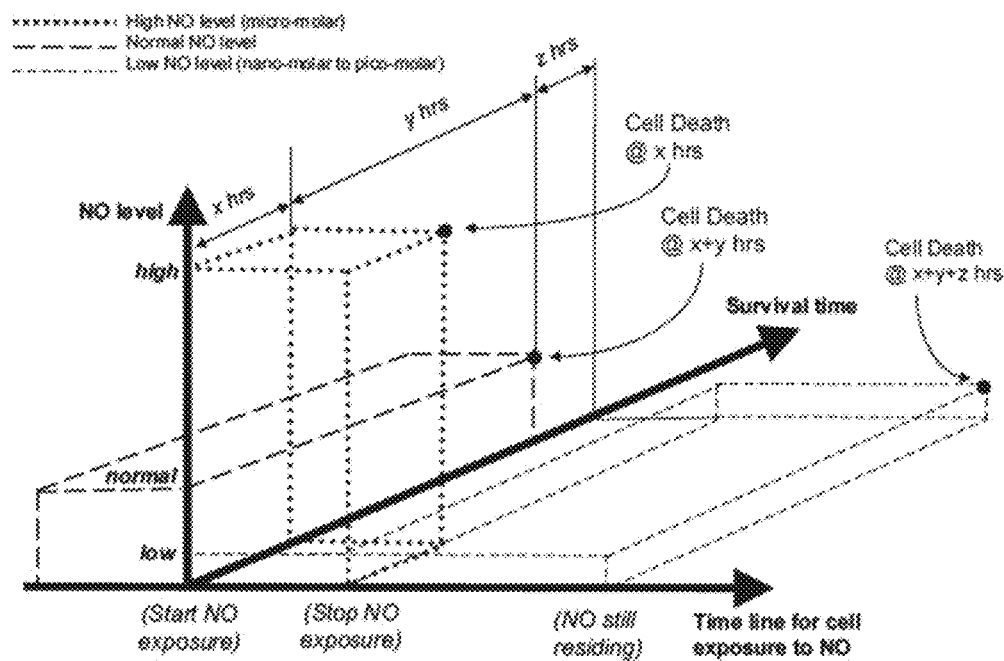
Figure 42a

ADVANCED MICROPLATE, MICROTITER, AND MICROARRAY TECHNOLOGIES WITH PER-WELL FLUIDICS, GAS EXCHANGE, ELECTRONIC SENSORS, AND IMAGING FOR CELL CULTURE AND OTHER APPLICATIONS

COPYRIGHT & TRADEMARK NOTICES

A portion of the disclosure of this patent document may contain material, which is subject to copyright protection. Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

BACKGROUND OF THE DISCLOSURE

Field

Embodiments of the application pertain generally to cell incubators, microarrays, microfluidic systems, and miniature biochemical and chemical detectors, and more specifically to microprocessor-controlled microfluidic platform technologies comprising such miniature biochemical and chemical detectors configured as instrumented cell incubators for providing a plurality of simultaneous distinct controlled micro-environments for living cell cultures.

General Background

Culturing cells, such as tissue cells, cancer cells, bacteria, yeasts, molds, plankton, infectious protozoa, etc. as well as cell-related materials such as infectious viruses and prions in the laboratory typically require managed, and often precisely managed, environmental control. In the laboratory, cell incubators are the most common and essential equipment for nurturing and maintaining living cells.

Cell incubators typically provide several environment-providing functions that often must meet or operate within numerous rigid specifications relating to temperature, humidification, gaseous environment, sterilization, and specimen safety. Additionally these conditions are not uniform across cell types. For example, culturing mammalian cells and bacteria require the temperature at 37° C., 5% carbon dioxide, and 95% humidity and sterilized condition. However, other cell types, for instance the budding yeast *Saccharomyces cerevisiae* grows at a temperature at 30° C.

Contemporary cell incubator technologies can provide computer controlled thermal regulation, humidified control, control of gas levels such as $CO_2$, $O_2$, and $N_2$, and illumination of cell cultures contained in open (or in some cases closed) dishes and welled microplates. In addition, many contemporary cell incubators can be programmed to control environmental factors through a sequence or cycle of distinct temperatures, humidity levels, etc.

In vitro study can involve study of biochemical process or pharmacodynamical substances provided to cultured cells. Examples include adding pharmaceuticals and changing aspects of the culture medium. In order to enact these, the sample must typically be removed and translocated to outside the incubator, thus discontinuing or disrupting the controlled cell nurturing condition. In contrast to in vitro study, in vivo study provides a consistent biological environment for observing biological responses from the effects of medical treatment. Uninterrupted controlling of the conditional environment while studying cellular responses can minimize the introduction of corrupting processes and far more precisely mimic the actual biological environment of the body of a higher organism or other natural cellular environment.

In addition, the required and optimal conditions of the biological environment for various cell types are often different, especially in regards to the proportion of ambient gases such as carbon dioxide ($CO_2$), oxygen ($O_2$) and nitrogen ($N_2$). For example, cells within a solid tumor malignancy are in hypoxia (low oxygen), yet normal cell is in normoxia (normal oxygen). Additionally, hypoxia conditions play an important role in gene expression related to cellular signal transduction. Therefore, to study the cellular responses at the desired cell culture conditions—hypoxia and normoxia, control of the proportion of gases during cell incubating is considered.

To study effects of substance concentrations on the biological responses, monitoring levels of the interested substances are concerned. For example, different concentrations of nitric oxide (NO) are relevant to cell signaling and cell apoptosis, measuring concentration of nitric oxide at steady states is required during cell culture. In some cases, substances of interest are produced naturally by biological process, while in other types of experiments, substances of interest are introduced artificially.

Further, it is noted for example that due to its highly reactive nature, artificially provided NO typically must be introduced very locally to NO affectation/consumption regions by controlled introduction of NO-donor compounds. Other types of substance concentration experiments can require highly localized substance measurement (for example by means of substance-responsive fluorescent markers) and/or highly localized substance introduction (for example by means of substance-generative donors)

To study the pharmacological and biochemical effects via in vitro study, observing cell responses from within incubation—i.e., without removal and interruption of the period of environmental control, would be expected to provide higher accuracy and diminish corruption opportunities. However, current methods for determining the effects of the substances on the cells involve waiting until cells are stable in the cell culture medium and environment and subsequently performing an operation outside the environmental control provided by the incubator. Even though efforts can be taken to minimize analysis time outside the incubator can reduce corruptive effects, often cells are still very sensitive to changes of environment. In addition, other aspects of cell response study can be affected and made more complicated. Therefore, processes such as treating the cells with substances and analyzing the cell responses against monitored desirable conditions, and operations of processes within the control condition in the incubator have become a formidable challenge for in vitro studies.

BRIEF DESCRIPTION OF THE DRAWINGS

The above and other aspects, and features of the present application will become more apparent upon consideration of the following description of embodiments taken in conjunction with the accompanying drawing figures, wherein:

FIG. 1 depicts a representation of an example microplate comprising cell incubation wells.

FIG. 2 depicts example fluidics arrangements included within a microplate.

FIG. 10b depicts a representation of an example separate self-contained cap and associated fluidic/gas-tight seal that can be placed against the open portion of the microplate well depicted in FIG. 10a.

FIG. 16a depicts an example arrangement wherein fluids can be introduced from below the cell wells.

FIG. 16b depicts an example arrangement wherein fluids can be transported in and out of individual cell culture wells by surface-exposed trays.

FIG. 16c depicts an example arrangement involving a combination of the approaches of FIGS. 16a and 16b.

FIGS. 24a-24d depict example representations of the removable replaceable media element according to some embodiments.

FIG. 27a depicts a cap interfacing with a site on the removable replaceable media element according to some embodiments.

FIGS. 30a-30c depict examples of how optical ROM printed on the removable replaceable media can be read by the base system according to some embodiments.

FIG. 41 depicts the principle of operation of an example NO quantitative kit.

FIG. 42a depicts a summarization of the relationship between NO exposure concentration and duration (control variables in the experiment) and cell survival time.

DETAILED DESCRIPTION

Figure 3:
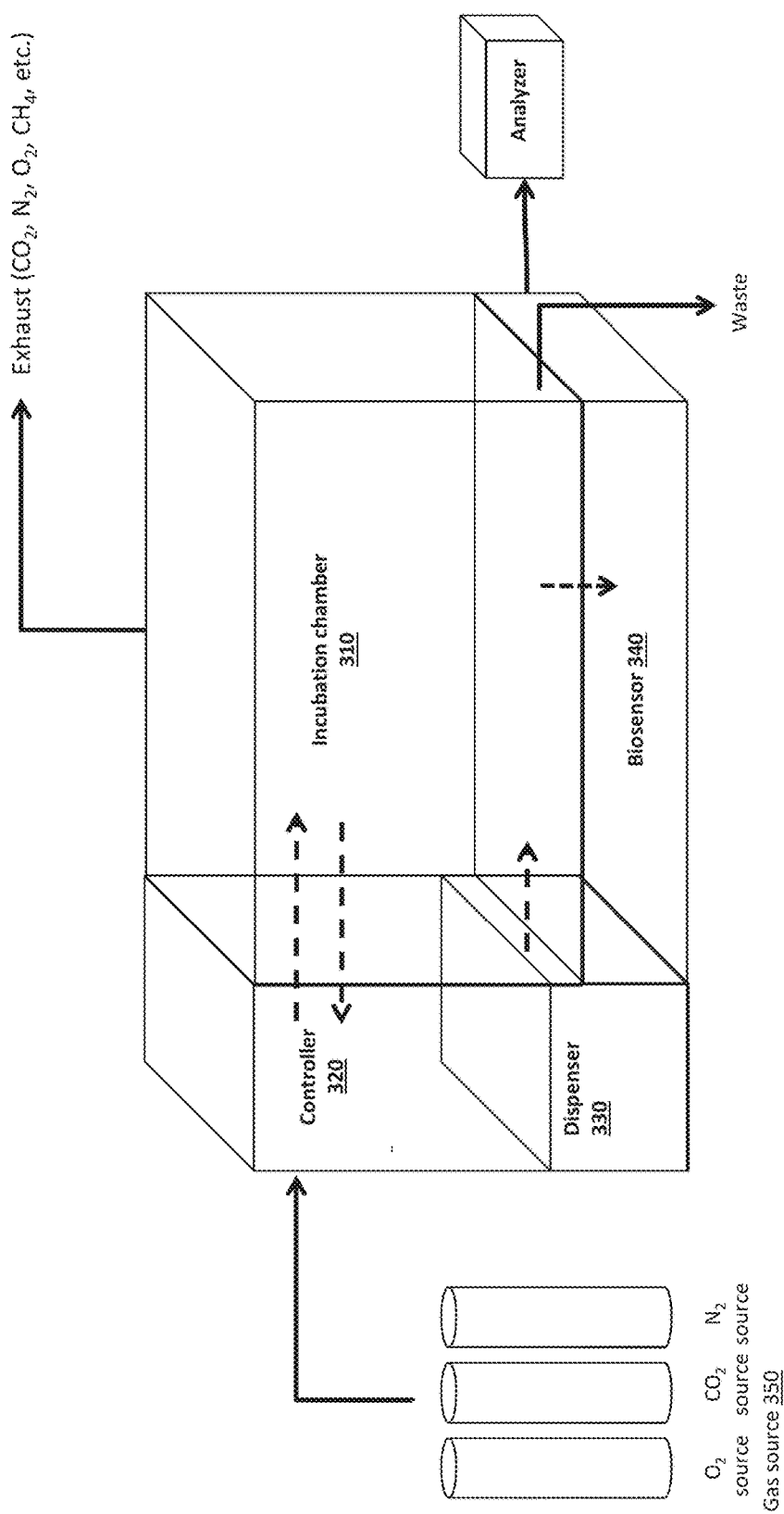
FIG. 3 depicts an incubation system according to some embodiments.

In the following description, reference is made to the accompanying drawing figures which form a part hereof, and which show by way of illustration specific embodiments of the present application. It is to be understood by those of ordinary skill in this technological field that other embodiments may be utilized, and structural, electrical, as well as procedural changes may be made without departing from the scope of the present application.

In the following description, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

Various embodiments provide for various synergistic combinations of the following features:
  Dedicated localized sensors associated with individual wells of replaceable removable media
    In replaceable removable media well
    In associated cap sealing the top of replaceable removable media well
    Distributed among well and cap
  Dedicated localized fluidics associated with individual wells of replaceable removable media
    In replaceable removable media well
    In associated cap sealing the top of replaceable removable media well
    Distributed among well and cap
  Shared gas exchange for a group of individual wells of replaceable removable media
  Dedicated localized gas exchange associated with individual wells of replaceable removable media
    In replaceable removable media well
    In associated cap sealing the top of replaceable removable media well
    Distributed among well and cap
  Shared thermal control for a group of individual wells of replaceable removable media
  Dedicated localized thermal control associated with individual wells of replaceable removable media
    In replaceable removable media well
    In associated cap sealing the top of replaceable removable media well
    Distributed among well and cap
  Shared imaging for a group of individual wells of replaceable removable media
  Dedicated localized imaging associated with individual wells of replaceable removable media
    In replaceable removable media well
    In associated cap sealing the top of replaceable removable media well
    Distributed among well and cap.
  Shared illumination for a group of individual wells of replaceable removable media (with some embodiments providing a selectable range or combination of illumination wavelengths in the visible and/or U.V. range)
  Dedicated localized illumination associated with individual wells of replaceable removable media (with some embodiments providing a selectable range or combination of illumination wavelengths in the visible and/or U.V. range)
    In replaceable removable media well
    In associated cap sealing the top of replaceable removable media well
    Distributed among well and cap.

These arrangements provide for various degrees of individually controlled, monitored, and isolated cell incubation chambers by leveraging computer-executed algorithms and computer-interfacing hardware for providing computer monitoring and computer control.

Additionally various embodiments employ several component core, design, and fabrication technologies including one or more of:
  One or more arrays of individual incubator chambers, each comprising microfluidic and biosensor aspects.
  Microplates and associated fluidic structures can be fabricated employing function printing, 3D printing, and/or digital printing.
  Printed electronic sensors or sensor components associated with individual chambers, for example employing one or more of printed organic semiconducting and printed conducting polymers,
  Optical sensors or sensor components associated with individual chambers employing one or more of printed antibodies, printed optical materials, printed organic semiconducting, printed conducting polymers, Printed mechanical structures associated with individual chambers, FIG. 1 depicts a representation of an example microplate 100 comprising cell incubation wells 110. Such microplates 100 are commonly used for a variety of purposes and often are used to contain arrays of materials such as biological substances and cell cultures. Typically such microplates are passive tray-like structures similar in many ways to kitchen refrigerator ice trays. The wells 110 are spatially isolated for one another and accordingly can be used to contain individual segregated cell cultures. Further, the cell cultures can be provided with colorimetric indicators or fluorescent markers whose optical absorption and emission properties are responsive to biological molecules or conditions.

In some embodiments, microplate 100 can be provided with additional enhanced features, for example:

Miniature electrical biosensors (electrochemical, bioFET, etc.) comprised within wells 110 of the microplate 100;

Miniature optical biosensors comprised in whole or in part within wells 110 of the microplate 100 or otherwise associated with wells 110 of the microplate 100;

Passive (flow passages) fluidics integrated into the microplate 100 and directly connected to wells 110 of the microplate 100, as discussed further with reference to in FIG. 2;

Active (valves, pumps, electro-osmosis, electro-wetting, etc.) fluidics integrated into the microplate 100, and in some cases directly connected to wells 110 of the microplate 100.

As to miniature biosensors, a wide range of suitable miniature electrical biosensors and miniature optical biosensors are taught in pending U.S. patent application Ser. No. 13/761,142. These can be fabricated by functional printing for example as taught in pending U.S. patent application Ser. No. 13/761,142 and as will be explained.

As to fluidics, fluidics arrangements can be included within a microplate 200, for example as suggested by the arrangement depicted in FIG. 2. Microplate 100 comprising intricate fluidic structures 220 that can be fabricated, e.g., by employing function printing, 3D printing, and/or digital printing methods. As illustrated in FIG. 2, fluidic structures 220 are directly connected to wells 210 of microplate 200. Various approaches to removable controlled fluidics systems and methods are taught in pending U.S. patent application Ser. No. 13/761,142 and the co-filed U.S. Patent Application entitled "Removable Fluidics Structures for Microarray, Microplates, Sensor Arrays, and other Removable Media."

In some embodiments, fluidics arrangements 220 within a microplate 200 can be included and configured to provide individual wells 210 in the microplate 200 a controlled fluidic commonly or individually dispensed delivery of nutrients. In some embodiments, fluidics arrangements 220 within a microplate 200 can be included and configured to provide individual wells 210 in the microplate 200 a controlled fluidic commonly or individually dispensed delivery of dissolved gases. In some embodiments, fluidics 220 can also be configured to provide regulated local thermal control, and can be configured to commonly or individually dispense protective materials to prevent or fight unintended infections from various phages, pathogens, parasites, and competing intruder cell types. The fluidics 220 can also be used to commonly or individually introduce materials to be exposed to the cells, for example drugs, pharmaceutical agents, photosensitizers, fluorophore probes/markers, etc. into individual wells 210. Additionally, fluidics 220 in the microplate 200 can provide controlled fluidic removal of waste materials so as to support life processes of one or more cells in an adapted and/or modified cap and site arrangement.

FIG. 3 depicts an incubator system 300 for providing computer controlled thermal regulation, humidity control, and control of gas levels (such as $CO_2$, $O_2$, and $N_2$) for cell cultures contained in an open welled microplate, the microplate fitted, for example, with biosensors and/or microfluidics.

Incubator system 300 comprises an incubation chamber 310 for receiving one or more microplates and for providing a common atmospheric chamber presented to open wells of cell culture, a dispenser 330 for dispensing cell culture media/reagent, biosensor 340, a gas input source 350 and a controller 320 to provide one or more of the following control features:

For the entire set of wells of a microplate:
  Gas handling, as discussed further with reference to FIGS. 4A and 4B;
  Controlled illumination of cells, for example to photo-active specific materials, for imaging, for colorimetric or fluorimetric measurement, photosynthesis, etc.;
  Programmed control of one or more environmental factors (temperature, humidity, gas environment, etc.) through a sequence or cycle of distinct temperatures, humidity levels, etc.; and
  Imaging capabilities.

In some embodiments, individual wells within a microplate comprise one or more of:
  A. Miniature electrical biosensors (electrochemical, bioFET, etc.) comprised within wells of the microplate;
  B. Miniature optical biosensors comprised in whole or in part within wells of the microplate or otherwise associated with wells of the microplate;
  C. Passive (flow passages) fluidics integrated into the microplate;
  D. Active (valves, pumps, electroosmosis, electrowetting, etc.) fluidics integrated into the microplate.

Figure 4A:
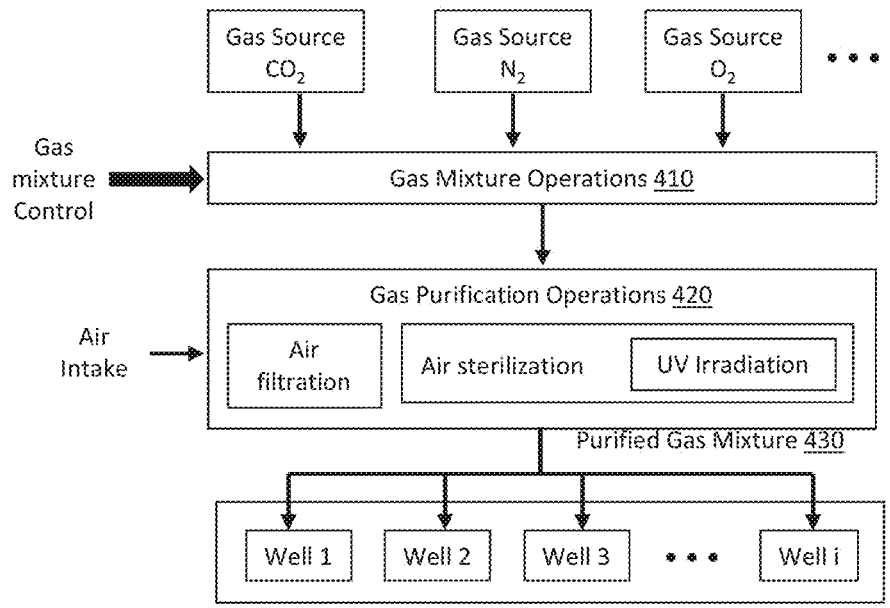
FIG. 4a depicts an example arrangement suitable for providing a common gas environment to all cell cultures in an incubator system.

In some embodiments, incubator system 300 provides gas handling for the entire group of wells of a microplate. FIG. 4a depicts an example arrangement suitable for providing a common gas environment to all cell cultures in the incubator.

In this example, gases are fixed mixed 410 under computer control (e.g., control by controller 320) and then purified 420 (for example operations involving filtration and sterilization by U.V. light). The resulting purified gas mixture 430 can then be provided to a common atmospheric chamber presented to open wells or dishes of cell culture, such as incubation chamber of FIG. 3. Thus FIG. 4a depicts an example arrangement suitable for providing a common gas environment to all cell cultures in an incubator wherein gases are first fixed mixed under computer control, then purified (for example involve options involving filtration and sterilization by U.V. light), and provided to a common atmospheric chamber presented to open wells or dishes of cell culture, for example in particular to embodiments such as that of earlier FIG. 3.

Figure 4B:
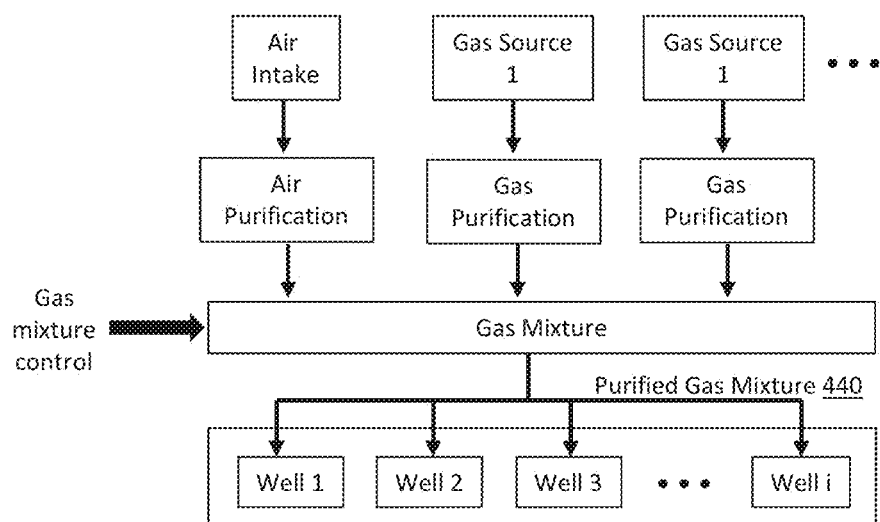
FIG. 4b depicts an example arrangement suitable for providing a common gas environment to all cell cultures in an incubator system.

Alternatively, FIG. 4b depicts an example variation on the arrangement of FIG. 4a wherein each gas is separately purified first prior to mixing before a resultant purified gas mixture 440 is provided to a common atmospheric chamber presented to open wells or dishes of cell culture, such as incubation chamber of FIG. 3.

Figure 5:
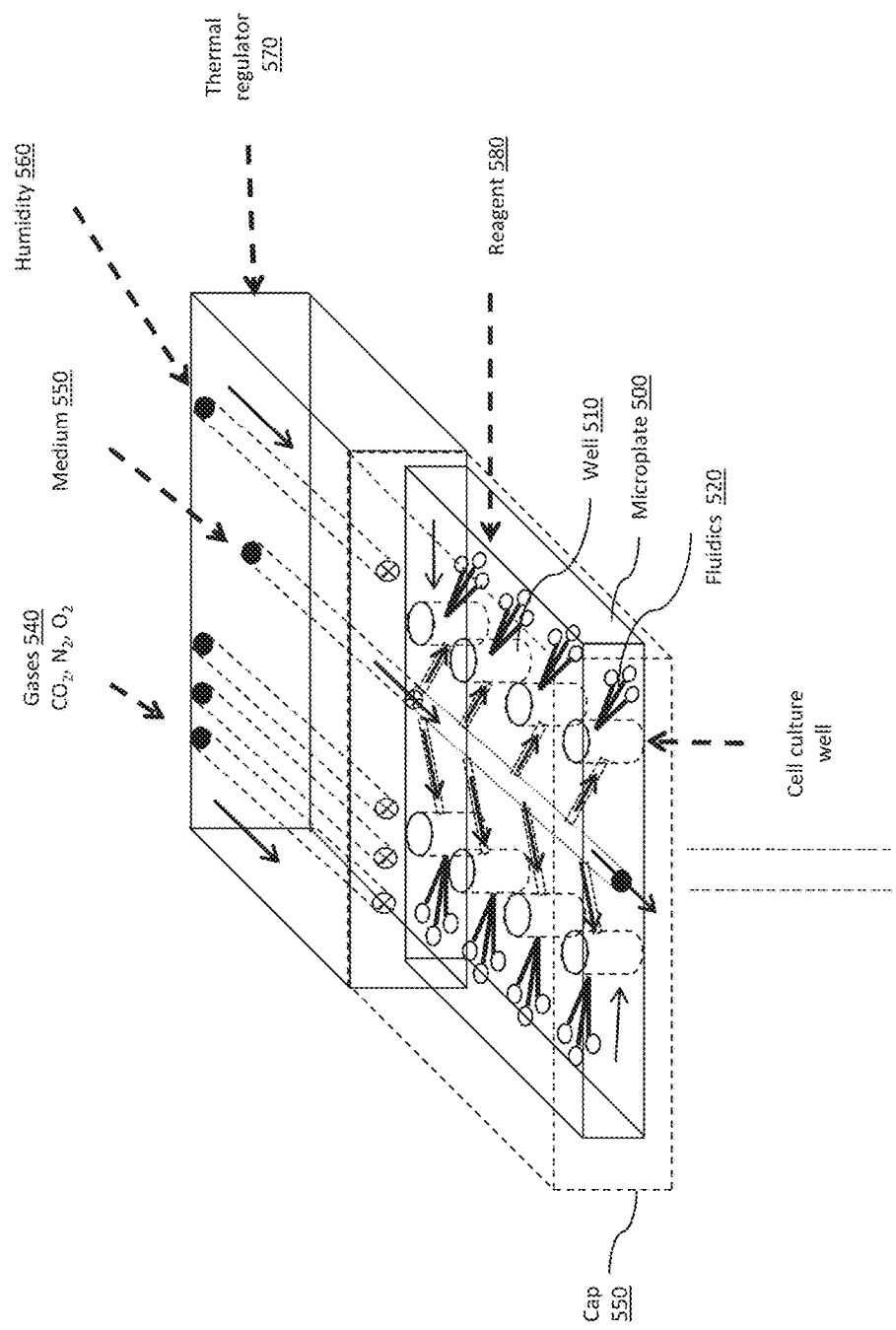
FIG. 5 depicts an example arrangement wherein a microplate including fluidics arrangements.

FIG. 5 depicts an example a microplate 500 including wells 510 with fluidics arrangements 520. Also illustrated is a microplate cap 505, e.g., which may be used to compartmentalize a microplate from other microplates within incubator system. In some embodiments, microplate 500 operates within a common gas, temperature, humidity, illumination, and imaging environment provided by an incubator, such as incubator system 300. Incubator system (e.g., incubator system 300) provides gas input 540, cell medium 550 and humidity 560 and controls a thermal input 570 to microplate 500. Microplate 500 may receive plate-specific gas and media flows and temperature regulation. A dispenser (e.g., dispenser 330) dispenses cell culture media/reagent 580.

In some embodiments, the arrangement depicted in FIG. 5 can be configured to provide microscopic imaging, for example, by employing a movable microscopic imaging camera. In an embodiment, wells fitted with sensors and/or fluidics in a microplate can be configured to have a transparent region in the well base that can be illuminated from below. In some embodiments, the entire collection of wells is simultaneously illuminated. In other embodiments, each well (or small group of wells) is individually illuminated. In some embodiments, the imaging lens or lens system together with imaging camera can be moved in order to image one or more selected wells. In other embodiments, the entire collection of wells are simultaneously illuminated and a plurality of imaging lens or lens systems together with imaging camera are arranged in fixed locations dedicated to the microscopic imaging of one or more selected wells.

Figure 6A:
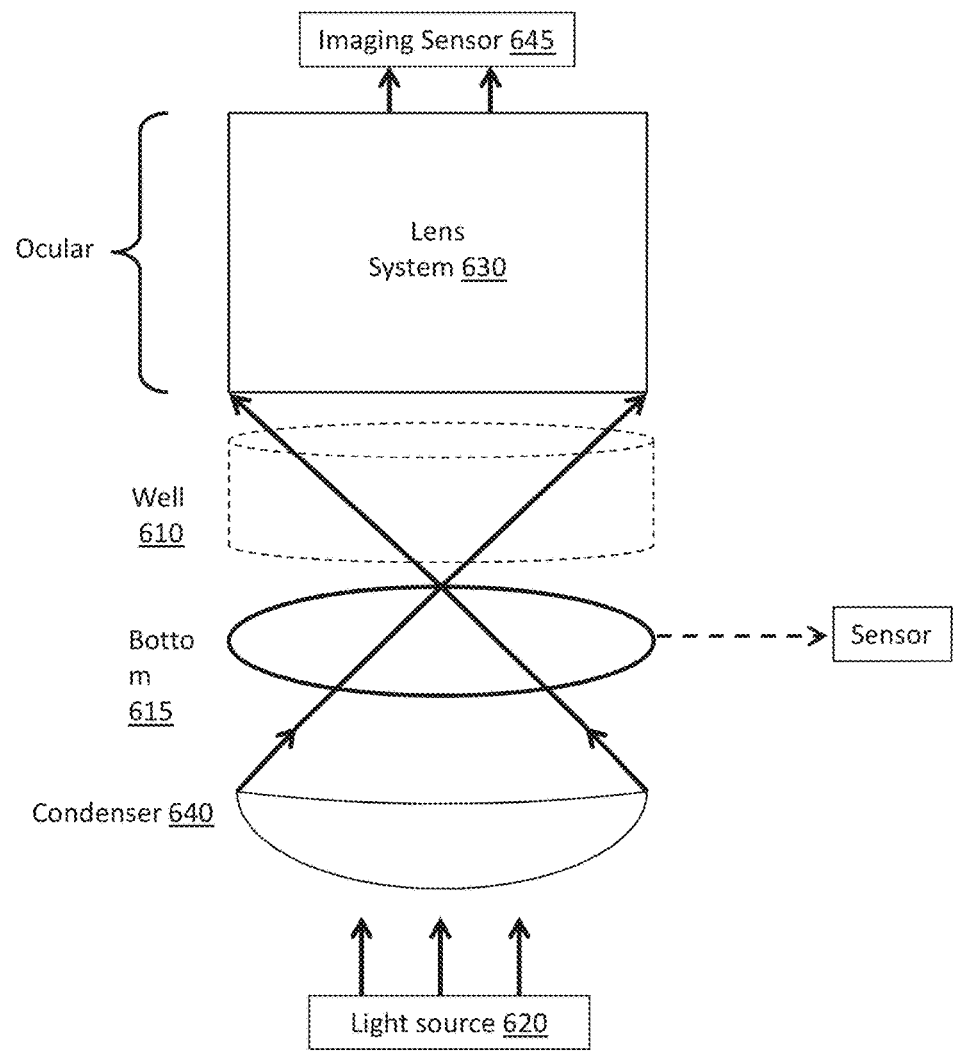
FIG. 6a depicts an example of a relatively complex microscopic imaging camera arrangement.
Figure 6B:
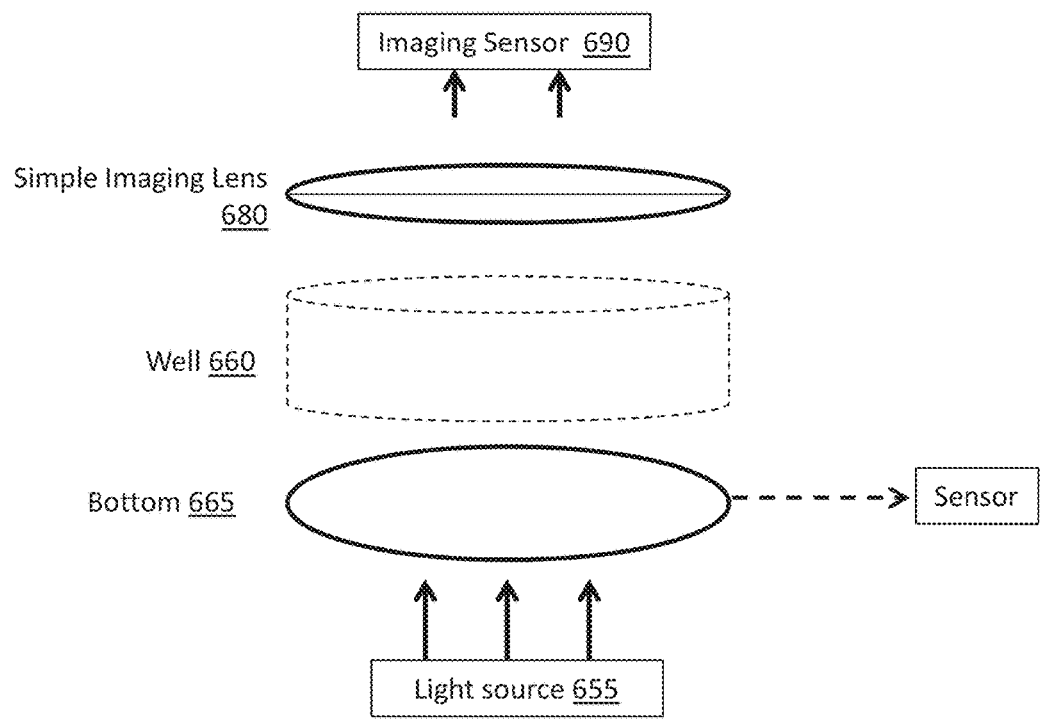
FIG. 6b depicts an example of a simplified microscopic imaging camera arrangement.

FIGS. 6a and 6b illustrate examples of microscopic imaging camera arrangement 600 and 650. In both arrangements, a well (610, 660 respectively) having a corresponding transparent bottom (615, 665 respectively) is illuminated from below using light source (620, 655 respectively). Arrangement 650 utilizes a simple imaging lens 680 so that an image is sensed by imaging sensor 690. Arrangement 600 utilizes a more complex lens system 630 and condenser 640, so that an image is sensed by imaging sensor 645. FIGS. 6a and 6b also illustrate that wells (610, 660 respectively) may be fitted with sensors (shown) and fluidics (not shown).

Individualized Environments

The arrangements and example embodiments described thus far provide various combinations of controlled fluidic inflow/outflow individualized to each well and individually monitoring of each well. However, the arrangements and example embodiments described thus far have a remaining limitation in that they provide the same gas, temperature, humidity, illumination, and imaging for all wells in the incubator. Additional embodiments provide several approaches to overcome this limitation, for example:

1. Supporting a plurality of microplates in the incubator and providing a plurality of separate individualized environments to subsets of the plurality of microplates—in the extreme an embodiment can be configured to provide separate individualized environment to each microplate in the incubator.
2. Providing a plurality of separate individualized environments to subsets of wells of the microplates—in the extreme an embodiment can be configured to provide separate individualized environment to each well in a microplate.
3. Providing a combination of these approaches.

Figure 7A:
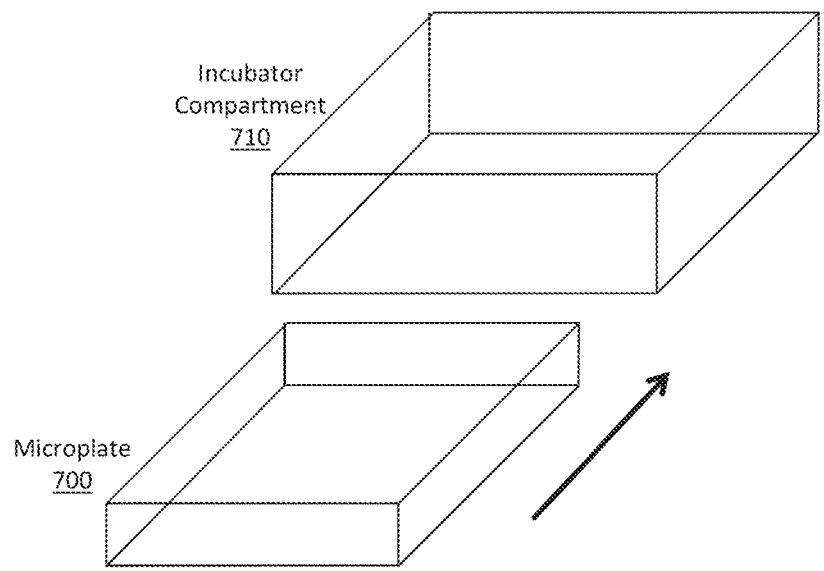
FIGS. 7a and 7b depict an arrangement in which a microplate is inserted into one of a plurality of compartments within the incubator.

As example of approach 1 (and its role in approach 3), various embodiments can be configured to provide a plurality of separately individualized incubator environments, each accepting one or more microplates. As an example, not to be viewed as limited, FIG. 7a depicts an arrangement wherein a microplate 700 is inserted into one 710 of a plurality of compartments within an incubator, resulting in the nested configuration depicted in FIG. 7b. The microplate 700 enclosure within the incubator compartment 710 provides individualized plate-specific gas and media flows, temperature regulation, illumination, imaging, etc.

Figure 8A:
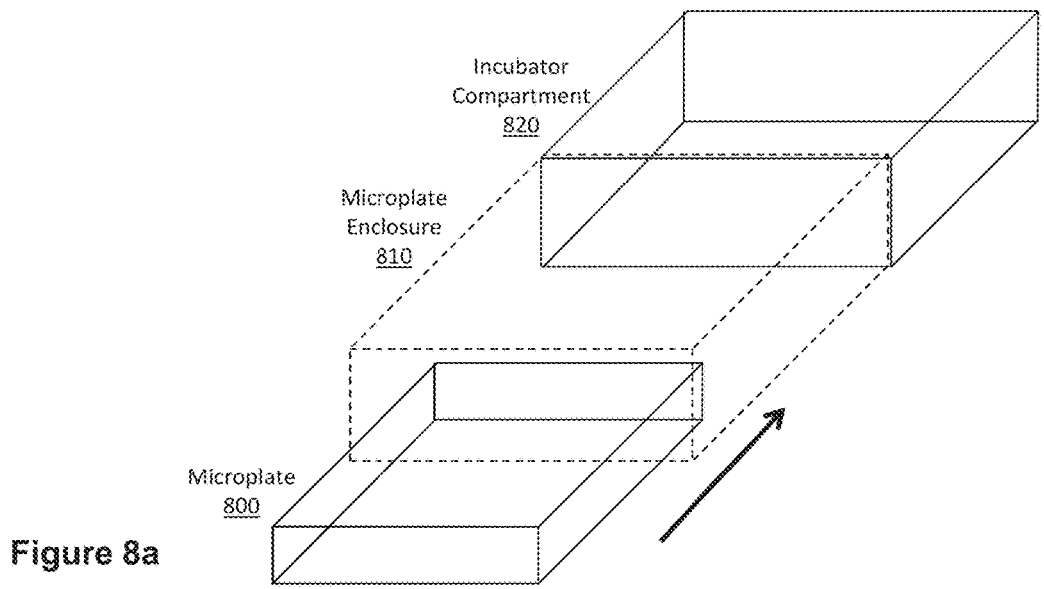
FIGS. 8a-8c depict an arrangement in which a microplate is inserted into a microplate enclosure that in turn is configured to be inserted into one of a plurality of compartments within the incubator.
Figure 8B:
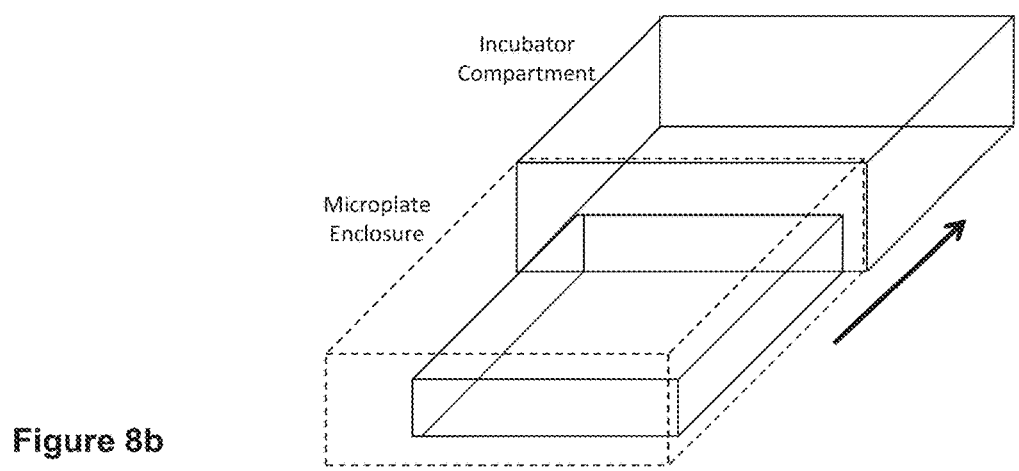
Figure 8C:
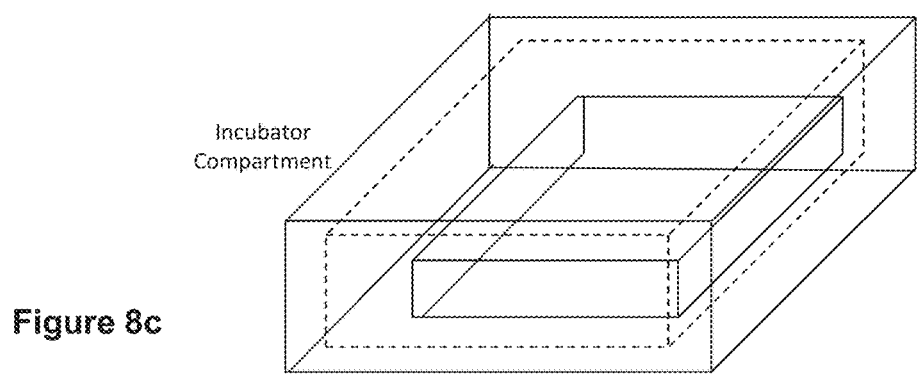

As another example of approach 1 (and its role in approach 3), not to be viewed as limited, FIG. 8a depicts an arrangement wherein a microplate 800 is inserted into a microplate enclosure 810 which in turn is configured to be inserted into one 820 of a plurality of compartments within an incubator as shown in FIG. 8b, resulting in the nested configuration depicted in FIG. 8c. The microplate enclosure within the incubator compartment provides individualized plate-specific gas and media flows, temperature regulation, illumination, imaging, etc.

Figure 9A:
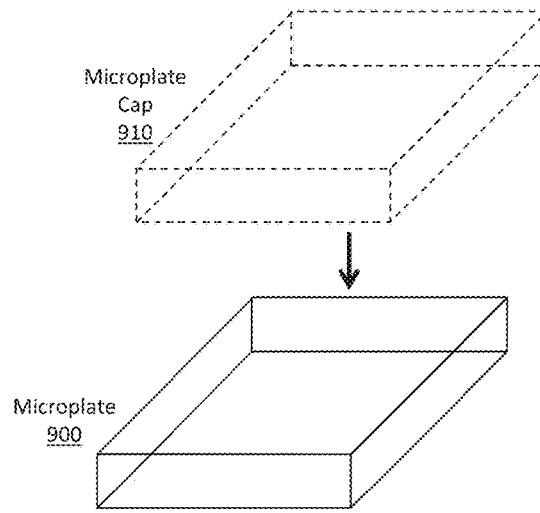
FIGS. 9a-c depict an arrangement in which a microplate is fitted with an environment-localizing microplate cap.
Figure 9B:
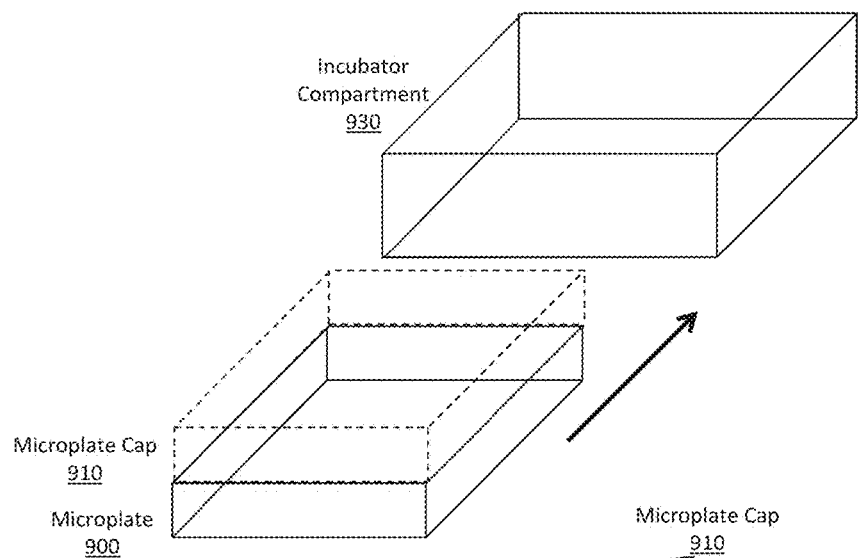

As a further example of approach 1 (and its role in approach 3), not to be viewed as limited, FIG. 9a depicts an arrangement wherein a microplate 900 is fitted with an environment-localizing microplate cap 910. The microplate 900 and fitted microplate cap 910 are configured to be inserted into one 930 of a plurality of compartments within the incubator as shown in FIG. 9b, resulting in the nested configuration depicted in FIG. 9c. The arrangement within the incubator compartment provides individualized plate-specific gas and media flows, temperature regulation, illumination, imaging, etc.

Figure 7B:
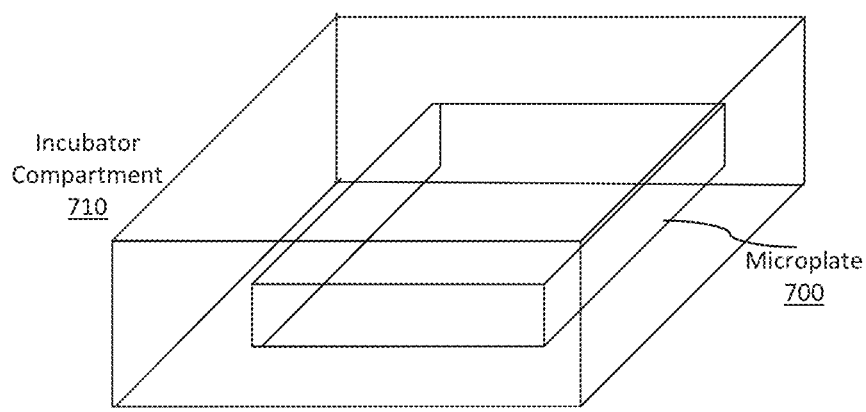
Figure 9C:
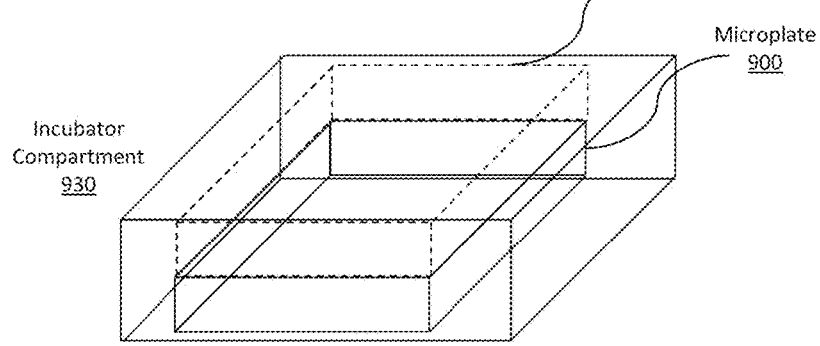

Regarding gas handling, aspects of the arrangements such as that depicted in FIG. 4b and FIG. 4a can be replicated for each such instance of FIG. 7b, FIG. 8c, FIG. 9c, or related nested arrangements. Temperature and humidity control, illumination, imaging, and other arrangements can be similarly replicated. Alternatively, with regards to gas handling, a multichannel gas distribution bus can be used (instead of replicating aspects of the arrangements such as that depicted in FIG. 4b and FIG. 4a) wherein controllable amounts of selected gas components are delivered individually to each well and cap chamber. Such a multichannel gas distribution bus can be realized, for example, as (or using the same systems and methods as) a controllable multichannel microfluidic chemical bus such as that taught in U.S. Pat. No. 8,032,258 and pending U.S. patent application Ser. Nos. 13/251,286 and 13/251,288.

As to approach 2 (and its role in approach 3), the cap and site arrangement taught in pending U.S. patent application Ser. No. 13/761,142 can be adapted and/or modified to support living cells, either individually or in culture. For example, in the context of pending U.S. patent application Ser. No. 13/761,142, the microplate depicted in FIG. 1, either in standard commercially available passive ("ice tray") form, fitted with biosensors, fitted with fluidics, etc. can be regarded as the "removable replaceable media element" taught therein.

Cap and Well

Figure 10A:
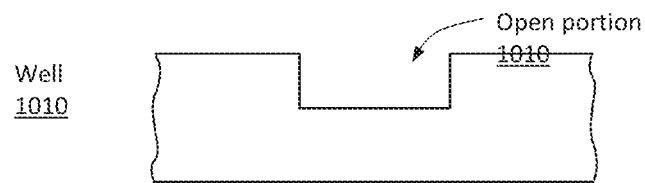
FIG. 10a depicts a representation of an example cross-section of an individual well of a microplate (such as that depicted in FIG. 1) and immediately surrounding microplate material.
Figure 10B:
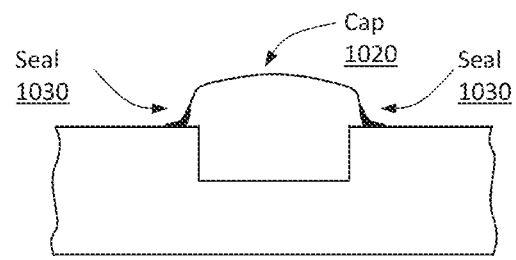
Figure 10C:
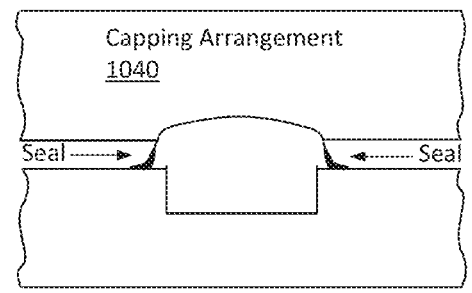
FIG. 10c depicts a variation on the arrangement depicted in FIG. 10b wherein the cap is not a separate self-contained structure but instead rendered as a well or cavity of a larger piece of structural material.

FIGS. 10a-10c depicts representation of an example cross-section of an individual well 1000 of a microplate (such as microplate 100 depicted in FIG. 1) and immediately surrounding microplate material. In some embodiments, well 1000 that is e.g., part an open welled microplate, such as may be part of incubator system 300.

As illustrated in FIG. 10a, well 1000 has an open portion 1010. FIG. 10b depicts a representation of an example separate self-contained cap 1020 and associated fluidic/gas-tight seal 1030 that can be placed against the open portion 1010 of the microplate well 1000. FIG. 10c depicts a variation on the arrangement depicted in FIG. 10b wherein the cap 1040 covers not only open portion 1010, but also top surface of well 1000. In some embodiments, cap 1040 is not a separate self-contained structure but instead rendered as a well or cavity of a larger piece of structural material.

Both of the arrangements depicted in FIG. 10b and FIG. 10c can transform the well of a microplate (such as that depicted in FIG. 1) into a separately sealed chamber to which provisions for one or more of fluidics, gas exchange, temperature control, sensors, imaging, and other functions can be dedicated. The one or more of fluidics, gas exchange, temperature control, sensors, imaging, and other functions can be rendered in the microplate, as described above, or in the cap, as described in pending U.S. patent application Ser. No. 13/761,142, or in both in the cap as well as in the (also as described in pending U.S. patent application Ser. No. 13/761,142).

As an example, fluidics can be considered: In addition to (or as an alternative to) microfluidics and sensors rendered within the microplate, fluidics arrangements linking to caps mating with one or more wells of a microplate can be provided. Additionally, the adapted and/or modified cap arrangement (as illustrated in FIGS. 10b and 10c) can be configured with fixed sensors (for example, sensors for one or more of temperature, $O_2$, $CO_2$, NO, $CH_4$, $NH_3$) in the cap and special purpose sensors (for example monitoring biomarkers, other excreted proteins, and waste products) on the removable replaceable media element. The cap can also be configured to provide gas exchange, regulated thermal control, and arrangements can be used to dispense protective materials to prevent or fight unintended infections from various phages, pathogens, parasites, and competing intruder cell types. The fluidic environment provided by the cap can also be used to introduce materials to be exposed to the cells, for example drugs, pharmaceutical agents, photosensitizers, fluorophore probes/markers, etc.

As another example, fluidics arrangements provided by a cap can be configured to provide individual wells in the microplate with controlled fluidic delivery of nutrients. As another example, fluidics arrangements provided by a cap can be configured to provide individual wells in the microplate a controlled fluidic delivery of dissolved gases. Additionally, fluidics arrangements provided by a cap can provide controlled fluidic removal of waste materials so as to support life processes in one or more wells of the microplate. The fluidics arrangements, which can also be used for gas exchange and other types of material transport (including slurries and suspensions) can include use of a controllable multichannel microfluidic chemical bus such as that taught in U.S. Pat. No. 8,032,258 and pending U.S. patent application Ser. Nos. 13/251,286 and 13/251,288. In some embodiments these fluidic paths can be used to carry solvent(s), cleaning fluids and/or clearing gases as taught in pending U.S. patent application Ser. Nos. 11/946,678 and 13/314,170.

Figure 11A:
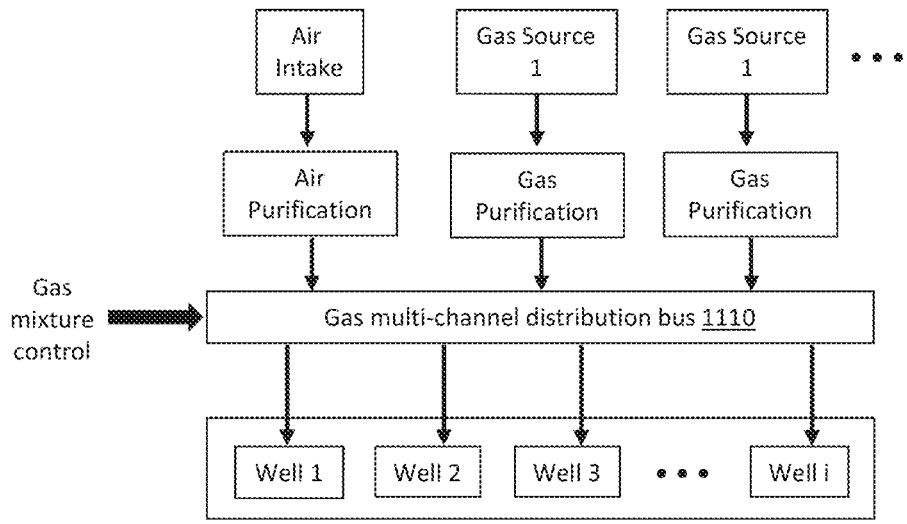
FIG. 11a depicts a variation on the arrangement depicted in FIG. 4b wherein the centralized gas mixture operation is replaced with a multichannel gas distribution bus and controllable amounts of selected gas components are delivered individually to each well and cap chamber.
Figure 11B:
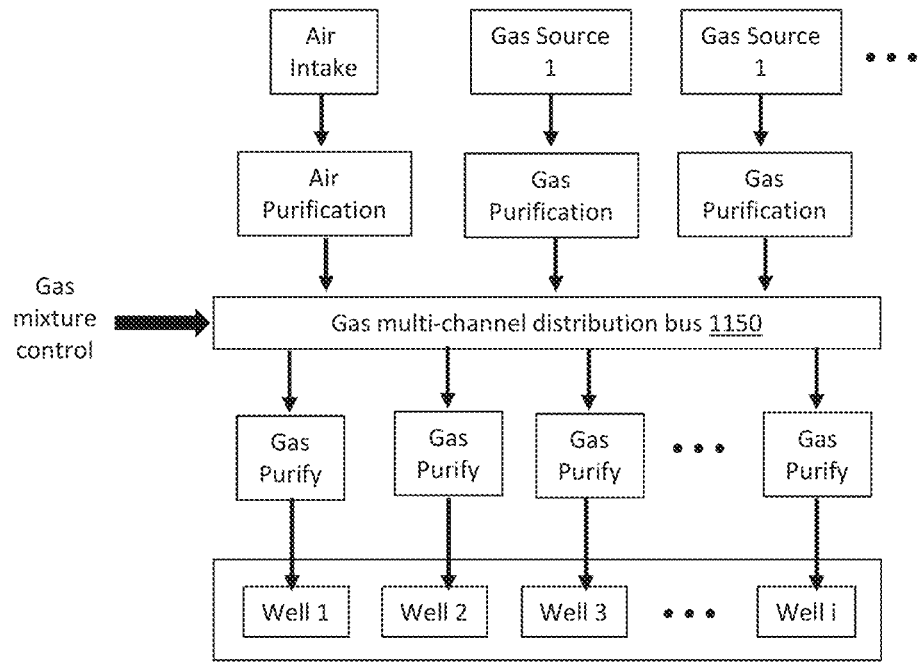
FIG. 11b depicts a variation on the arrangement depicted in FIG. 11a wherein separate post-distribution gas purification is provided for at least some of the chambers created by well and cap pairs.

FIG. 11a depicts a variation on the arrangement depicted in FIG. 4b wherein the centralized gas mixture operation is replaced with a multichannel gas distribution bus 1110 and controllable amounts of selected gas components (as controlled e.g., by controller 420) are delivered individually to each well and cap chamber. The multichannel gas distribution bus can be realized, for example, as (or using the same systems and methods as) a controllable multichannel microfluidic chemical bus such as that taught in U.S. Pat. No. 8,032,258 and pending U.S. patent application Ser. Nos. 13/251,286 and 13/251,288. FIG. 11b depicts a variation on the arrangement depicted in FIG. 4b wherein separate post-distribution gas purification is provided for at least some of the well and cap pairs.

Figure 12:
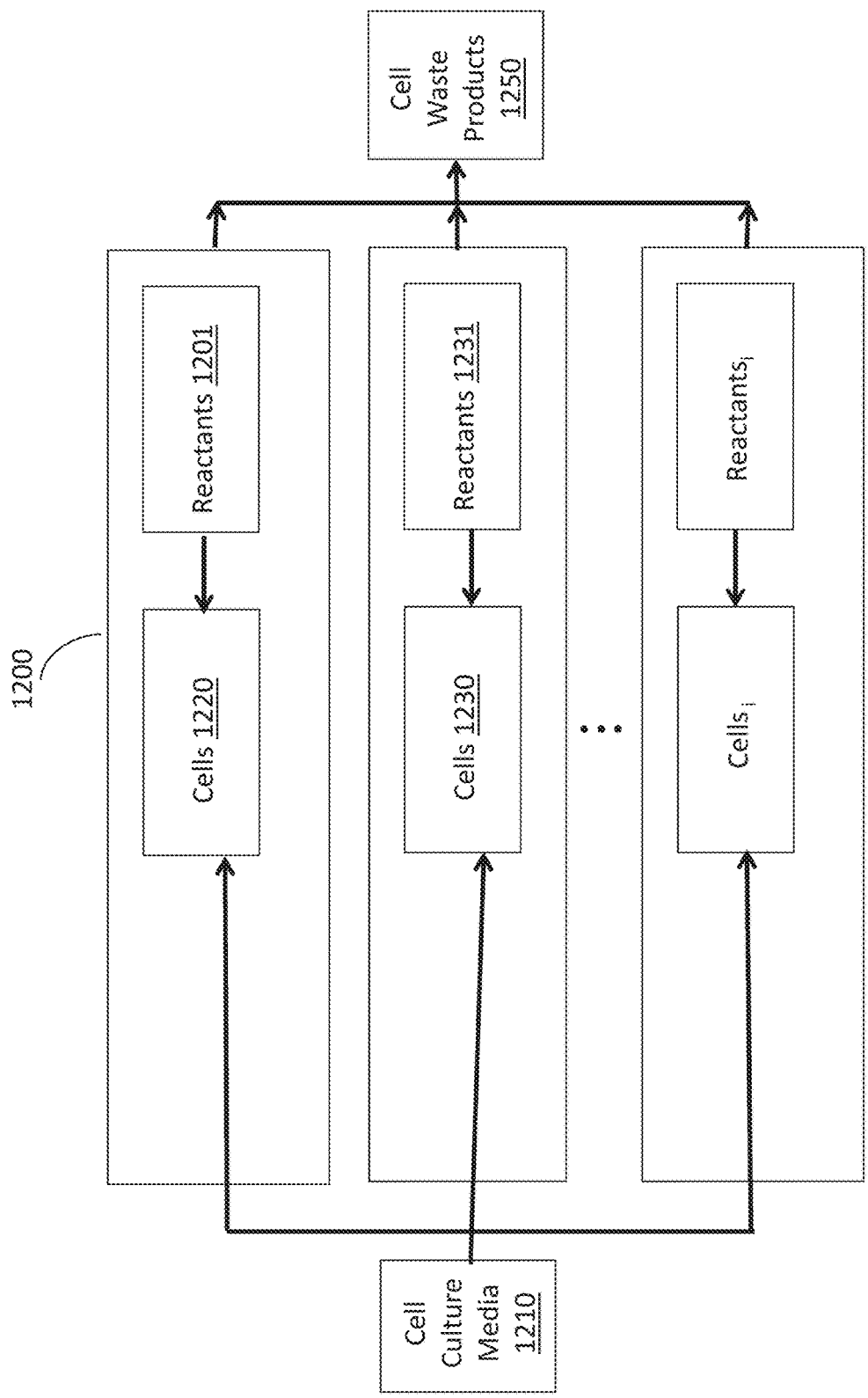
FIG. 12 depicts a system for providing a plurality of separately controlled environments, separately controlled reagent introduction, and separate monitoring, each for an associated cell culture or group of cell cultures according to certain embodiments.

FIG. 12 illustrates a fluid media replenishment system 1200 according to some embodiments. System 1200 provides separately controlled environments, separately controlled reactant introduction, and separate monitoring, each for an associated cell culture or group of cell cultures. Thus cell culture (or group of cultures) 1220 receives its own separately controlled thermal and gaseous control and reaction or substrate monitoring, while culture (or group of cultures) 1230 receive its own separately controlled thermal and gaseous control and reaction or substrate. The arrangement depicted in depicted in FIG. 12 also shows the distribution of fluidic cell culture media 1210 into cell culture wells and the passage of excess fluidic cell culture media containing cell waste products 1250 and other discards.

Embodiments can further include other of features, adaptations, and modifications of features, arrangements, methods, and technologies described in pending U.S. patent application Ser. No. 13/761,142 suitable for adding value to a cell incubator.

Additionally, in some embodiments dedicated imaging camera arrangements can be provided for at least some of the well and cap chambers.

The incubated cells supported in the described environment can be advantageously used in various experiments heretofore not otherwise practical or feasible. Some example experiments include:
  Controlled regulation of oxygen to invoke various types of oxygen stress,
  Controlled regulation of nitric oxide to study concentration effects on cell processes,
  Controlled dispending of pharmaceutical agents to the cells,
  Controlled optical stimulation of native cells or cells prepared with photosensitizers, etc.,
  Controlled regulation of temperature and gaseous portion for each isolated specific environmental cell growth,
  Controlled dispending of infectious agents to the cells,
  Controlled dispending of chemical or biochemical compounds to the cells,
  Controlled dispending of toxins and non-infectious agents to the cells.

In the experiments, various sensors (and imaging cameras if used) can be employed to monitor the status, condition, and response of the living cells. Other types of experiments, features, enhancements modifications, and design variations are anticipated and provided for by the present application.

For example, various embodiments can focus on three main functions—regulating and the cultural environment, monitoring the condition such as concentrations of the adding substances during incubating, and analyzing the cellular responses—cell assay. Controlling cell growth conditions—temperature, gaseous portion, humidification, and sterilization—will be able to modify each factor to meet the optimal condition for cell growth and studied designs. For example, various types of cells require distinctly different environmental conditions. Additionally, in order to study the cell responses to different conditions such as condition of oxygen levels and carbon dioxide levels, it is desirable that a new generation cell incubator be able to adjust environmental and other experimental factors during incubating in a precisely control manner for different well and cap chambers. For instance, embodiments of the incubator can mimic hypoxia (low oxygen level) using a 1:19 $CO_2/N_2$ mixture and can mimic normoxia (normal tissue and cell culture oxygen level) using a 5% $CO_2$ in each cell culture environment.

The process of cell culture contains mixing and washing steps. Since errors from taking the cells out of the incubator for professing the mixing and washing steps inducing a discontinuing the incubated condition may occur. The embodiment of the incubator focuses on combining every step of the cell culture processes in one place by embodying microfluidic systems and biosensor detection to the incubator. The microfluidic systems allow the solutions to automatically mix and move to where the cells locate during incubating.

The sensor implementation, fluidic/gas interfacing, miniaturizing approaches, electrical interfaces and optical interfaces, and further by collocating, and integrating a large number highly-selective sensors and chemical sensors—together with appropriately selected supplemental sensors (for example temperature, pH, selective ions, etc.)—the present application provides a rich ability to flexibly perform, create, deploy, maintain, and update a wide range of panels, assay, array, and/or sequence of tests for a wide range of substances and microorganism can be created.

Monitoring the biological process of the cells—temperature, pH, $CO_2$, etc.—and the levels of the studied substances, such as nitric oxide and other free radical during incubating is applied to the present application. To monitor the biological processes and measure the quantity of the candidate substances, biosensor is developed and applied to the incubator. The signal from the sample translocate through a semiconductor cell plate, which is observed. The biosensor is also beneficial for cell assay such as apoptotic assay and cell viability assays (such as the MTT assay). In addition, chemical and biological solution is transferred from the solution's storage to the wells by using microfluidic system.

The incubator comprises the multiple independently operated and controlled cell culture chambers. These can, for example, be arranged in the form of an array, micro-well array, assay, etc. Cell culture environmental control and sensors are applied to an individual chamber. To control the cell culture condition such as temperature and gaseous portions, each individual chamber consists of a cap, which provides a selective the cell culture condition. For example study the effects of NO on gene expression in hypoxia condition. In this study, to operating this experiment, NO donors are added to the cell samples in low $O_2$ levels culture condition and they are also added into other samples in normoxia condition as controls.

In some embodiments, each well and cap chamber comprises dedicated sensors that are able to detect biological or chemical processes during cell culturing.

Such features more readily facilitate the simultaneous parallel study cell cultures subjected to controlled differences in concentrations, environmental controls, and introduced substances.

Example Cell Culture Requirements

To keep cell cultures alive outside of tissues, a number of environmental, nutrient, and sterility factors must be maintained. Additionally, in duce cell growth, hormones or growth factors must be provided. A few of these aspects are considered here in the context of various embodiments.

Temperature Control:

Temperature plays an important role in cell culture. For example, the length of bacteria, *L. pneumophila* serotype 1 strains AATCC33152, responded to variations in temperature over a range from 30.0° C. to 47.0° C. in 0.5 steps using a developed temperature gradient incubator [1]. Additionally, cells are able to survive at temperatures 10° C. to 20° C. below the core temperature, but they will immediately destruct if the temperature reaches 40° C. [2]. In general, in the cell biology field, the culture temperature is 37° C. (human body temperature). However, various cell types require other cell culture conditions. Typically controlled temperature ranges of 30.0° C. to 47.0° C. would be maintained by embodiments employing heating and cooling functions as required. In some applications the ability to vary temperature over a range as a function of time or as an experimental parameter is advantageous.

Gaseous Environment:

The cell grown requires a combination of 90-95% air and approximately 5% $CO_2$. The partial pressure of oxygen is at 18%. However, to study the effect on concentration of $O_2$ such as in hypoxia condition (lower $O_2$ levels), incubators should contain the mixture of carbon dioxide ($CO_2$), nitrogen ($N_2$), and air to obtain the desired gaseous environment [3]. Indeed, the cells also produce $CO_2$, which will affect to a normal pH (pH 7.0-7.4) of the cell medium. Furthermore, because of requiring a sterilization of the cell culture and there is a contamination from the air that might damage the cells, a filtration system such as a high-efficiency particulate air (HEPA) is regarded to establish in the incubator.

Humidification:

Humidification is important to control the osmolarity of the cells. Osmolality involves with the movement of the solvent through a semi permeable membrane into a solution which has higher concentration of solute. If the compressed air in the incubator has really low moisture content, it will cause evaporation of the cell medium and increase osmolality. Consequently, the cells will lose water and shrivel. On the other hand, at high moisture content, a cell will gain too much water and can become lysed. Accordingly, it is useful for some embodiments to incorporate a controlled humidification will be applied to the internal chamber of the incubator without losing water due to the movement of the device. Alternatively, a water tray or similar arrangement that facilitates intake of water through ports and, for example, saturates a pad at the bottom of the system, regulates the humidity. The flow of the gaseous mixture draws moisture from the pad which will maintain the humidification of the environment. Embodiments can employ know technologies such as evaporation and condensers to regulate humidity of gases. In some embodiments, thermoelectric devices can be used to create electrically-controlled cooled surfaces for condensing moisture from air and gas mixtures and heated surfaces for condensing moisture from air and gas mixtures.

Sterility:

Sterility plays in an important role in cell culture. Thus, the incubation apparatus needs antimicrobial environmental condition, for example employing appropriate amplitudes and wavelengths of UV light in appropriate settings so as to kill ambient bacteria. In the case of unintended bacterial infection of an active cell culture, agents such as antibiotics or bacteria phages can be useful to save the life of the cells in the infected culture.

Gentle Fluid Administration

As discussed earlier in conjunction with FIG. 12, various embodiments can advantageously provide distribution of fluidic cell culture media into cell culture wells and the passage of excess fluidic cell culture media containing cell waste products and other discards. Additionally, various embodiments can advantageously provide reagents such as hormones, signaling donors, stains, etc. as well as other materials such as drugs, dissolved gases, infectious agents, antibiotics, etc. which can be introduced into cell culture wells by fluids.

Figure 13:
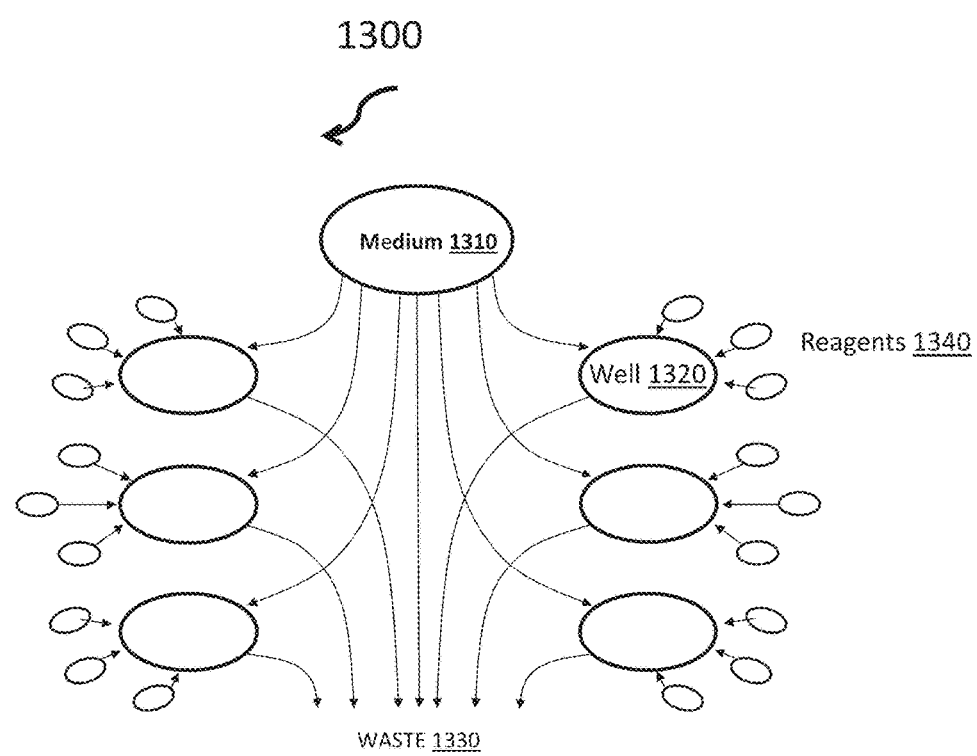
FIG. 13 depicts an example arrangement wherein cell culture media fluid flows from a fluid source to individual cell culture wells and from there to fluidic waste handling, and wherein reagents such as hormones, signaling donors, stains, etc. can be introduced into cell culture wells by fluids.

FIG. 13 depicts an example arrangement 1300 wherein cell culture media fluid 1310 flows from a fluid source to individual cell culture wells 1320 and from there to fluidic waste handling 1330, and where reagents 1340 such as hormones, signaling donors, stains, etc. can be introduced into cell culture wells 1340 by fluids. A similar arrangement can be used for fluidically introducing other materials such as drugs, dissolved gases, infectious agents, antibiotics, etc. into cell culture wells. In some embodiments, the flows of media fluid 1310 are individually controlled for each microplate, e.g., by controller 420. In some embodiments, the flows of media fluid 1310 are individually controlled for groups of wells within a specific microplate, e.g., by controller 420. In some embodiments, the flows of media fluid 1310 are individually controlled for each well, e.g., by controller 420.

Figure 14B:
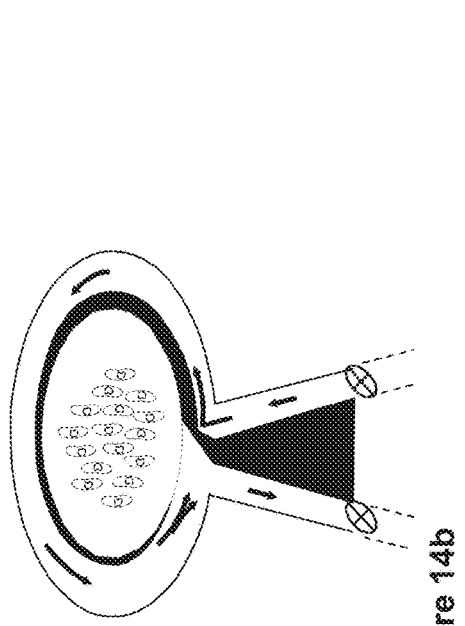
FIG. 14a and FIG. 14b depict example arrangements for providing gentle fluid flow over a ramped circular flow arrangement around a rim of a well.
Figure 14A:
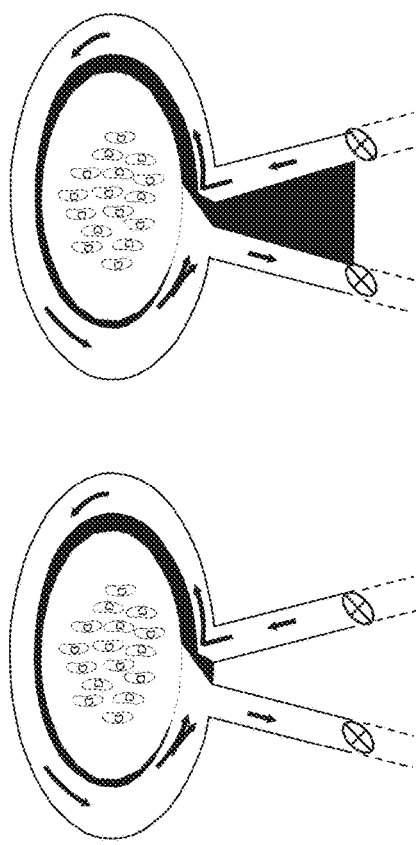

In some embodiments, care is taken in the introduction of the fluidics 1310 into the cell culture wells 1320 so that the forces exerted by fluid currents do not damage cell adherences or other physical aspects of the cell culture. One approach involves using extremely low rates of fluid flow. Another approach can also help uniformize the distribution of new fluidic material over the surface of a well 1320. This approach, illustrated in FIGS. 14a and 14b, involves gentle fluid flow over a ramped circular flow arrangement around a rim of a well.

Figure 15:
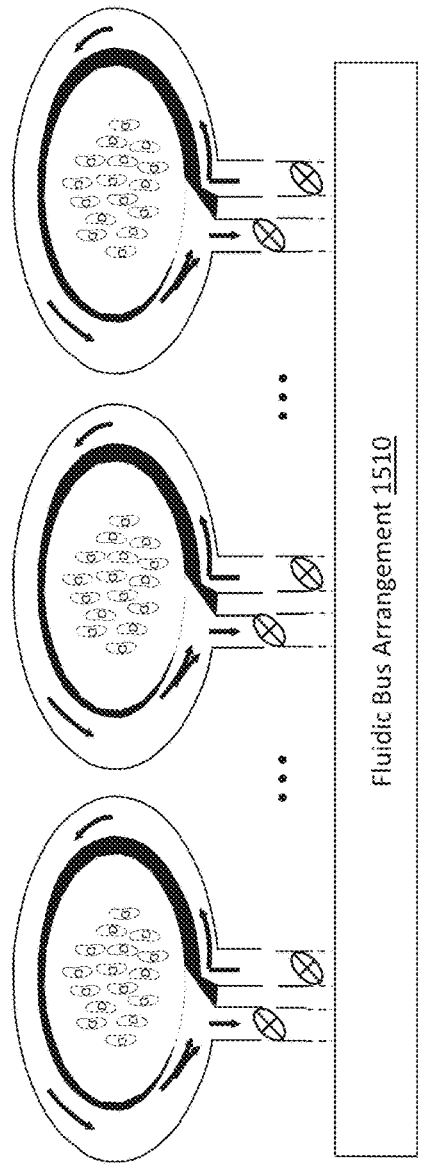
FIG. 15 depicts an arrangement wherein the rate and contents of flow delivery is individualized by connecting arrangements such as those of FIG. 14a or FIG. 14b to an instance or adaptation of controllable microfluidic bus technologies.

One approach to individualizing the rate and contents of flow delivery is by connecting such arrangements to an instance or adaptation of controllable microfluidic bus technologies 1510, such as those taught in U.S. Pat. No. 8,032,258 and pending U.S. patent application Ser. Nos. 13/251,286 and 13/251,288), for example as depicted in FIG. 15.

In some embodiments, fluids can be introduced from below the cell wells, as depicted in FIG. 16a. In other embodiments, fluids can be transported in and out of individual cell culture wells 1630 by surface-exposed trays 1620, for example as depicted in FIG. 16b, or from the edges of the well sides. Combinations of these approaches can also be used, for example as depicted in FIG. 16c.

Temperature Control

Various methods can be used to control the temperature of group of cell culture wells and individual cell culture wells, for example:

1. Control of gas environment temperature
2. Control of media fluid temperature
3. Control of microplate material temperature
4. Control of individual well wall temperature.

Approaches 1-4 can be accomplished, for example, with controlled thermoelectric devices (providing cooling and/or heating) as well as electrical resistive heating elements. Approach 1 can also employ refrigeration techniques.

Approaches 3 and 4 are also particularly suitable to fluidic heating and cooling methods employing associated fluidics throughout a microplate. Thus systems and methods for the temperature control of fluids can address Approaches 2-4. As to systems and methods for the temperature control of fluids, self-contained approaches can use controlled thermoelectric devices to providing cooling and heating, or thermoelectric devices to providing cooling and electrical resistive heating elements for heating. In some embodiments, two reservoirs of fluids, one cooled and the other heated, are used and mixed in various proportions to obtain the desired fluid temperature.

Higher precision in temperature control can be obtained by employing thermal insulation among wells, on microplate surfaces, etc. and well as through the use of temperature sensors driving feedback controllers, for example employing simple on/off control or continuous-range control using for example PID ("Proportional/Integral/Derivative) feedback controller systems and/or algorithms.

Sensors and Detection for Cell Culture Wells and Well/Cap Chambers

The microprocessor-controlled microfluidic-based incubating platform for cells can be configured to comprise removable replaceable media element comprising an array of sensors. These sensors can include for example electrochemical, bio-FET, and optical sensor technologies. In various embodiments sensors can configured to measure concentrations of gases, chemical substances, proteins, biomarkers, ions, etc. as well as other quantities such as temperature and optical properties.

This section briefly describes a number of existing and emerging biosensor and chemical sensor technologies and approaches suitable or adaptable for full microsystem implementation. The synergistic use of existing biosensor and chemical sensor technologies and approaches, a number of adaptations others and addition sensor innovations, plus yet other adaptations and innovations, as employed in the present application will provided in later discussion.

Figure 17A:
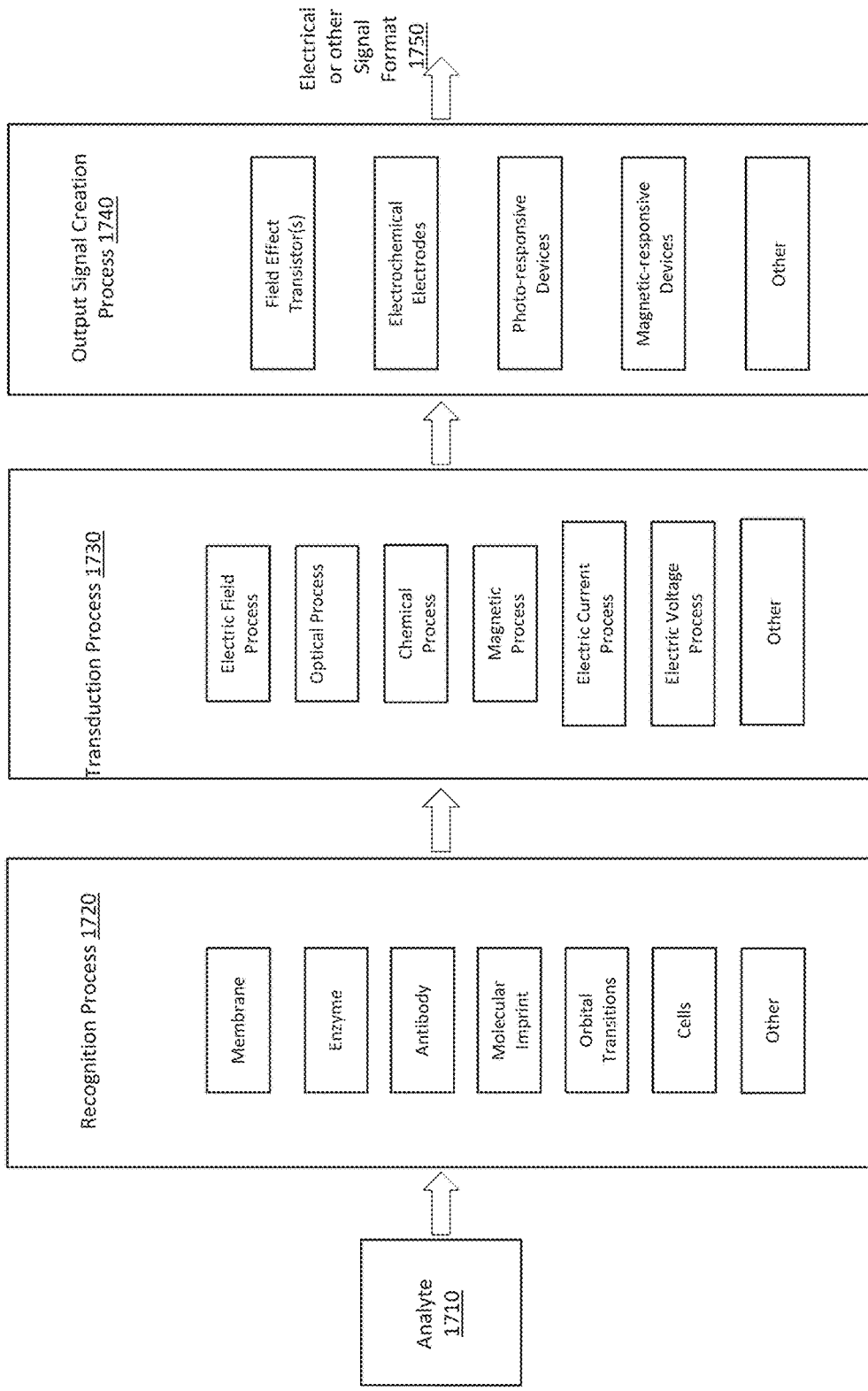
FIG. 17a depicts simplified unified view of the basis of biosensing technologies.

One simplified representation of a unified view of the basis of biosensing is provided in FIG. 17a. A sample or analyte 1710 is brought into interaction, communication, and/or physical contact, with a recognition process 1720. In general, the recognition process 1720 internally employs a selective detection material or process such membranes, enzymes, antibodies, cells, molecular imprint materials, electron orbital transitions, magnetic resonances, etc. The recognition process 1720 results in an observable or measurable effect that is input to a transduction process 1730 (comprising, for example, one or more of an electric field, optical, chemical, magnetic, electric current, electric voltage, etc.) to an output signal process 1740 (which may comprise one or more field effect transistors, electrochemical electrode arrangements, photo-responsive electric devices, magnetic-responsive electric devices, etc.), typically producing an electrical signal 1750. The many components of each class (distinguished as columns in the Figure) can be arranged in various combinations to form an extensive plethora of sensing approaches, systems, methods, and devices. Some sensing approaches can include more than one choice from each class—for example, an enzyme cascade could be used, and in one example embodiment of the present application to be discussed, living cells may be used to provide front-line recognition processes, and materials secreted through the membranes of the living cells can be subjected to at least a second-line recognition process (employing for example one or more enzymes, antibodies, molecular imprinted materials, etc.).

Figure 17B:
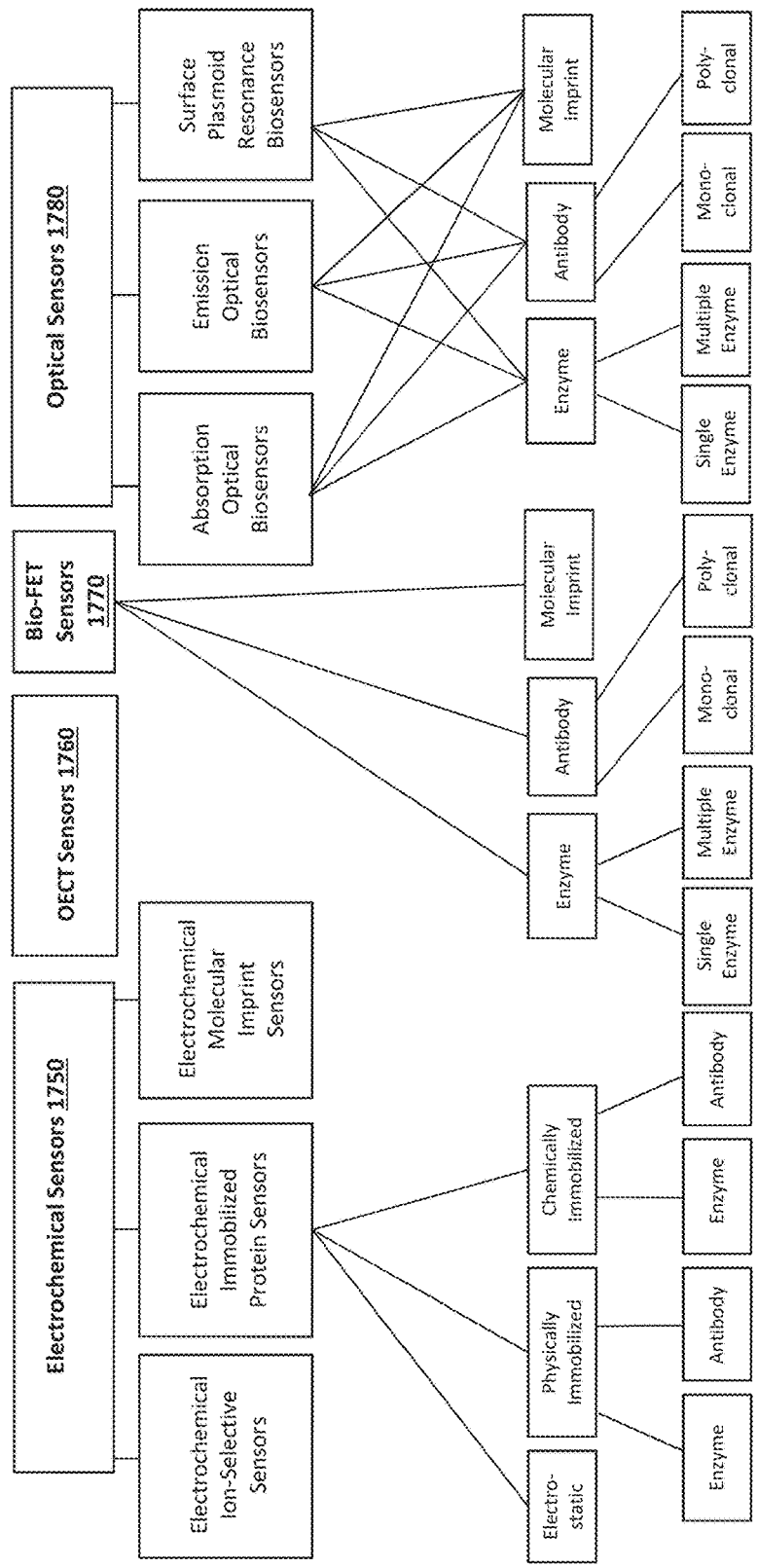
FIG. 17b provides a view of the diversity of biosensor technologies and approaches suitable or adaptable for full microsystem implementation.

In particular there are a rapidly increasing number and diversity of technologies and approaches for chemical sensor and biosensor that are suitable or adaptable for microsystem implementation. Although not comprehensive or exhaustively or precisely organized, FIG. 17b provides a relatively comprehensive view of biosensors and approaches suitable or adaptable for microsystem implementation. Many of these sensor technologies and approaches are still either being prototyped in relatively large sizes, mostly for the convenience of inexpensive and flexible construction in a traditional laboratory. Many others are current implemented as small structures supplemented with large laboratory instruments and devices that can be simplified, focused, specialized, adapted, or otherwise miniaturized. Broadly these can be classified into at least the following electronic device and operation categories:

Electrochemical sensors 1750;
Organo-Electrochemical Transistor (OECT) sensors 1760;
Bio-FET sensors 1770;
Optical sensors 1780 (these to be adapted to comprise opto-electrical devices), and these can include at least the following active sensing agents and sensing components:

Molecular imprint materials ("MIMs");
Antibodies (as well as synthetic antibodies);
Enzymes (as well as other proteins, synzymes, etc.);
Photo-responsive, photo-absorption, and photo emission materials.

Various configurations and arrangements of these in turn can function as "biosensors," "immunosensors," "chemical sensors," etc. These and other relevant sensing technologies are taught in pending U.S. patent application Ser. No. 13/761,142.

A brief overview of non-imaging sensing is provided below. (As indicated above, imaging sensors can also be included for use with a removable replaceable media element; these will be discussed later.)

Electrochemical, BioFET, and ChemFET Sensing Methods

Classical, contemporary, and advancements in electrochemical sensors are known. A few remarks regarding aspects of current and emerging electrochemical sensors relevant to various aspect of the present application are made in this section.

There are various major types of electrical sensing process responsive to chemical conditions and processes that are employed in electrochemical sensors, for example:

"Potentiometric electrochemical sensors" involve measuring the difference between two potentials (in units of volts) associated with the electrodes of an electrochemical sensor, "Amperometric electrochemical sensors" involve measuring current (in units of amperes) through an electrochemical sensor, "Conductometric electrochemical sensors" (also referred to as "chemiresistors") involve measuring the "direct-current" (DC) resistance (in units of ohms) or conductance (in units of mhos) across an electrochemical sensor (resistance being the ratio of voltage to current and conductance being the ratio of current to voltage), "Impedance electrochemical sensors" involve measuring the sinusoidal alternating current (AC) reactance, either as impedance (in units of ohms) or admittance (in units of mhos) across an electrochemical sensor over an adequate range of AC frequencies.

Also of importance is a means, process, material, or other arrangement providing adequate (or useable) selectivity of the sensors response to chemical or biochemical substances of interest with respect to expected range of chemical constituents in a sample. In some cases, sensors can be made very selective (for example, an antibody-based electrochemical sensor employing an antibody that responds only to a specific protein) or selective to a family of materials and thus in some applications requiring strict limitations on what can be in an applied sample. Examples of such means, processes, materials, and other arrangements include uses of membranes, specialized crystals, enzymes, and antibodies among many other approaches, and can include combinations of multiple means, processes, materials, and other arrangements. For an extensive examples of what types of quality chemical and biochemical detections that can be accomplished with simple means, processes, materials, and other arrangements for the family of simple 3-electrode electrochemical sensors comprising simple carbon paste electrodes, the reader may consult the extensive tables in the book by I. Svancara, K. Kalcher, A. Walcarius, K. Vytras, Electroanalysis with Carbon Paste Electrodes, CRC Press, 2012, ISBN 987-1-4398-3019-2 and the techniques and applications discussed in the book by Raluca-Ioana Stefan, Jacobus Frederick van Staden, Hassan Y. Aboul-Enein, Electrochemical Sensors in Bioanalysis, Marcel Dekker, 2001, ISBN 0-8247-0662-5.

The means, process, material, or other arrangement providing adequate (or useable) selectivity further typically employs an associated limitation on the sample applied to the sensor. For example, some sensors approaches are relevant only to dry gases, others relevant only to liquid samples, while others relevant to more complex samples such as suspensions (for example comprising cells), gases dissolved liquids, materials at thermodynamic critical points (such as vapors and gases including vapors), slurries, gases comprising particulates or colloids, emulsions in various stages (flocculation, creaming, coalescence, Ostwald ripening, etc.), micelles, etc. as well as combinations of these.

Regarding miniaturization, it is noted that electrodes whose diameter is smaller than 20 μm ("microelectrodes") provide best performance as amperometric chemical sensors. Additionally, in the miniaturization potentiometric ion sensors, a chemical species-selective membrane is placed directly on (or used as) the insulator of a Field Effect Transistor (FET) input gate terminal, resulting in a miniaturized chemically selective field-effect transistor (CHEMFET) or ion-sensitive field-effect transistors (ISFET) It is noted that the miniaturization of the reference electrode compartment within a potentiometric ion sensor limits its operational lifetime. However, aspects of the present application prevent the need for long operational lifetimes and this long standing limitation and concern can be de-emphasized.

Electrochemical impedance spectroscopy (EIS), also referred to or associated with Dielectric Spectroscopy (DS) and Impedance Spectroscopy (IS), measures the electrical impedance of an analyte over a range of frequencies. The electrical impedance is responsive to the dielectric permittivity properties of the analyte which due to the electric dipole moment interaction with time-varying imposed (usually electrical) fields. In contrast to the voltammetry and amperometry electrochemical sensors described above (which involve measurement of DC or pulsed-DC electrode current as a function of applied electrode-solution voltage and rely on changing in electrode conditions), impedance sensors measure the electrical impedance by imposing a small AC voltage between sensor electrodes over a series or swept range of frequency and measuring the resulting AC current. As frequency increases the dominating electrochemical processes evolve through regimes of ionic relaxation, dipolar relaxation, atomic resonances, and electronic resonances at higher energies.

An emergent subclass of electrochemical transducers are Organo-Electrochemical Transistor (OECT) sensors employing immuno-recognition materials. Examples of these have been constructed that claim 1 ppm sensitivity. OECT sensors can operate in at least two different mechanisms:

Doping/Dedoping effects, for example where an antibody immobilized on the surface of a Field Effect Transistor gate channel surface binding to a charged ligand, the resulting fixed local charge that attenuates ion diffusion into the channel, thus altering the channel conductivity.

Antibody conformational changes, for example where an antibody is incorporated into a channel whose conductivity is affected by conformational changes in antibody that are induced by ligand binding.

Classical, contemporary, and advancements in "bioFET" sensors are known. An example is an ion-selective field effect transistor ("ISFET"). Most ISFETs employ an analyte solution as the gate electrode of the Field-Effect Transistor (FET), while the source and drain of the ISFET are as those of a typical Metal-Oxide Semiconductor Field-Effect Transistor (MOSFET). The gate insulator, typically made employing $SiO_2$, $Si_3N_4$, $Al_2O_3$ and $Ta_2O_5$), can be affixed or otherwise modified to include or attach ion-selective substances. The selective activation by associated ions affects the electric fields presented to the gate insulator, in turn varying the current through the FET channel. Such a sensor can be used to sense pH and concentrations of various chemical compounds that affect the operation of sensors in a larger system examining the same sample. Further, additional materials and layer structures can be attached which comprise bio-selective materials that, when selectively activated by associated biomolecules, create ions that are measured by the ion-selective sensor. In order to miniaturize some ISFET arrangements, the depicted reference electrode becomes impractical and/or a limitation—for example due to issues of relative physical size and active-use aging—and Reference Field Effect Transistors (REFET) are employed instead. However these, too suffer from various limitations, including thermodynamic equilibrium, recalibration needs over the sensor lifetime, and other active-use aging issues. As will be seen, the classical concerns for reference electrodes and REFETs are evaded by the usage and operational modalities employed in the present application to be disclosed. Other versions incorporate highly-selective materials or other layer structures that comprise bio-selective substances that are selectively activated by associated biomolecules in a manner that affects the conductivity or induced electric fields presented to the gate insulator, in turn varying the current through the FET channel.

An aspect relevant to various embodiments is the fact that many of the electrochemical and Bio-FET sensors can be created from layered stacks of materials. Further, the materials employed in such sensors can be functionally replaced with entirely other types materials (for example, organic semiconducting and conducting polymers) that can be inexpensively "printed" via so-called "Printed Electronics" and "Functional Printing" manufacturing technologies using fancier industrial-scale forms of ink-jet printers. The present application exploits such "Printed Electronics" and "Functional Printing" manufacturing technologies (as will be discussed later).

Optical (Non-Imaging) Sensing Methods

Classical, contemporary, and advancements in optical markers, optical labels, and optical sensors relevant to biological analysis are known. A few remarks regarding aspects of current and emerging optically-based detection technologies relevant to various aspect of the present application are made in this section.

In most contemporary laboratory instruments, space-consuming expensive precision optical elements, such as diffraction gratings with precise alignments to photodiode arrays, are employed. However, an aspect relevant to the present application is (as taught in Pending U.S. patent application Ser. No. 13/761,142) that many types of optically-based detection technologies such as those employed in microplate/microarray technologies and techniques can be modified or adapted for useful miniaturized implementation comprising at least some portions having layered structures suitable for fabrication by printing. Most optical sensing techniques employing optically-based technology for biochemical applications have been developed in the product and technology context of large laboratory instruments, and thus the comprehensive miniaturized implementations used in various embodiments, for example such as those in Pending U.S. patent application Ser. No. 13/761,142, differ from current trends in industry and academic research. For example, some of the modifications and adaptations to be presented leverage small ultraviolet LEDs, while other modifications and adaptations leverage a family of wavelength-selective LED based sensing technologies, such as those taught in Pending U.S. patent application Ser. No. 13/761,142 which remove with the need for large and/or expensive precision optical components and precise alignment needs requiring expensive manufacturing processes.

As to optical detection involving the emission of light, an important example of optically-based technology for biochemical applications is the use of fluorophores (also called fluorochromes) which absorb excitation light of a first wavelength (usually ultraviolet or visible light), attain an electronic excited state, and as the excited state decays emit light at a second (lower-energy, longer) wavelength, typically arranged to be in the visible (or in some cases, infrared) light range. Fluorophores are used as staining dyes for tissues, cells, enzyme substrates, etc. and used as a probe or indicator (when its fluorescence is selectively affected by effects of species polarities, proximate ions, excitation light polarization, etc.) and can be arranged to covalently bond to a biological molecule (such as enzymes, antibodies, nucleic acids, and peptides) so as to optical mark the location and presence or activity of that biological molecule. Fluorophores can be used to mark cells, structures or materials within cells, and in conjunction with antibodies and other selective or modulating agents in microarrays. Although most fluorophores are organic small molecules, it is noted that fluorophores size can sterically affect the biological molecule it is used to tag, as well as other effects. It is also noted that solvent polarity can affect fluorescence intensity.

Another optical detection involving the emission of light are chemiluminescence tags and labels. The origin of emitted light from chemiluminescence processes is distinguished from the fluorescence processes of fluorophores in that the electronic excited state producing emitted photons result from a chemical reaction instead of excitation by incoming light. One example is luminal ($C_8H_7N_3O_2$) which is employed in microarray, assays, and other detection of copper, iron, cyanides, and specific proteins by Western Blot.

Further, in measuring at least fluorophore light emission, there are at least two measurement techniques that can be made and used in marking strategy design. The first of these is measuring of the formal light amplitude or formal light intensity of the fluorophore emissions, usually spatially normalized (for example per observational unit volume of sample, per unit area of an observational field, etc.), and normalized with respect to background levels or other factors. The second of these is the measurement of fluorescent lifetime which typically are effectively unaffected by probe concentration, excitation instability, photobleaching, washout, and other phenomena complicating amplitude and intensity measurements. Since fluorescent decay times are in the range of 1-20 ns, short excitation pulses, high-speed optical sensors, and radio-frequency electronics can be required. Alternatively, phase modulation techniques, such as those described by H. Szmacinski and J. Lakowicz in the article "Fluorescence Lifetime-based Sensing and Imaging," *Sensors and Actuators B: Chemical* (*Proceedings of the 2nd European Conference on Optical Chemical Sensors and Sensors*), Volume 29, Issues 1-3, October 1995, pp. 16-24 and earlier book chapter "Lifetime-based Sensing Using Phase-Modulated Fluorometry" in *Fluorescent Chemosensors for Ion and Molecule Recognition*, American Chemical Society, 1993, ISBN 0-8412-2728-4, Chapter 13, pp. 197-226. Additional fluorescence sensing technologies and methods of value in incorporating into the present application include time-resolved fluorescence detection and measurement techniques responsive to fluorescent polarization and anisotropy phenomena, Each of the two above optical detection arrangements involve emission of light, but optical-based detection can also leverage absorption of light, for example employing colorimetry and photospectroscopy. One important example of this is Enzyme-Linked Immunosorbent Assay (ELISA) technologies that employ enzymes (as well as antibodies or other selectively responsive agents) to invoke visual color changes responsive to the presence of a target material. An example specialized product area employing these is the ArrayTube™ technology comprising a vertically-oriented reaction vessel arranged with a (non-fluorescent) colorimetric array at the vessel bottom. An example 'selection-guide' treatment comparing fluorescent, chemiluminescent, and colorimetric detection schemes and agents can be found in Selecting the Detection System—J. Gibbs, Life Sciences "Colorimetric, Fluorescent, Luminescent Methods," *ELISA Technical Bulletin—No. 5*, Corning Incorporated, 2001 (as disclosed at world wide web atcatalog2.corning.com/Lifesciences/media/pdf/elisa5.pdf, visited 01/27/13). Analogous to the fluorophore, the moiety responsible for the color of a molecule is called a chromophore.

A great many fluorophores and chromophores are permanently active (albeit modulated by solvent polarity, pH, temperature, etc.) and do not change their emission or absorption properties as a result of any binding event. Such markers simply tag molecules such as enzymes and antibodies and variations in emission or absorption properties of the sample or parts of the sample result from changes in spatial concentration of enzymes, antibodies, etc. as they cluster in their binding within localized regions of antigen. Other fluorophores and chromophores are or can be configured to change their light emission/absorption properties in direct response to binding events—for example as with calcium markers. Addition performance considerations can be considered, for example whether the fluorophores and chromophores are intrinsic or extrinsic as considered in T. Bell et al., "Intrinsic Chromophores and Fluorophores in Synthetic Molecular Receptors," in *Fluorescent Chemosensors for Ion and Molecule Recognition*, American Chemical Society, 1993, ISBN 0-8412-2728-4, Chapter 7, pp. 85-103. Related techniques of value to the present application include fluorescent probes that indirectly sense analytes via chemical reactions, for example but not limited to "turn-on" fluorescent probes discussed for example in M. Jun, B. Roy, K. Ahn, "Turn-on fluorescent sensing with reactive probes," Chem. Commun., 2011, Issue 47, pp. 7583-7601.

DNA-oriented microarrays (also called "DNA chips" and "biochips") comprise small DNA regions arranged in an array on a plate material, and are used to simultaneously measure gene expression levels of many samples or tests in parallel, genotyping of genome regions, etc. employing fluorophores, chemiluminescent, or other types of labels or tags.

Protein-oriented microarrays employing fluorophores are widely used for identification, characterization, and study of disease biomarkers, protein-protein interactions, specificity of DNA-binding and protein variants, immune response, etc. These methodologies provide an important contemporary tool for next-generation understanding of cell biology, disease, and drug development as explained, for example, in C. Wu, (ed.), *Protein Microarray for Disease Analysis: Methods and Protocols,* 2011, ISBN 1617790427, or in the handbook provided by Amersham Biosciences entitled *Fluorescence Imaging: Principles and Methods,* 2002 (document 63-0035-28 Rev.AB, 2002-10, as disclosed at world wide web at cancer.duke.edu/DNA/docs/Phosphorimaging%20_%20Fluorescent_Scanning/Fluorescence%20Imaging%20Handbook.pdf, visited Jan. 26, 2013). In addition to their use in biochemical samples, they can also be used in living cells to monitor cell metabolism and cell signaling, for example as with "Fluo-Calcium" indicators and in the techniques described in R. Wombacher, V. Cornish, "Chemical tags: applications in live cell fluorescence imaging" *J. Biophotonics* 4, No. 6, pp. 391-402 (2011).

Accordingly, the present application can leverage adaptations of this technology base so as to provide support for applications involving measure gene expression levels of many samples or tests in parallel, genotyping, next generation understanding of cell biology, disease, and drug development. Of relevance to the adaptations made in the present application to be described is that the ranges of light wavelengths for excitation emission are those of commercially manufactured Light Emitting Diodes (LEDs), and, as explained, that LEDs of differing emission wavelengths can be used as wavelength-selective detectors as taught in Pending U.S. patent application Ser. No. 13/761,142.

Recognition by Antibody, Synthetic Antibody, and Related Materials

As alternatives to animal-produced antibodies, various embodiments also provide for recognition by antibody, synthetic antibody, and related materials as taught in Pending U.S. patent application Ser. No. 13/761,142

Recognition by Molecular Imprinting Materials (MIMs)

As described above, biochemical materials and approaches that can be employed as alternatives to animal-produced antibodies for sensors used in the present application include synthetic and recombinant antibodies, recombinant antibody fragments, synbodies and unstructured peptides. In contrast to all of these, Molecularly Imprinted Material (MIM) technologies, such as Molecularly Imprinted Polymers (MIPs), leverage synthetic materials as an alternative to antibodies in highly selective sensors. MIMs can be used to recognize and bind to a target molecule with high affinities and specificities that can rival antibodies, receptors, and enzymes.

Molecularly Imprinted Polymers (MIPs) can be inexpensively and reproducibly manufactured by polymerizing commercially available monomers in the presence of a templating molecule structurally similar to a specified target molecule. Because MIPs are heavily cross-linked, and thus cannot experience conformational rearrangement, MIPs provide far superior stability to biological antibodies, offering considerably longer shelf-life, less stringent storage requirements, and can be used with extreme pH, temperature, ionic strength, and other operating conditions outside that of most antibodies. A representative review is provided in L. Ye, K. Mosbach, "Molecular Imprinting: Synthetic Materials As Substitutes for Biological Antibodies and Receptors," *Chemistry of Materials,* 2008, 20, pp. 859-868). MIMs still fall short in matching or exceeding the specificity and cross reactivity rejection of biological antibodies, and this has been viewed as a problem in diagnostics because of higher probabilities of false positives. However, various aspects of the present application's methodology, architecture, and statistical processing approaches provided for by the present application can inherently significant diminish this concern.

As sensors relevant to the present application, one of many representative reviews and summaries regarding the use of MIMs and MIPs as selectivity agents in sensors is provided in G. Guan, B. Liu, Z. Wang, Z. Zhang "Imprinting of Molecular Recognition Sites on Nanostructures and Its Applications in Chemosensors," *Sensors,* 2008, 8, pp. 8291-8320. Of additional utility to the present application is the fact that MIMs have demonstrated robust liquid and gas chemical sensors for more than a decade (see for example F. Dickert, O. Hayden, "Molecular Imprinting in Chemical Sensing," *Trends in Analytical Chemistry, vol.* 18, no. 3, 1999).

Recognition by Other Recognition Materials

Many other types of selective detection materials can be used by the present application, including peptides, genetically engineered proteins, carbohydrates, nucleic acids, oligonucleotides, amtamers, phages, and even living cells and tissues cultured from plants and animals. A representative survey of such additional types of selective detection materials that can be employed by the present application can be found in the extensive book M. Zourob, (ed.), *Recognition Receptors in Sensors*, Springer, 2010, ISBN 978-1-4419-0918-3.

Various embodiments can employ several component core, design, and fabrication technologies including:
  Organic semiconducting and conducting polymers,
  Printed electronics and functional printing,
  Microfluidic systems and their fabrication,
  A range of currently experimental sensor technologies that have been or can be adapted for microfluidic use,
  Rapidly-advancing commercial production of a wide ranges of highly selective antibodies and enzymes,
  Laboratory methods and analysis, together with associated biochemistry, for pathogen detection,
  Reconfigurable microprocessor-controlled Lab-on-a-Chip (RLoC) technologies (U.S. patent application Ser. Nos. 11/946,678 and 13/314,170),
  Microfluidic chemical bus technologies (U.S. Pat. No. 8,032,258 and pending U.S. patent application Ser. Nos. 13/251,286 and 13/251,288),
  Microfluidic and Lab-on-a-Chip development technologies (U.S. patent application Ser. Nos. 12/328,726 and 12/328,713).

Figure 18:
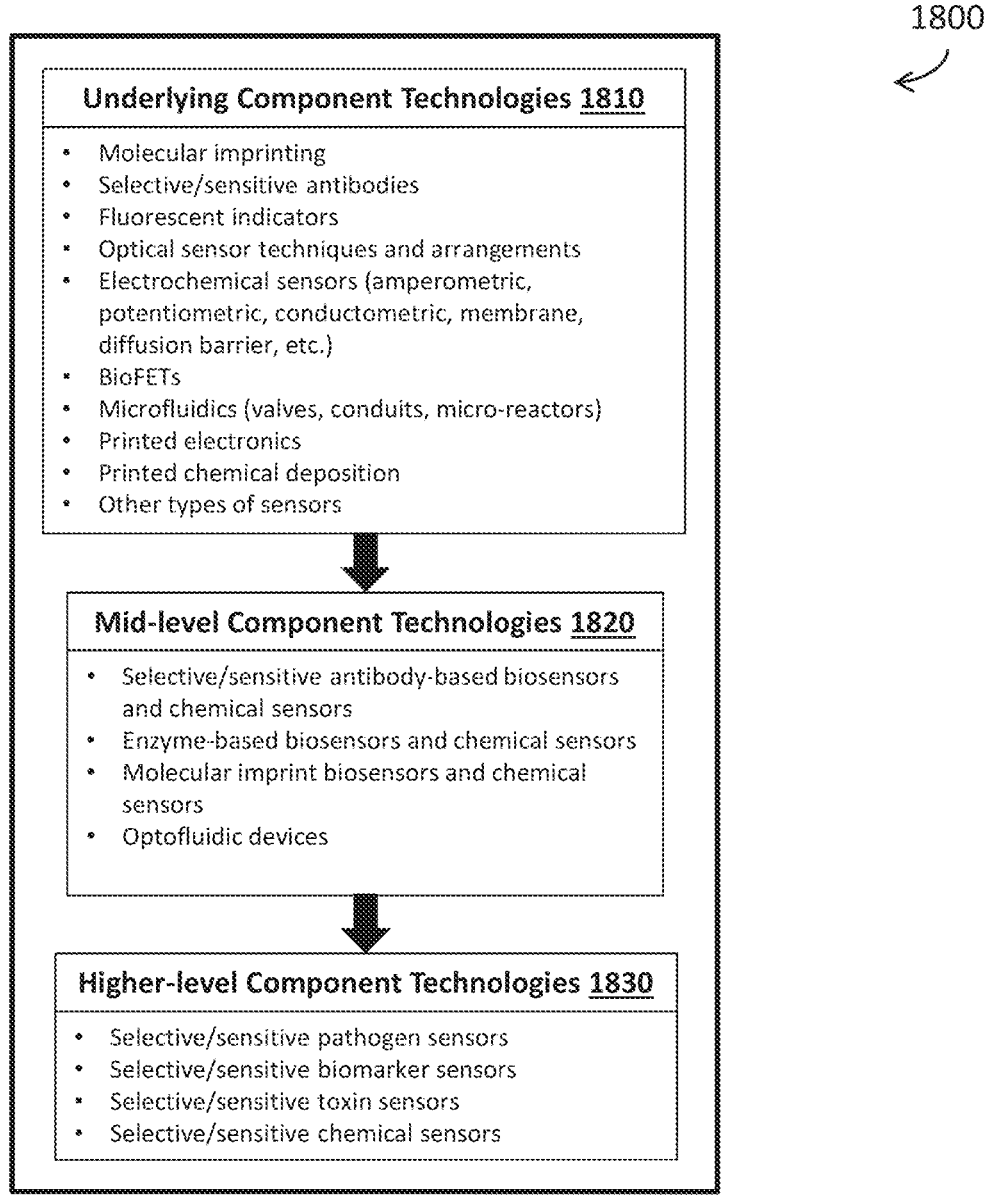
FIG. 18 depicts a representation of new and adapted individual component technologies provided for by various embodiments.

FIG. 18 illustrates a system 1800 employing underlying component technologies 1810 such as:
  Molecular imprinting,
  Selective/sensitive antibodies,
  Fluorescent indicators,
  Optical sensor techniques and arrangements,
  Electrochemical sensors (amperometric, potentiometric, conductometric, membrane, diffusion barrier, etc.),
  BioFETs,
  Microfluidics (valves, conduits, microreactors),
  Printed electronics,
  Printed chemical deposition,
  Other types of sensors, and mid-level component technologies 1820 such as:
  Selective/sensitive antibody-based sensors and chemical sensors,
  Enzyme-based sensors and chemical sensors,
  Molecular imprint sensors and chemical sensors,
  Optofluidic devices,
and higher-level component technologies 1830 such as:
  Selective/sensitive pathogen sensors,
  Selective/sensitive biomarker sensors,
  Selective/sensitive toxin sensors,
  Selective/sensitive chemical sensors.

Overall Architecture

By unifying the sensor implementation, fluidic/gas interfacing, miniaturizing approaches, electrical interfaces and optical interfaces, and further by co-locating, and integrating a large number highly-selective sensors and chemical sensors—together with appropriately selected supplemental sensors (for example temperature, pH, selective ions, etc.)—various embodiments can be configured to provide a rich ability to flexibly perform, create, deploy, maintain, and update a wide range of panels, assay, array, and/or sequence of tests for a wide range of substances and pathogens.

Figure 19:
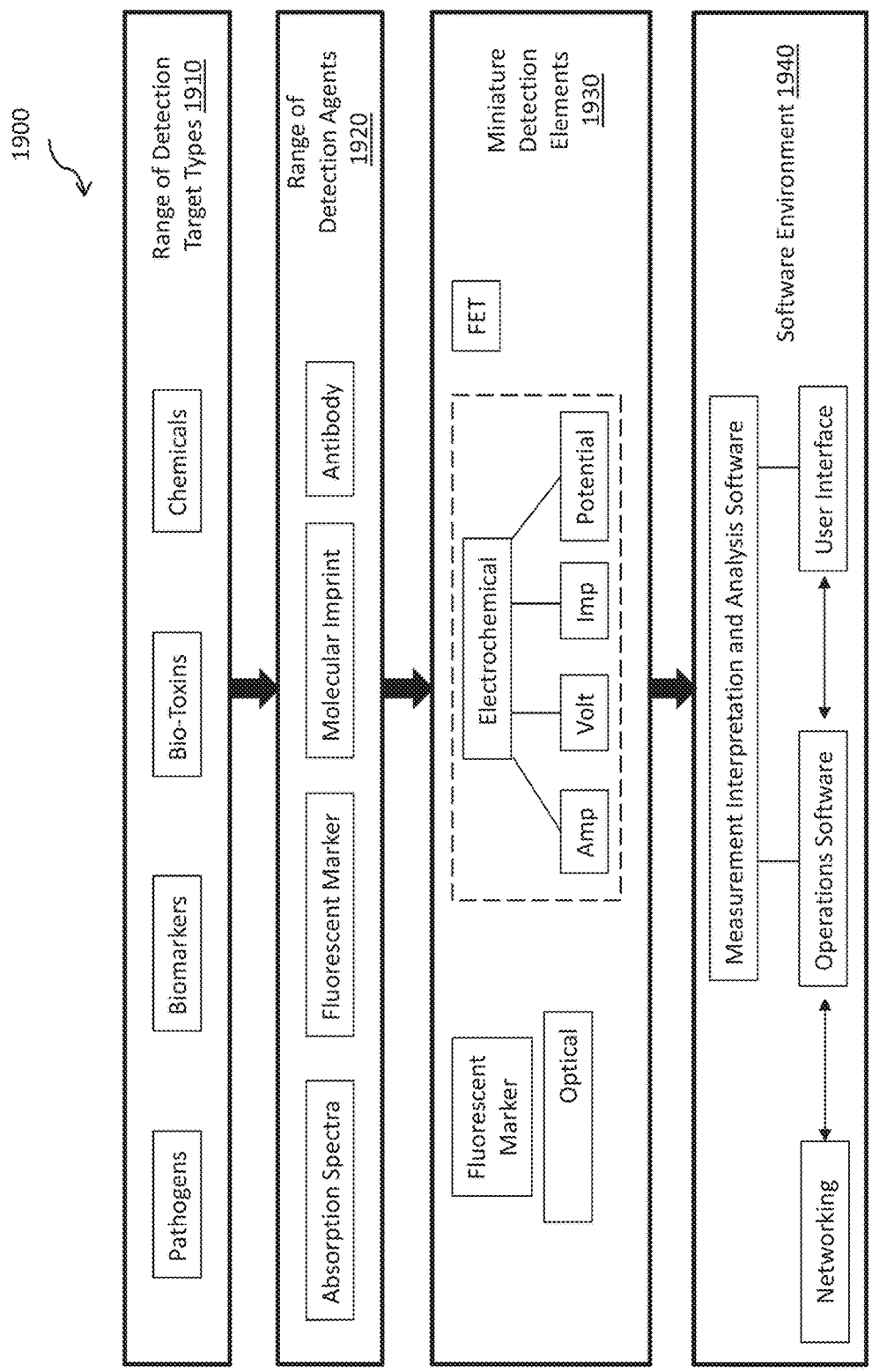
FIG. 19 depicts an adaptive framework provided and performed by embodiments of the present application so as to create a flexible multiple-purpose platform technology.

As to implementing the platform in a universal context to a wide range of applications, FIG. 19 depicts an example representation of the synergistic and adaptive framework 1900 to create a flexible multiple-purpose cell incubation platform technology with vastly expanded capabilities. Framework 1900 includes a range of detection target types 1910, such as pathogens, biomarkers, bio-toxins, and chemicals. Framework 1900 includes a range of detection agents 1920, such as absorption spectra, fluorescent marker, molecular imprint and anti-bodies. Framework 1900 includes a range of miniature detection elements 1930, such as electrochemical detection elements, optical elements, FETs, and fluorescent markers. Framework 1900 includes a computing environment 1940 (e.g., a software environment) for controlling, analyzing, reporting, networking and for providing a user interface.

Figure 20:
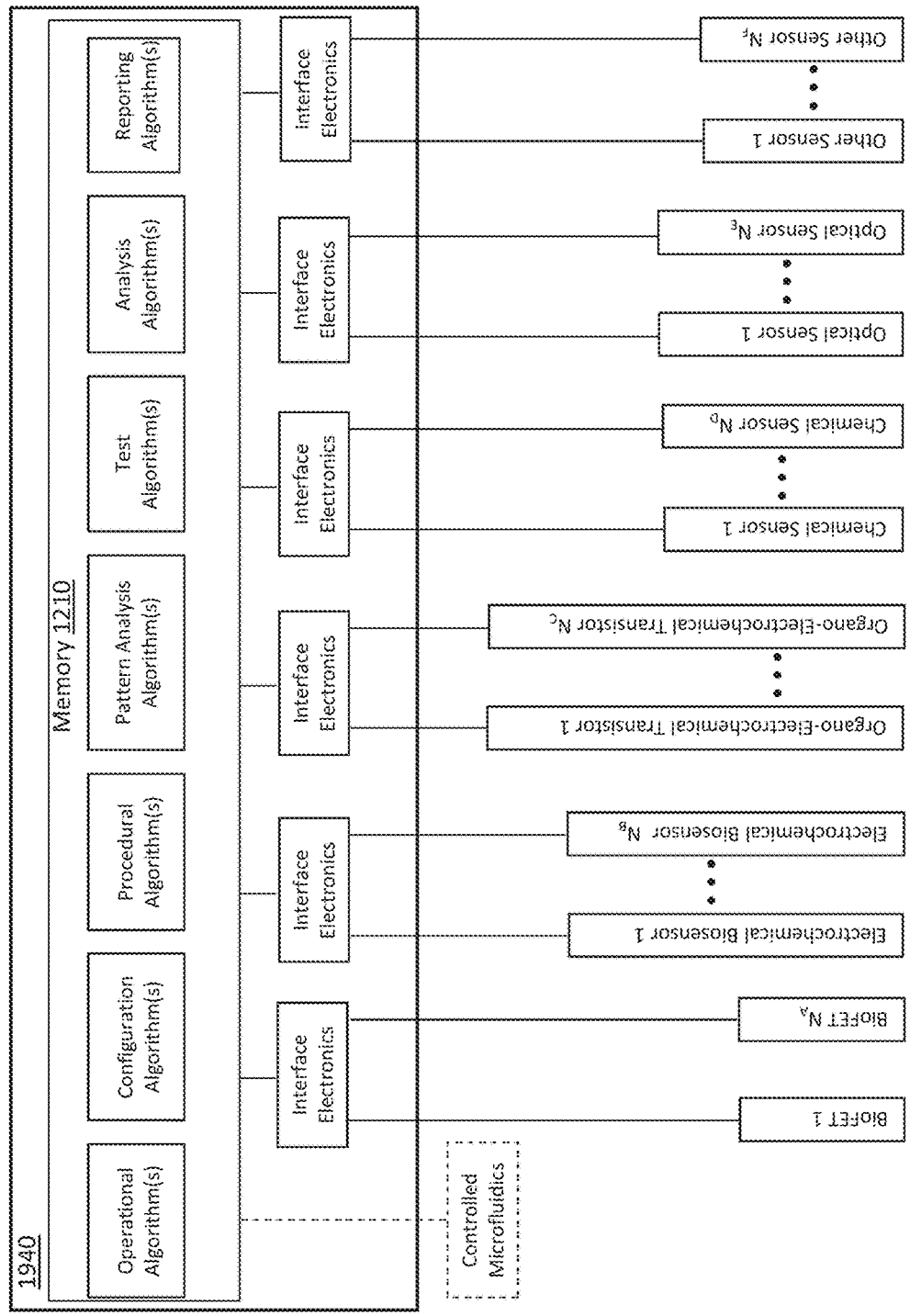
FIG. 20 depicts an overall overview of the software, signal input hardware, signal processing hardware, and software-control hardware provided for or implemented in various embodiments of the present application.

FIG. 20 depicts an overall overview of computing environment 1940 according to some embodiments. Computing environment 1940 may include software, signal input hardware, signal processing hardware, and software-control hardware, and may contain a memory 2010 to store one or more of: operational algorithms, configuration algorithms, procedural algorithms, pattern analysis algorithms, test algorithms, analysis algorithms and reporting algorithms. Computing environment 1940 may further include one or processors to execute the one or more algorithms stored in memory 2010. Computing environment 1940 further includes interface electronics to interface with one or more sensors, such as BioFET Sensors, electrochemical sensors, OECT sensors, chemical sensors, optical sensors, etc.

In FIG. 20 the software is depicted at the top (signifying the software is oriented as being closer to the user), while the signal, sensor, and fluidic hardware is in the lower portion of the figure (signifying these are oriented as being closer to the analyte being analyzed).

Technologies and materials applicable to embodiments of the present application will continue to evolve over time. Accordingly employing the approaches taught throughout, various embodiments can be structured to anticipate a wide range of evolutions and development in technology, techniques, protocols, usage, and applications.

Updatable software is one easily-met aspect of this goal that can be readily incorporated, but updating of sensors, reagents, and other aspects is far more challenging.

Removable Replaceable Media Element Approach to Microplates Comprising Sensors According to some embodiments, printed-sensing removable replaceable media element approach taught in Pending U.S. patent application Ser. No. 13/761,142 can be applied to microplates comprising sensors.

Various embodiments provide a removable, practical, inexpensively manufactured replaceable medium providing wells for isolated cell incubation that can include a wide spectrum of low-cost sensors and reagents and memory for software. The removable medium approach provides opportunities to address a number of other issues including life-cycle and disposal, and the broader system design readily facilitates extensions into a wide range of broader applications immediately spanning into health care and industrial applications.

On the logistics side, there will always be new types of testing methodologies and improvements that are difficult if not completely impossible to predict. Although software changes to address aspects of this degree of variability and uncertainty can be provided by various methods, the variability of the types of physical sensors and associated testing reagents necessary requires some way of physically updating at least some aspects of a testing device. Further, at least some of the sensors employed will have limited lifetimes (for example, antibodies and enzymes could degrade) and be subject to contamination after one or more uses.

Additionally, the removable replaceable media element can include at least reagents.

Additionally, the removable replaceable media element can include serial numbers, sensor specifications, and perhaps software.

The removable replaceable media further can provide an open architecture for both third party innovation and an evolution ability. Such an open architecture allows for third-party development that can address a wider range and greater number of markets (both large and small). Further, the open architecture also allows for easy incorporation of sensor technology improvements, and also increases the opportunity for improved and simplified operation by users of such devices.

The technical features, value proposition, and market considerations both give rise to and require inexpensive mass manufacturing and distribution. These in turn give rise to the need for the removable replaceable medium to comprise inexpensive materials that are straightforwardly and inexpensively assembled. An initial solution to this is to:

Use an inexpensive substrate for the removable replaceable medium such as some type of polymer or plastic. In various implementations, the substrate can be rigid or can be flexible.

Employ functional printing (such as inkjet-printed functional polymers deposited directly onto the inexpensive substrate) for manufacturing the sensors and electrical aspects:
  Printed electrodes (using organic polymer conductors)
  Printed sensors (comprising insoluble and/or protected layers of semiconducting polymers, materials comprising enzymes/antibodies, deposition layers of enzymes/antibodies, etc.)
  Printed transistors (comprising layers of semiconducting polymers and organic polymer conductors) for electronics.

Employ functional printing for manufacturing of reagent reservoirs (for example in the form of depositions soluble solids or gels)

Employ functional printing for manufacturing of Read-Only Memory ("ROM") (for example in the form of printed optical codes such as printed optical bar codes, printed optical matrix codes, printed holographic codes, printed magnetic code stripe, printed electronic data memory, etc.)

If optical sensing is used, the inexpensive substrate could be, for example:
  Engineered to transparent for light pass-through at the needed wavelengths, and/or
  Employ functional printing of a optically reflective layer (reflective at the needed wavelengths)

Further, the removable replaceable medium element and its contents can be designed and configured to facilitate recycling, bio-hazard neutralization and/or controllable degradation facilitated by a "termination solvent" degradation-initiation fluid, etc. In some embodiments, the removable replaceable medium element comprises an array of sensors on a substrate. In another embodiment of the present application, the removable replaceable medium element additionally comprises electrical conductors. In another aspect of the present application, the removable replaceable medium element additionally comprises sensor interface electronics.

In some embodiments, the removable replaceable medium element additionally comprises data storage ROM.

In some embodiments, the removable replaceable medium element additionally comprises read/write data storage.

In some embodiments, the removable replaceable medium element additionally comprises deposits of at least one reagent.

In some embodiments, the removable replaceable medium element comprises passive fluidics for transport of one or more liquids, gases, suspensions, slurries, etc.

In some embodiments, the removable replaceable medium element comprises fluidics elements forming at least part of a valve for controlling the flow of one or more of liquids, gases, suspensions, slurries, etc.

In some embodiments, the removable replaceable medium element comprises fluidics elements forming at least part of a pump inducing the flow of one or more of liquids, gases, suspensions, slurries, etc.

Figure 21:
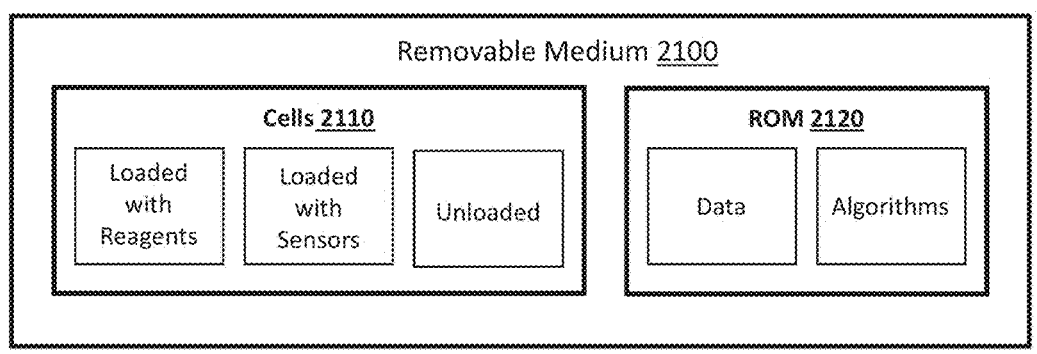
FIG. 21 depicts an example abstract representation of a removable replaceable media element.

FIG. 21 depicts an example abstract representation of a removable replaceable media element 2100 comprising a plurality of cells 2110, which may be loaded with reagents, loaded with sensors or unloaded. Removable media element 2100 further includes a memory 2120, such as Rom, to store data and one or more algorithms.

Figure 22A:
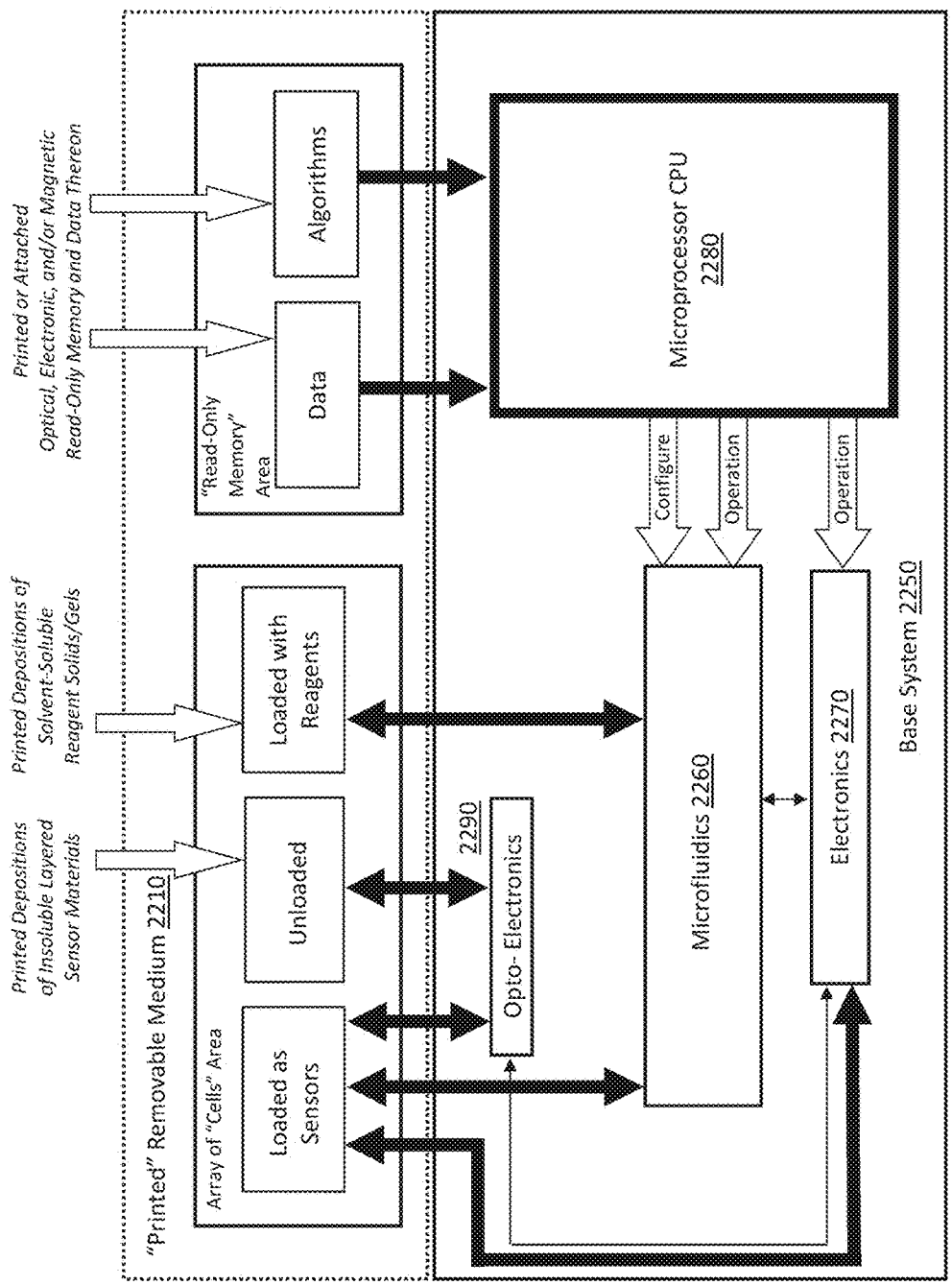
FIG. 22a depicts an embodiment of a system comprising a removable replaceable media element in communication with a base unit.

FIG. 22a illustrates a system 2200 comprising a removable element 2210 that is configured to fit inside or attach to a base unit 2250 comprising at least microfluidics 2260, a microprocessor 2280, various electronics 2270, opto-electronics 2290 for optical sensing, and sample acquisition arrangements (as well as power sources, housing, EMI shielding, fluid reservoir(s), any user-operated controls, network interfaces, computer interfaces, visual display elements, etc.).

Figure 22B:
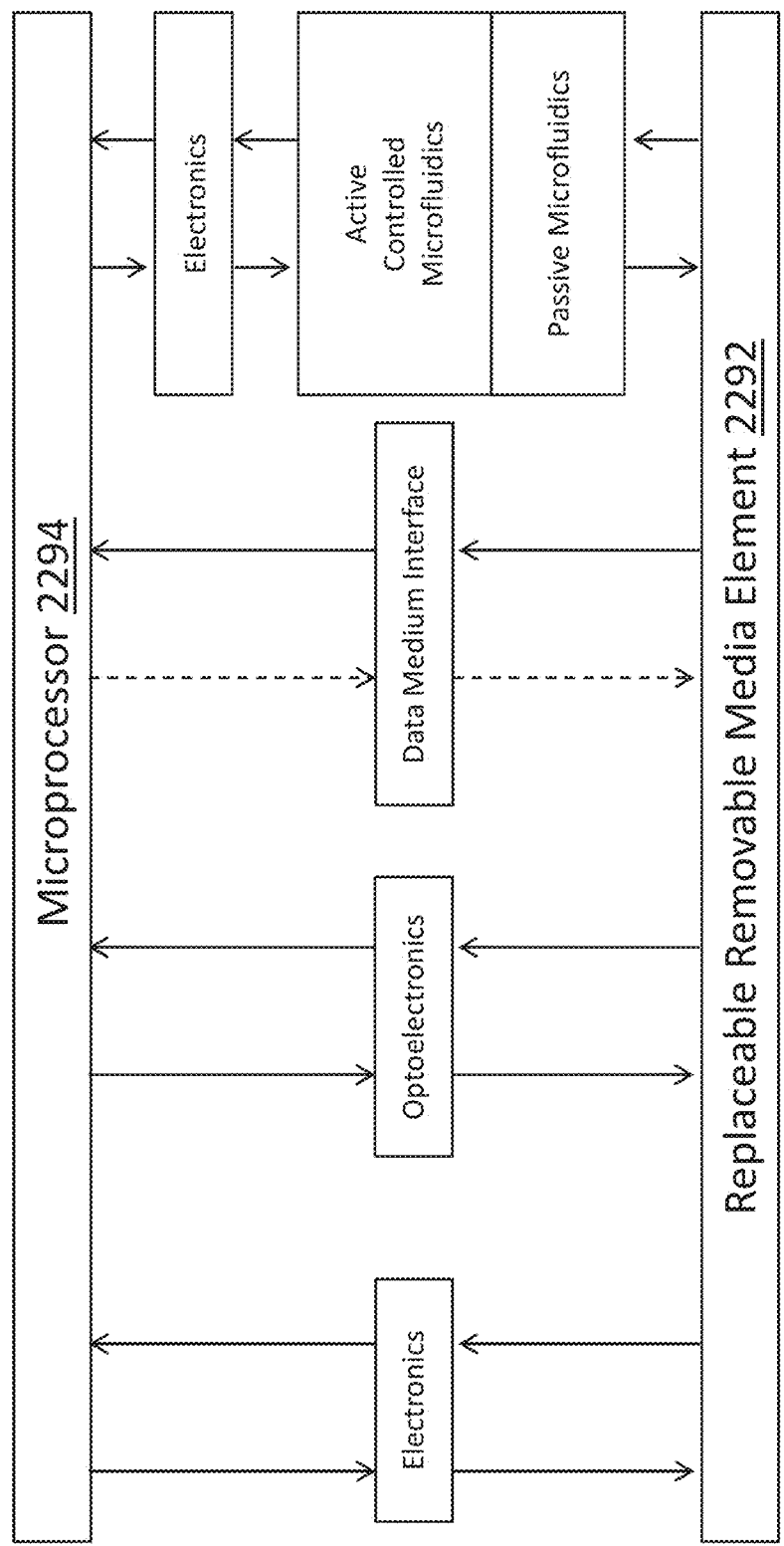
FIG. 22b depicts a simple high-level combined signal-flow and fluidic-flow representation of a system comprising a removable replaceable media element in communication with a base unit.

As another example representation, FIG. 22b depicts a simplified high-level combined signal-flow and fluidic-flow representation of one example of many possible implementations of the present application. This representation emphasizes abstracted hardware and transactions with the removable element. Further details with respect to FIGS. 22a and 22b can be found at least in Pending U.S. patent application Ser. No. 13/761,142.

Figure 23A:
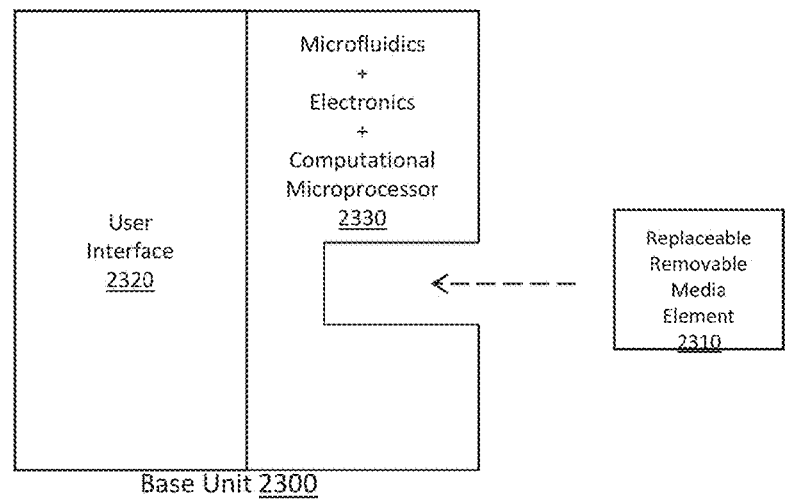
FIGS. 23a-23c depict possible user and interface implementations according to some embodiments of the present application.
Figure 23B:
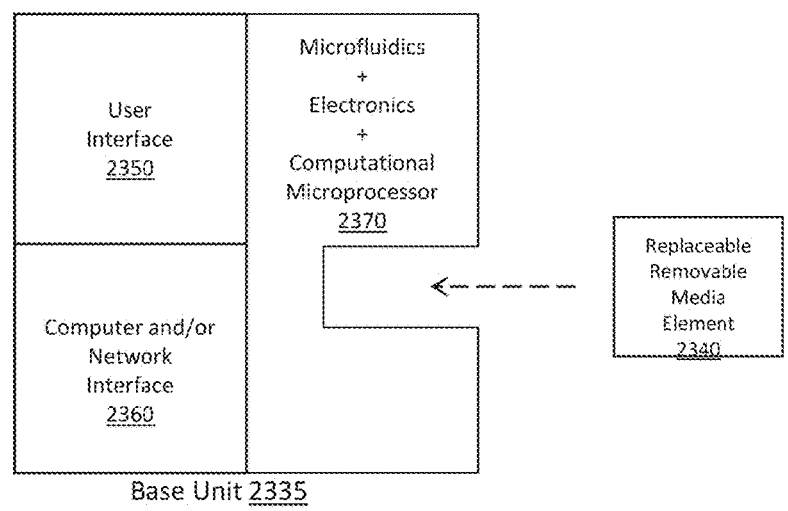
Figure 23C:
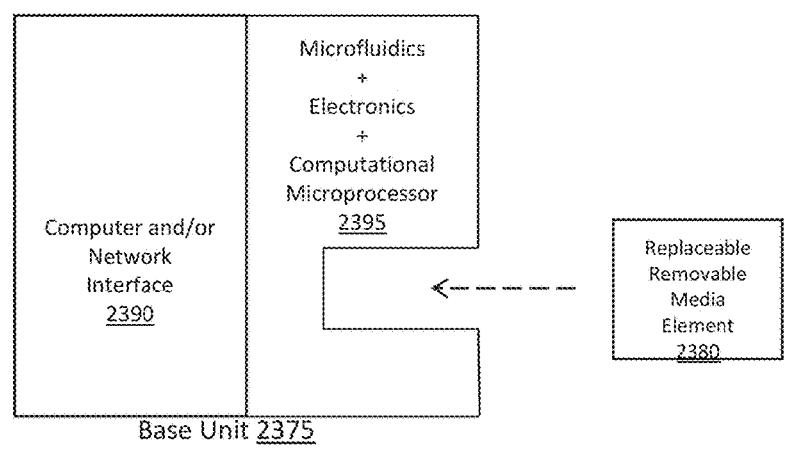

As other example embodiments, FIGS. 23a-23c depicts simple high-level representations of examples of systems that provide many possible user experience and interface implementations. Each system comprises a base unit that is implemented so as to accept and support at least, but often more than one, removable replaceable media element.

For example, FIG. 23a depicts an arrangement that comprises base system comprising an internal user interface 2320 and other structures 2330, such as microfluidics, electronics and computational microprocessor. Internal user interface 2320 can comprise, for example software, user-operated controls, visual display elements, etc. Replaceable removable media element 2310 is adapted to couple with base system, as illustrated in FIG. 23a.

FIG. 23b depicts a variation on the example arrangement of FIG. 23a wherein either or both of a computer interface 2360 (USB, Bluetooth, IR, etc.) and/or network interface 2350 (wireless LAN, wireless WAN, cellular, cabled-LAN, telephone land-line, etc.) is also provided. FIG. 23c depicts a variation on the example arrangement of FIG. 23b wherein either or both of a computer interface 2390 (USB, Bluetooth, IR, etc.) and/or network interface 2390 (wireless LAN, wireless WAN, cellular, cabled-LAN, telephone land-line, etc.) is also provided, but in this example there is no internal user interface. Many variations on these examples are of course possible.

Additionally, the networking capabilities provide for a wide range of practical and expansion capabilities such as (a) download of software upgrades additional algorithms, and databases, (b) remote operation, (c) accessing more powerful computing for more complex data analysis, (d) interconnecting embodiments of the present application with lab equipment, (e) interconnecting at least the computing environments of two or more instances of embodiments of the present application so that they can collectively act as a single larger unit in various ways, (f) remote testing, as well as other functions.

FIGS. 24a-24d depict example representations of various example embodiments of the removable replaceable media elements. The examples shown here comprise example arrays of indented "wells" that can be used as isolated cell culture sites along with other example features.

Figure 24A:
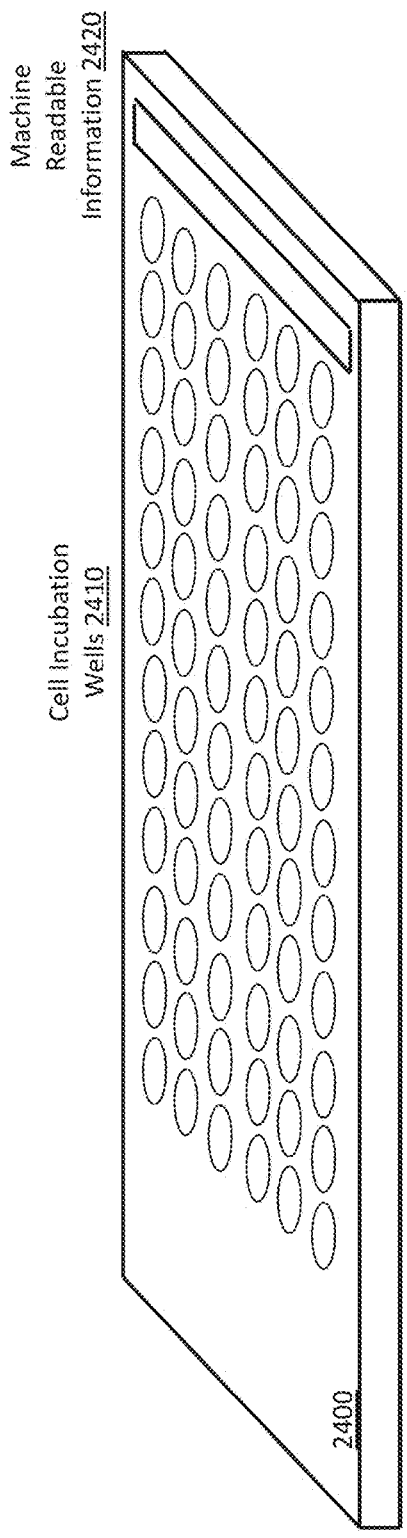
Figure 24B:
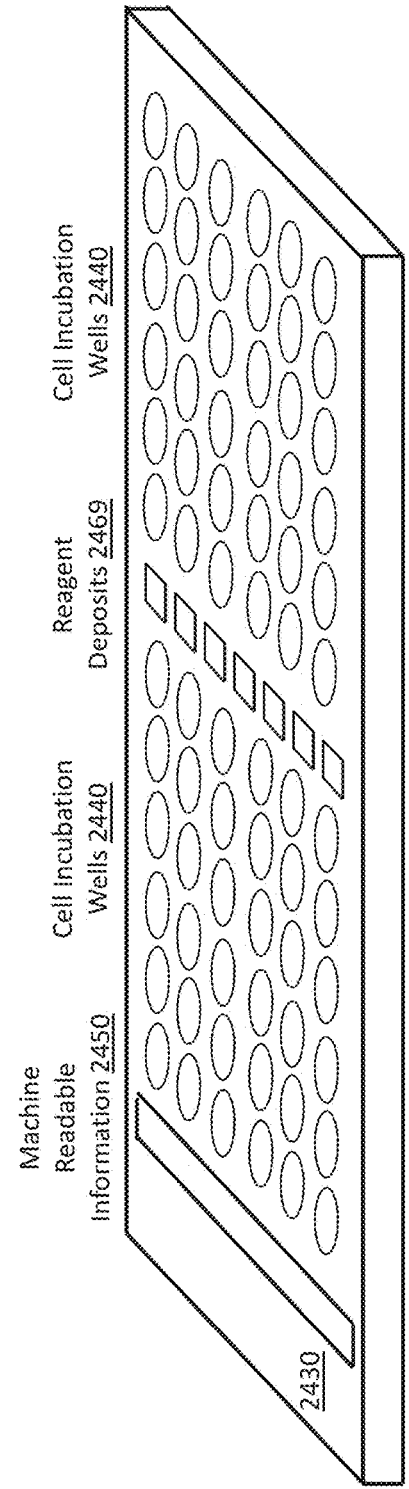
Figure 25:
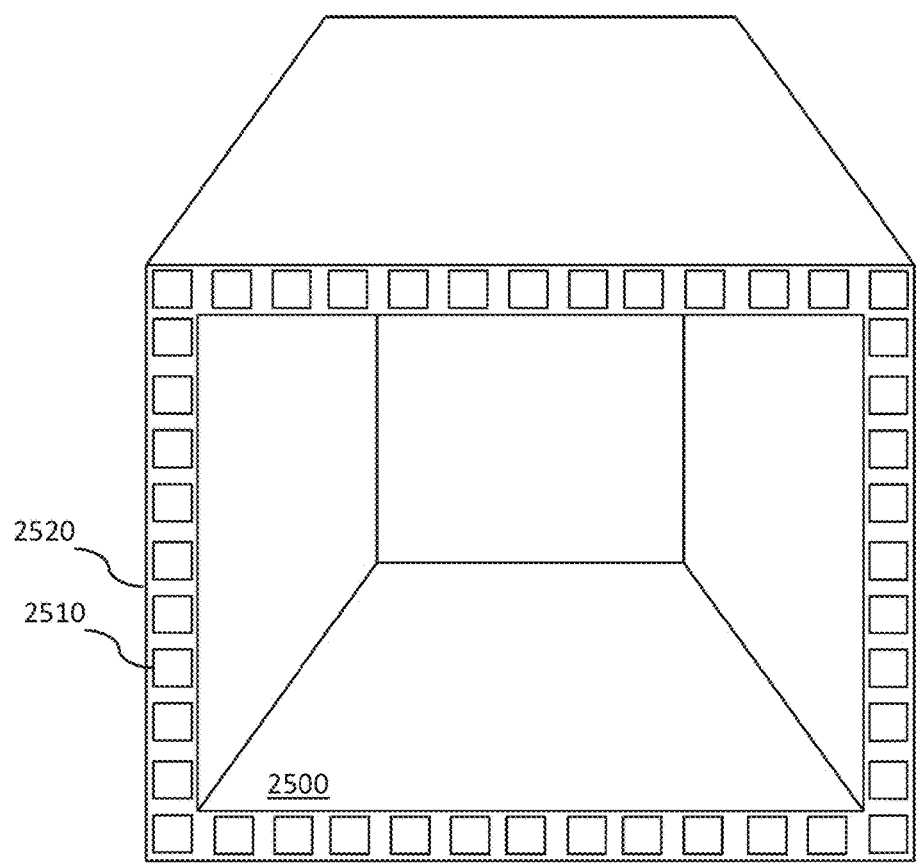
FIG. 25 depicts an example representation of the offset bottom view of a "cap" that meets and covers each site on the removable replaceable media element with a fluid-tight seal.

FIG. 24a illustrates a microplate 2400 with cell incubation wells 2410 and a region of machine readable information 2420. FIG. 24b illustrates a microplate 2430 with cell incubation wells 2440, a region of machine readable information 2450 and a region for reagent deposits 2460. FIGS. 24c-24d include depictions of regions of electrical interface elements. FIG. 24c illustrates a microplate 2470 with cell incubation wells 2472, a region of machine readable information 2474 and a region for electrical interface 2478. FIG. 24d illustrates a microplate 2480 with cell incubation wells 2482, a region of machine readable information 2484 and a region for electrical and optical interface 2488. FIG. 25 illustrates electrical interface elements 2510 provided at each well 2500 (and in some cases, reagent deposition site) and interface directly with a cap 2520. Many other combinations are possible and are anticipated for various embodiments.

It is noted that the example arrangements depicted in FIGS. 24a-24d utilize circular shapes for indented wells and rectangular shapes of the regions of machine readable information. Further, the example arrangements depicted in FIGS. 24b-24d and FIG. 25 employ rectangular shapes for reagent deposits, electrical interface elements, and optical interface elements. However, these shape choices are merely examples and other shapes (for example hexagonal, rhomboidal, trapezoidal, etc.) can be used as found to be advantageous.

In some electrical sensing arrangements (such as has been described earlier), the removable replaceable media element can further comprise additional electrical elements including but not limited to electrical shielding, diodes, transistors, resistors, capacitors, inductors, ferrites, electronic circuitry, etc. as well as materials suitably conductive, insulating, etc.

In some optical sensing arrangements (as will be described later), the well and removable replaceable media element can further comprise optical elements including but not limited to LEDs, photodiodes, phototransistors, etc. as well as materials suitably opaque, transparent, or translucent at specific wavelengths of electromagnetic radiation, etc.

Machine Readable Information Provided by the Removable Replaceable Media Element Machine Readable Information provided by the removable replaceable can include data and/or algorithms and can take the physical form of printed optical codes (such as printed optical bar codes, printed optical matrix codes, printed holographic codes), printed magnetic code stripe, printed electronic data memory, etc.).

In an embodiment, the machine readable information provided by the removable replaceable media element is printed on the removable replaceable media element.

In another embodiment, the machine readable information provided by the removable replaceable media element is comprised by a machine readable medium such as a separately manufactured label attached to the removable replaceable media element by a melding, adhering, or other attachment method or process.

In an embodiment, the machine readable information provided by the removable replaceable media element comprises date information associated with the materials on the removable replaceable media element.

In an embodiment, the machine readable information provided by the removable replaceable media element comprises serial number information.

In an embodiment, the machine readable information provided by the removable replaceable media element comprises information describing the included sensor configuration.

In an embodiment, the machine readable information provided by the removable replaceable media element comprises information relating the included sensor operation.

In an embodiment, the machine readable information provided by the removable replaceable media element comprises information specifying parameters used by at least one algorithm.

In an embodiment, the machine readable information provided by the removable replaceable media element comprises information specifying at least one algorithm.

The interface and reading of the machine readable medium by the base unit will be discussed with reference to FIGS. 30a-c.

Sensors Provided by the Microplate Removable Replaceable Media Element, Sensor Fabrication Via Printing, and Associated Printed Electronics As described earlier and taught in Pending U.S. patent application Ser. No. 13/761,142, a wide variety of sensors, organic electronic sensors, and other printed devices relevant to the removable replaceable medium element aspects of the present application can be created through a layered implementation oriented in a manner suitable for printing.

Figure 26A:
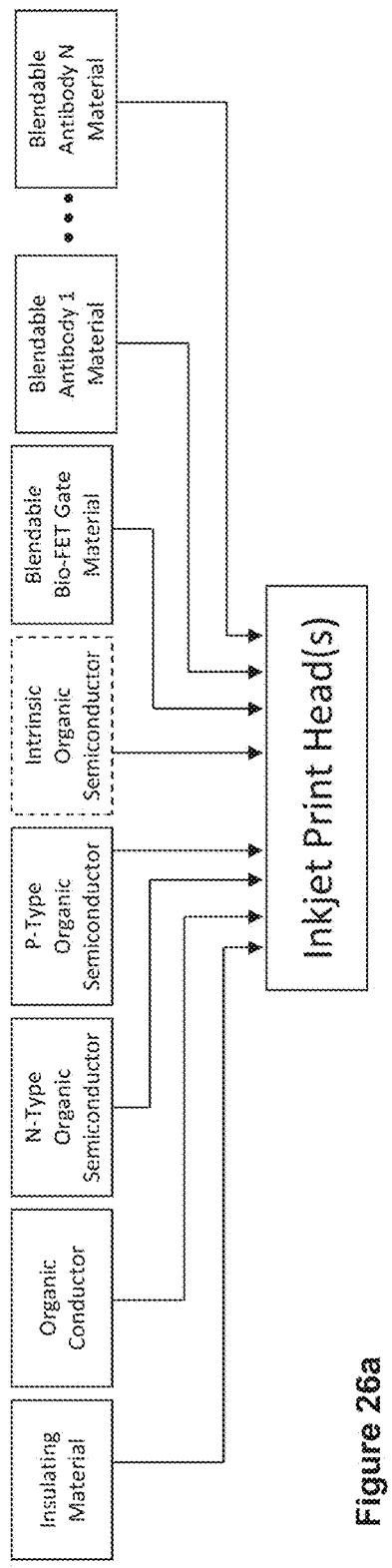
FIGS. 26a-26b depict representations of example functional printed methods that can be used to print the sensors on the removable replaceable medium.
Figure 26B:
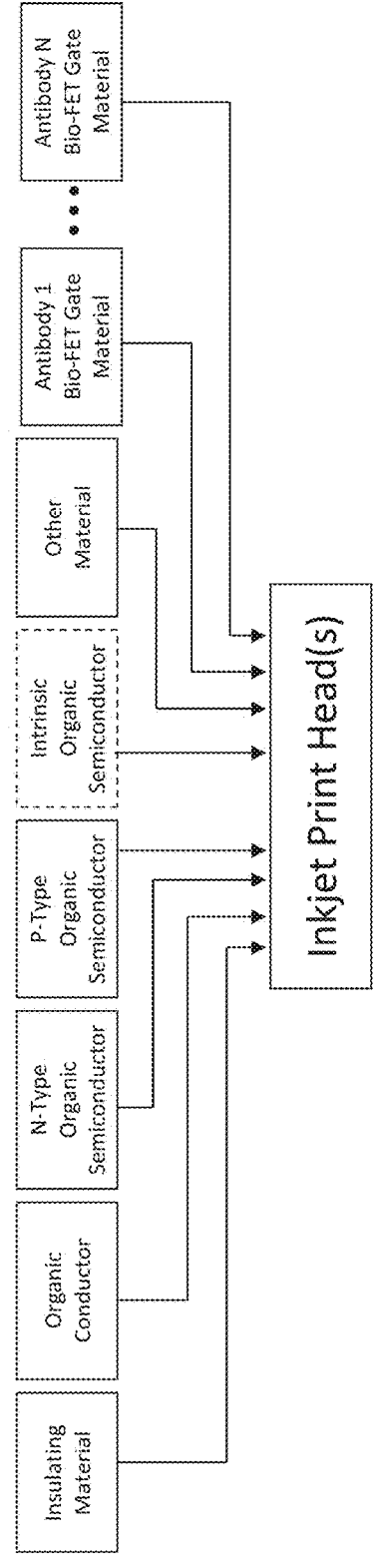

FIGS. 26a-26b depict representations of example functional printed methods that can be used, for example, to print the sensors on the removable replaceable medium. For example, functional printing can be implemented by rendering precision-controlled depositions of one or more types of fluid "inks" onto a surface. Here the "inks" can comprise one or more of various types of electrical organic conductors, organic insulators, organic semiconductors, reflective materials, antibodies, enzymes, colloidal substances, metamaterials, etc. Such "inks" can dry, polymerize, can be "cured," etc., after deposition by employing various types of drying, heating, evaporating-time pause, vacuum aspiration, photo-activation, and/or other processes. The "inks" can be applied in layers to create layered structures comprising different materials and well-defined interfaces between them. In some arrangements, the inks can be blended in the printing (or other deposition) action. The inks must permit specified functions to properly occur (for example proper immobilization of biologically active materials, electrical conduction, charge carrier injection, etc,), have proper electrical, thermal, and mechanical characteristics, and be non-soluble in the fluids used to carry the analyte.

Alternative Use of Silicon Semiconductors and Semiconductor Devices

Although printed semiconductor devices such as field effect transistor arrangements suitable for subsequent printing of a layer of selective detection material are expected to become straightforwardly fabricated with optimized materials at low cost with high levels of performance, at the moment traditional silicon semiconductors typically offer higher performance, for example due to carrier mobility issues in organic semiconductors. Accordingly, the present application provides for the use of silicon semiconductors and semiconductor devices.

As a first example, silicon-based semiconducting field effect transistor structures with an exposed insulated gate (the insulated gate subsequently metalized or not, depending on the design of the sensor at the particular site) can be surface mounted on the removable replaceable medium element, and printing of a layer of selective detection material on the exposed gate (or metalized gate contact) can be performed. In this case, the removable replaceable medium element is not itself a silicon wafer, other sensor sites can be freely fabricated by printing of electrodes, organic field effect transistors, etc., and deposited materials such as reagents can be freely fabricated by printing or other deposition processes in other regions of the removable replaceable medium element.

As a second example, such silicon-based semiconducting field effect transistor structures can be surface mounted on every sensor site of the removable replaceable medium element, and printing of a layer of selective detection material on the exposed gate (or metalized gate contact) can be performed. In this case, the removable replaceable medium element is again not itself a silicon wafer, and deposited materials such as reagents can be freely fabricated by printing or other deposition processes in other regions of the removable replaceable medium element.

As a third example, a plurality of such silicon-based semiconducting field effect transistor structures can be rendered and sparsely distributed on a silicon wafer or portion of a silicon wafer that is attached to the removable replaceable medium element, and printing of a layer of selective detection material on the exposed gate (or metalized gate contact) can be performed. In this case, the entire removable replaceable medium element is not a silicon wafer, other sensor sites can be freely fabricated by printing of electrodes, organic field effect transistors, etc. in other regions of the removable replaceable medium element, and deposited materials such as reagents can be freely fabricated by printing or other deposition processes in other regions of the removable replaceable medium element.

As a fourth example, a plurality of such silicon-based semiconducting field effect transistor structures can be rendered and sparsely distributed on a silicon wafer or portion of a silicon wafer that comprises the entire substrate of the removable replaceable medium element, and printing of a layer of selective detection material on the exposed gate (or metalized gate contact) can be performed. In this case, the entire removable replaceable medium element is a silicon wafer, and deposited materials such as reagents can be freely fabricated by printing or other deposition processes in other regions of the removable replaceable medium element.

As a fifth example, the above fourth example, additionally one or more regions of electrodes are provided on the silicon wafer, either in a silicon wafer step or but subsequent printing of conductive material, and other sensor sites can be freely fabricated by printing of organic field effect transistors, etc. in these "electrode only" regions of the removable replaceable medium element, and deposited materials such as reagents can be freely fabricated by printing or other deposition processes in other regions of the removable replaceable medium element.

Other variations are anticipated and provided for by the present application. For example, as described earlier, some electrochemical sensors can benefit from direct connection of electrochemical electrodes to a field effect transistor and can be fabricated in ways combining the above approach with those involving field effect transistors.

Electronics Interface Provided by the Removable Replaceable Media Element

In some embodiments, electrical connections for one or more sensors or sensor components at a particular well can be routed to an electrical connection region located at the associated well, surrounding the well, on at least one edge of the well, near at least one edge of the well, etc. on the removable replaceable media element, for electrical connection through electrical contacts comprised by an associated cap (for example as depicted in FIG. 25), a group of caps, or other arrangement, although many other variations are possible and provided for by the present application.

In some embodiments, electrical connections for one or more sensors or sensor components can be routed to an electrical connection region in another part of the removable replaceable media element. In some implementations, at least one electrical connection for one or more sensors or sensor components is made to an electrical shielding arrangement comprised by the removable replaceable media element. In some implementations, at least one electrical connection for one or more sensors or sensor components is made to an electrical circuit (for example, an amplifier, differential amplifier, current source, comparator, analog-to-digital converter, digital-to-analog converter, etc. the removable replaceable media element.

In some implementations, at least one electrical connection to an electrical circuit (for example, an amplifier, differential amplifier, current source, comparator, analog-to-digital converter, digital-to-analog converter, etc. on the removable replaceable media element is made to electrical connections on the removable replaceable media element arranged to electrically connect with electrical connections at the associated site, surrounding the site, on at least one edge of the site, near at least one edge of the site, etc. on the removable replaceable media element.

As described earlier, FIGS. 24c-24d include depictions of centralized regions comprising electrical interface elements. Alternatively, or in addition, electrical interface elements can be provided at each well (and in some cases, reagent deposition site).

Optical Interface Provided by the Removable Replaceable Media Element

As an alternative to a plurality of electrical contacts for carrying sensor signals from the Microplate Removable Replaceable Media Element, electronics provided within the Microplate Removable Replaceable Media Element can be used to convert the electrical signals into optical signals. Using this approach, electrical connections can be used for powering the Microplate Removable Replaceable Media Element while optical signals can be used for carrying a rich density of sensor signals. FIG. 24d includes a depiction of centralized regions comprising optical interface elements.

Various embodiments can multiplex pluralities of sensor signals into one or at least a considerably smaller number of multiplexed signals of digital or analog format.

Base Unit and its Interfacing Removable Replaceable Media Element

Various embodiments provide for interactions between the removable replaceable media element (for example, removable replaceable media element 2210 of FIG. 22a, element 2292 of FIG. 22b, and the removable replaceable media elements 2330, 2370 and 2395 of FIGS. 23a-23c) and the base unit (for example, base unit 2250 of FIG. 22a, base unit 2294 of FIG. 22b, and base units 2300, 2335 and 2375 of FIGS. 23a-23c).

Regarding sensors or sensor components on the removable replaceable media element that comprise electrical connections, each "cap" can be configured to cover an associated region of a removable replaceable media element that comprises one or more, the cap can comprise associated electrical connections for making electrical contact with corresponding electrical connection on the removable replaceable media element. The electrical connections for one or more sensors or sensor components at a particular well can be routed to an electrical connection region located at the associated well, surrounding the well, on at least one edge of the well, near at least one edge of the well, etc. on the removable replaceable media element, for electrical connection through electrical contacts comprised by an associated cap, a group of caps, or other arrangement.

In some electrical sensing arrangements (for example as taught in Pending U.S. patent application Ser. No. 13/761, 142), the cap can further comprise electrical elements including but not limited to electrical shielding, diodes, transistors, resistors, capacitors, inductors, ferrites, LEDs, photodiodes, phototransistors, electronic circuitry, etc. as well as materials suitably conductive, insulating, etc.

In some optical sensing arrangements (for example as taught in Pending U.S. patent application Ser. No. 13/761, 142), the cap can further comprise optical elements including but not limited to LEDs, photodiodes, phototransistors, etc. as well as materials suitably opaque, transparent, or translucent at specific wavelengths of electromagnetic radiation, etc.

FIG. 27a depicts an example representation showing "cap" 2700 (without illustrating fluidic ports, electrical connections, mechanical support, etc.) interfacing with a site or area 2710 within a removable replaceable media element. In some embodiments cap 2700 can be used to interface individual wells or groups of wells. In some embodiments cap 2700 can be nested in various hierarchical arrangements.

Figure 27B:
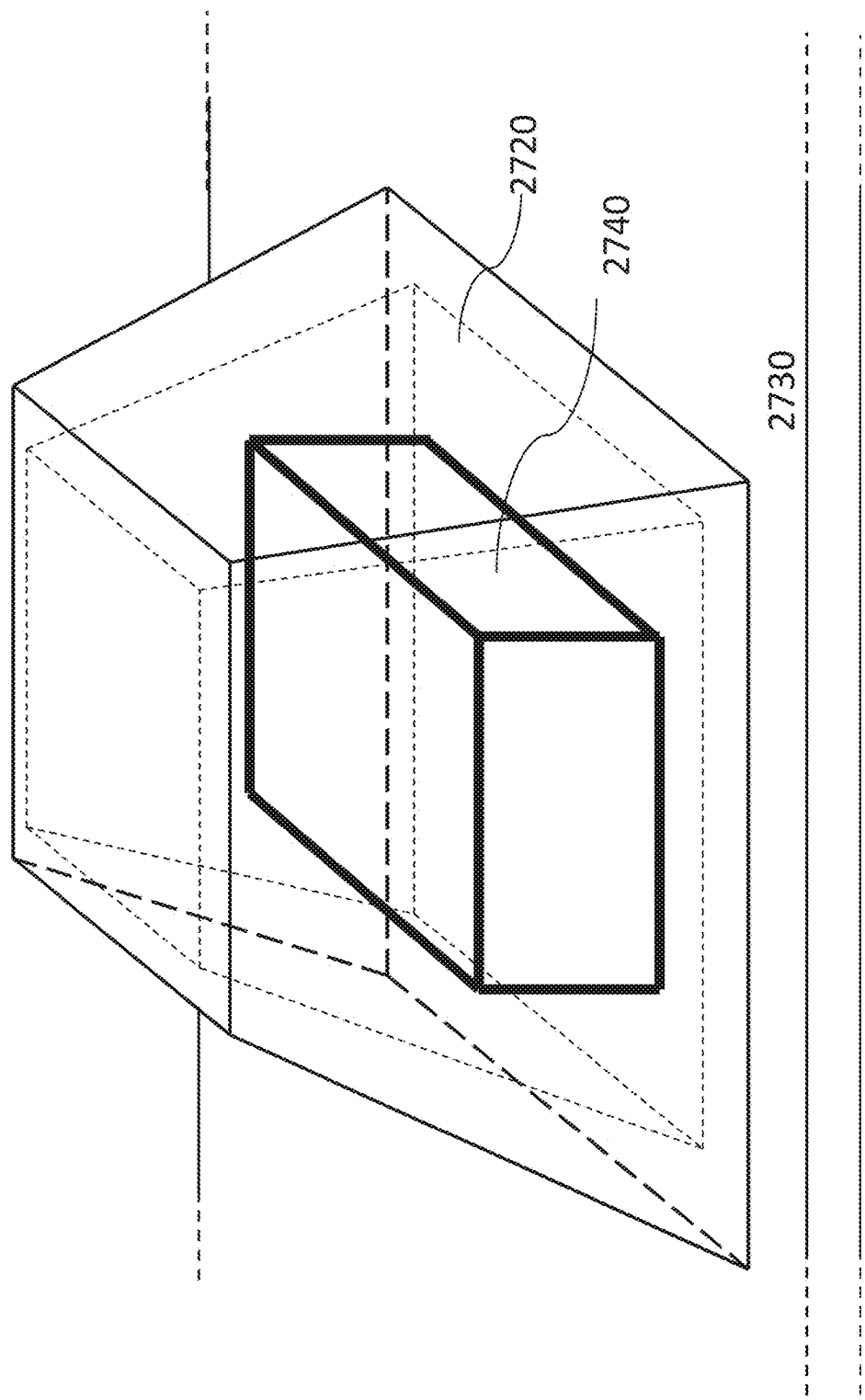
FIG. 27b depicts a cap interfacing with a site on the removable replaceable media element that comprises a printed sensor according to some embodiments.

A cap can also be used with a removable replaceable media element with sensors or sensor components. FIG. 27b depicts an example representation of cap 2720 that covers a site area 2730 within a removable replaceable element that comprises a sensor 2740 (here abstractly represented as a bold rectangular solid).

Figure 27C:
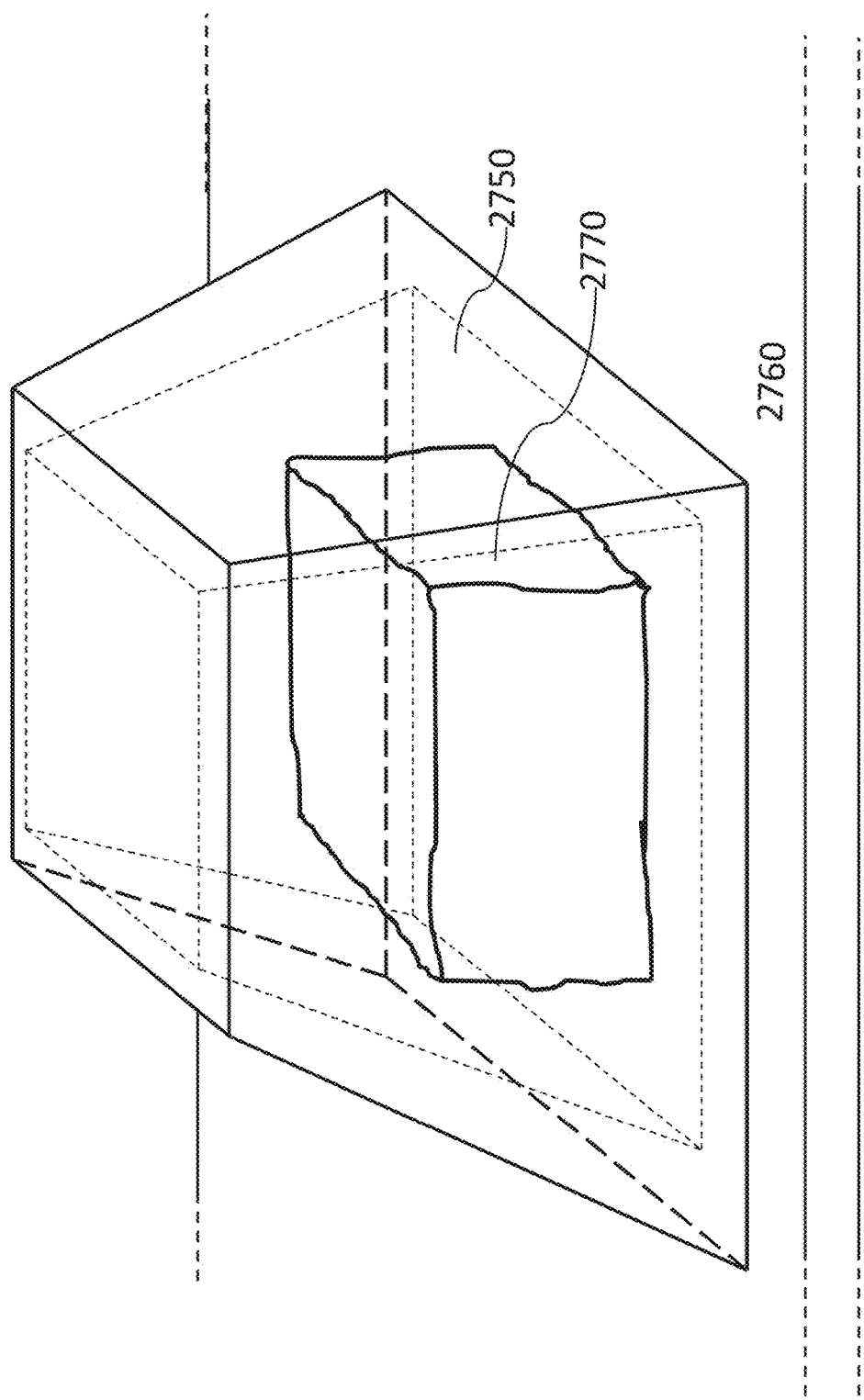
FIG. 27c depicts a cap interfacing with a site on the removable replaceable media element that comprises a printed deposition according to some embodiments.

A cap can also be used with a removable replaceable media element with reagents. FIG. 27c depicts an example representation wherein the cap 2750 covers a site or area 2760 within a removable replaceable media element that comprises a printed deposition 2770 comprising one or more reagents or other materials (for example, gas-generating, soap, emulsifier, disinfectant, etc.), for example, in the form of a soluble solid or gel comprising a soluble reagent or other type of material. The deposition can be functionally structured so as to provide a well-defined dissolution process in the fluid-exchange environment within the cap that does not result in problems such as sedimentation, loose fragments that could clog fluidic ports, clog fluidic valves, provide uncontrolled variations in concentration, or affect sensor operation. For example, the soluble solid or gel can comprise a polymer lattice, zeolite-like structure, etc. Depending upon the approach taken, the soluble solid or gel can comprise a soluble solid reagent, a mixable or soluble liquid reagent previously entrapped (macroscopically or microscopically) within the soluble solid or gel structure, and even a gas (for example entrapped within the structure or resulting from a chemical or enzymic reaction, etc.).

Figure 28:
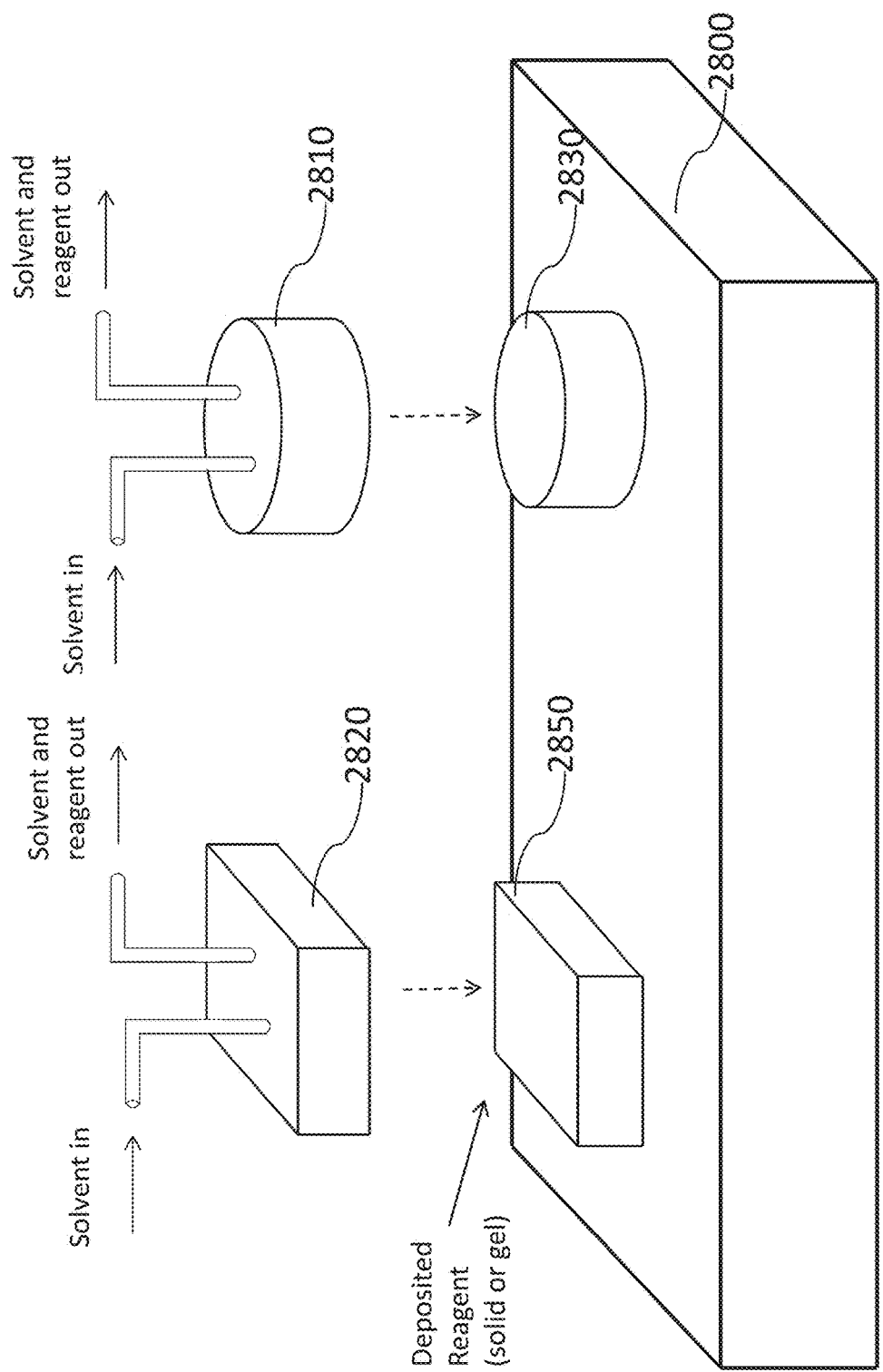
FIG. 28 depicts a cap with a fluidic port accepting solvent in and a fluidic port carrying solvent and reagent outward according to some embodiments.

FIG. 28 depicts an example representation of a removable replaceable media element 2800 wherein cap 2810 covers a site or area that comprises a printed reagent or material deposition 2830, such as solid or gel, and cap 2820 covers a site or area that comprises a printed reagent or material deposition 2850, such as solid or gel. Caps 2810 and 2820 are provided with respective input fluidic ports for accepting fluids in and respective output fluidic ports for carrying dissolved reagent outward. The arrangement can also be used for catalytic regents operating on incoming liquids or gasses. Although untapered square-opening (cap 2820) and round-opening caps (cap 2810) are depicted in FIG. 28, other cap shapes can be used.

Controllable Valves

The various embodiments of the present application can incorporate fluidics at various scales of physical size, ranging from those that use small-scale convention and fittings, controllable valves, pumps, and fluidic conduit manufacturing techniques to microfluidic scales involving transport of nanoliter volumes of materials. The value of the system would be expected to increase with increasing degrees of miniaturization as fewer sample, supplies, and power are required, field use is better facilitated, etc. As the scale of physical size decreases, the implementation of valves and pumps becomes less conventional and new emerging approaches and techniques will be used.

Further, these less conventional approaches and techniques are expected to continue to evolve. Many of these employ either elastomeric materials that response to applied pressure forces or complex polymers that change their physical properties responsive to electricity or heat. These and other know and as yet unknown approaches and techniques are expected to continue to evolve, emerge, and compete. However, as seen in the list above, there are many approaches that ultimately can be controlled by electrical current and/or voltage processes, making theme suitable for control by a microprocessor, other computation system, and/or digital logic circuitry.

Some examples of controllable valves suitable for microfluidics systems include but are not limited to those operated by:

Pneumatic or hydraulic stimulus (as for example, can be induced by larger scale apparatus driven by and controlled by electrical voltage or current)

Thermal processes (induced by electrical resistance or electrically produced infrared radiation)

Piezoelectric actuation (as for example, can be driven by electrical voltage or current)

Magnetic fields (as for example, can be induced by electrical current)

Torque or other mechanical actuation (as for example, can be induced by larger scale apparatus driven by and controlled by electrical voltage or current)

As one specific example, piezoelectric actuators can be used to manipulate elastomeric materials, either by direct mechanical contact of through intermediate pneumatic or hydraulic transfer. As another specific example, an electrically controlled microvalve leveraging large volumetric phase-change, for example as occurring in polyethylene glycol polymers (PEG), are thermally controlled using thin film resistive elements patterned using standard microfabrication methods, for example as taught in G. Kaigala, V. Hoang, C. Backhouse, "Electrically Controlled Microvalves to Integrate Microchip Polymerase Chain Reaction and Capillary Electrophoresis," *Lab on A Chip*, 2008, Vol. 8, No. 7, pp. 1071-1078 (whose authors indicate can readily scale down in size and require only electrical connection).

It is noted that thin films, elastomeric materials, and polymers can, through various processes and preparation, be functionally printed. Additionally, various practical aspects of the fabrication and operation of microfluidic valves based on elastomeric materials can be found, for example, in B. Mosadegh, *Design and Fabrication of Microfluidic Integrated Circuits Using Normally Closed Elastomeric Valves*, UMI Dissertation Publishing, 2010, ISBN 9781244570306.

Pumps

As will be seen, in many approaches supported by the present application analyte propagates through one or more serial chains of processing and sensing regions, and if there is more than one serial chain at least one fan-out stage is involved; these arranged in a manner that could be adequately managed with a single pump and the operation of valves to control where flow is active or blocked. Accordingly, a single or small number of pumps arranged for transport of small amounts of fluid but having a comparatively considerably larger overall physical size (for example, a miniature motor-driven, solenoid driven, or piezoelectric-driven diaphragm pump, a miniature motor-driven, solenoid-driven, or piezoelectric-driven peristaltic pump, a miniature motor driven, solenoid-driven, or piezoelectric-driven syringe pump, etc.).

As to microfluidic pumps, as with microfluidic valves there are many approaches that ultimately can be controlled by electrical current and/or voltage processes to control or induce a mechanical actuation. In many cases the same types of mechanical actuation used to operate a valve can be used to operate a diaphragm pump, actuate a stepping mechanism for a syringe pump, and arranged in a sequenced ensemble or drive a rocker arrangement to create a peristaltic pump. Many examples of these can be found in the literature, and it is expected that these and other know and as yet unknown approaches and techniques are expected to continue to evolve, emerge, and compete. However, as seen in the list above, there are many approaches that ultimately can be controlled by electrical current and/or voltage processes, making theme suitable for control by a microprocessor, other computation system, and/or digital logic circuitry. Further as to microfluidic pumps, much attention in the microfluidics literature has been directed to electro-osmotic transport. Although the present application provides for the use of electro-osmotic transport where applicable or advantageous, it is noted that the electric fields and introduced voltage potentials involved can affect biomolecules, cells, suspensions, etc, can introduce unwanted or unmanageable electrochemical effects, and can interfere with the intended operation of many types of sensing technologies and processes, Accordingly, in some embodiments electro-osmotic transport is employed where applicable or advantageous to transport materials (or a somewhat restricted class of materials) between fluidic locations but is nonoperational when sensing that could be affected by voltages, current, and fields associated with electro-osmotic operation. The present application in a similar manner provides for the use of other similar pump techniques, for example as taught in S. Chang, E. Beaumont, D. Petsev, O. Velev, "Remotely Powered Distributed Microfluidic Pumps and Mixers Based on Miniature Diodes," *Lab on a Chip*, 2008, Vol. 8, pp. 117-124.

Organization and Handling of Fluidic, Gas Exchange, and Other Material Flows

With valves and pumps applicable to the present application now discussed, attention is now directed to interfacing the sites on the removable replaceable media element to fluidics within or intermediate to the base unit, as well as electronics and optics within or intermediate to the base unit, and associated interconnection. Attention is first directed to fluidics interfacing, fluidic control, and fluidics interfacing.

As an example, fluidic and gas exchange interconnections can be provided by controllable microfluidic bus technologies such as that taught in U.S. Pat. No. 8,032,258 and pending U.S. patent application Ser. Nos. 13/251,286 and 13/251,288). Fluidic interconnections among caps and associated sites can be supplemented with additional controllable fluidic paths. In some implementations fluidic interconnections carry fluids, gases, solvents, cleaning fluids and/or clearing gases (such as that taught in pending U.S. patent application Ser. Nos. 11/946,678 and 13/314,170) and/or can connect to controllable microfluidic bus (such as that taught in U.S. Pat. No. 8,032,258 and pending U.S. patent application Ser. Nos. 13/251,286 and 13/251,288). The fluidics arrangements described thus far understood to extend to cover materials and situations such as suspensions (for example comprising cells), gases dissolved liquids, materials at thermodynamic critical points (such as vapors and gases including vapors), slurries, gases comprising particulates or colloids, emulsions in various stages (flocculation, creaming, coalescence, Ostwald ripening, etc.), micelles, etc. as well as combinations of these. In various aspects of the present application, the fluidics arrangements are arranged to interface to wells and reagent, depositions on the removable replaceable media element.

Figure 29:
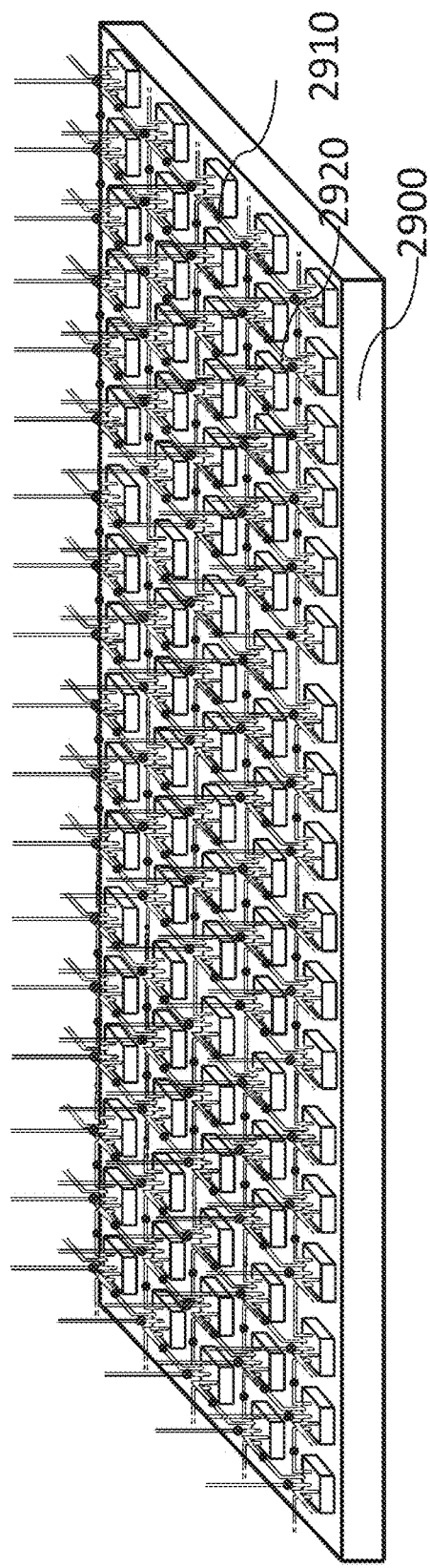
FIG. 29 depicts an example arrangement wherein caps interconnected with fluidics arrangements interface to associated sites on a portion of the removable replaceable media element according to some embodiments.

FIG. 29 depicts an example arrangement wherein caps 2910 are interconnected with fluidics and gas exchange arrangements 2920 to interface with wells and reagent deposits on the removable replaceable media element 2900.

Fluid Reservoir

In an embodiment, at least one fluid reservoir is provided in the base unit.

In an embodiment, the fluid reservoir is removable.

In an embodiment, the fluid reservoir is built into the removable replaceable medium element, for example within or beneath the sensor-level substrate removable replaceable medium element.

In an embodiment, at least one disposal reservoir is provided in the base unit.

In an embodiment, that disposal reservoir is removable.

In an embodiment, the disposal reservoir is built into the removable replaceable medium element, for example within or beneath the sensor-level substrate removable replaceable medium element.

In an embodiment, the fluid reservoir and disposal reservoir are in a unitary removable configuration.

Machine-Readable Information Aspects of the Base Unit

As described earlier, the machine readable information provided by the removable replaceable can include data and/or algorithms and can take the physical form of printed optical codes (such as printed optical bar codes, printed optical matrix codes, printed holographic codes), printed magnetic code stripe, printed electronic data memory, etc.).

As an example, FIGS. 30a-30c depict representations of examples of how optical ROM printed on the removable replaceable media can be read by the base unit. FIG. 30a depicts an example linear (1-dimensional) optical "bar" code 3010 that can be printed on instances of the removable replaceable medium and a "reading array" 3020 comprising for example a 1-Dimensional Photodiode Array, 1-Dimensional LED Array, 1-Dimensional CCD Array, etc. located in the base unit and configured to lie effectively optically adjacent to the optical bar code printed on the removable replaceable media. No mechanical scanning is needed with this approach. (As described later, LEDs can operate as wavelength-selective photodiodes.) The barcode 3010 can be lit by various arrangements, including back lighting, frontal light, via selected LEDs in an LED array, etc. Translational-displacement of the optical bar code 3010 with respect to the "reading array" 3020 (arising from minor variations in removable replaceable media positioning with respect to the base unit) can be readily handled in software on a microprocessor or other processor chip comprised by the base unit. If the "reading array" 3020 comprises LEDs with a number of distinguishable different emission wavelengths, the LED array can be used to implement wavelength division multiplexing arrangements, allowing use of multiple colored inks used in the printing of the optical bar code 3010 to increase the information density on the optical bar code 3010.

FIG. 30b depicts an example elongated rectangular 2-dimensional optical "matrix" code 3030 that can be printed on instances of the removable replaceable medium and a "reading array" 3040 comprising for example an elongated rectangular 2-Dimensional Photodiode Array, 2-Dimensional LED Array, 2-Dimensional CCD Array, etc. located in the base unit and configured to lie effectively optically adjacent to the optical matrix code printed on the removable replaceable media. No mechanical scanning is needed with this approach. The matrix code 3030 can be lit by various arrangements, including back lighting, frontal light, lighting by LEDs in an LED array, etc. Translational displacement of the matrix code 3030 with respect to the "reading array" 3040 (arising from minor variations in removable replaceable media positioning with respect to the base unit) can be readily handled in software on a microprocessor or other processor chip comprised by the base unit. If the "reading array" 3040 comprises LEDs with a number of distinguishable different emission wavelengths, the LED array can be used to implement wavelength division multiplexing arrangements, allowing use of multiple colored inks used in the printing of the optical matrix code 3030 to increase the information density on the optical matrix code 3030.

FIG. 30c depicts an example non-elongated rectangular 2-dimensional optical "matrix" code 3050 that can be printed on instances of the removable replaceable medium and a "reading array" 3060 comprising for example a non-elongated rectangular 2-Dimensional Photodiode Array, 2-Dimensional LED Array, 2-Dimensional CCD Array, etc. located in the base unit and configured to lie effectively optically adjacent to the 2-d optical matrix code 3050 printed on the removable replaceable media. No mechanical scanning is needed with this approach. The 2-d optical matrix code 3050 can be lit by various arrangements, including back lighting, frontal light, lighting by LEDs in an LED array, etc. Translational displacement of the 2-d optical matrix code 3050 with respect to the "reading array" 3060 (arising from minor variations in removable replaceable media positioning with respect to the base unit) can be readily handled in software on a microprocessor or other processor chip comprised by the base unit. If the "reading array" 3060 comprises LEDs with a number of distinguishable different emission wavelengths, the LED array can be used to implement wavelength division multiplexing arrangements, allowing use of multiple colored inks used in the printing of the optical matrix code to increase the information density on the optical matrix code.

Alternatively, other arrangements for optical ROM, electronic ROM (for example, implemented with printed electronics), magnetic ROM, etc.) can also be used.

In an embodiment, compressed specification languages and procedural languages can be used to minimize the number of characters stored on the ROM.

Separable Interfacing Module

In many implementations and usage scenarios it can be advantageous to implement at least the fluidics arrangements in a separable interfacing module. In some embodiments the interfacing module can be comprised by the base unit in either a fixed or replaceable arrangement. In other embodiments the interfacing module can be comprised by the removable replaceable media element in either a fixed or replaceable arrangement. In yet other embodiments the interfacing module can be configured to be inserted into either (at the choice of user or manufacturer product-design) the base unit or attached to the removable replaceable media element in either a fixed or replaceable arrangement.

In various embodiments, the interfacing module can additionally comprise one or more of various additional components including but not limited to electronic circuitry, valves or portions of valves, optical elements, electro-optical elements, mechanical actuators, pumps, reservoirs, microprocessors, additional sensors, etc.

Figure 31:
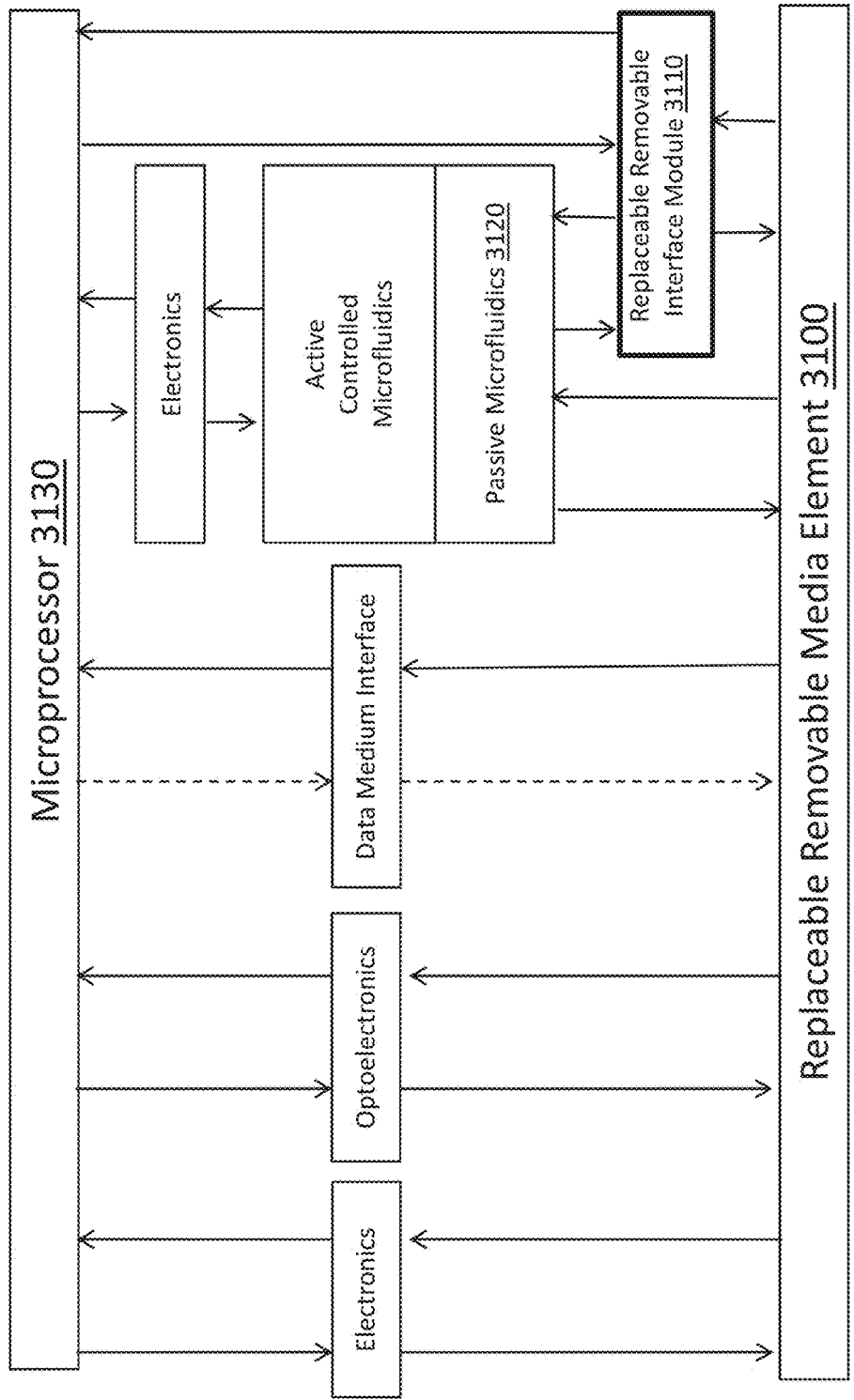
FIG. 31 depicts an example adaptation of the example architectural arrangement provided in FIG. 22b wherein a removable replaceable interface module is provided interfaces to the microfluidics and computing infrastructure.

Further as to the "open architecture" provisions of the present application involving removable replaceable interface module, FIG. 31 depicts an example adaptation of the example architectural arrangement illustrated in FIG. 22b wherein a removable replaceable interface module 3110 is provided to interface to the microfluidics 3120 and computing infrastructure 3130. Other architectural arrangements are of course possible, anticipated, and provided for by the present application.

In various embodiments, the interface module 3110 can be fabricated in part or in whole by functional printing. In various embodiments, the interfacing module can be fabricated in part or in whole by injection molding. In various embodiments, the interface module 3110 can be fabricated in part or in whole by casting.

When the interface module 3110 is employed as a removable component for use in the base unit, such an arrangement allows for simplified maintenance, performance upgrades, density upgrades, feature upgrades, means of contamination control within the base unit, etc. When the interface module 3110 is employed as an attached or user-attachable component to the removable replaceable media element, such an arrangement allows for containment of contamination, simplified usage, performance customizations, density customizations, feature customizations, etc.

Figure 32:
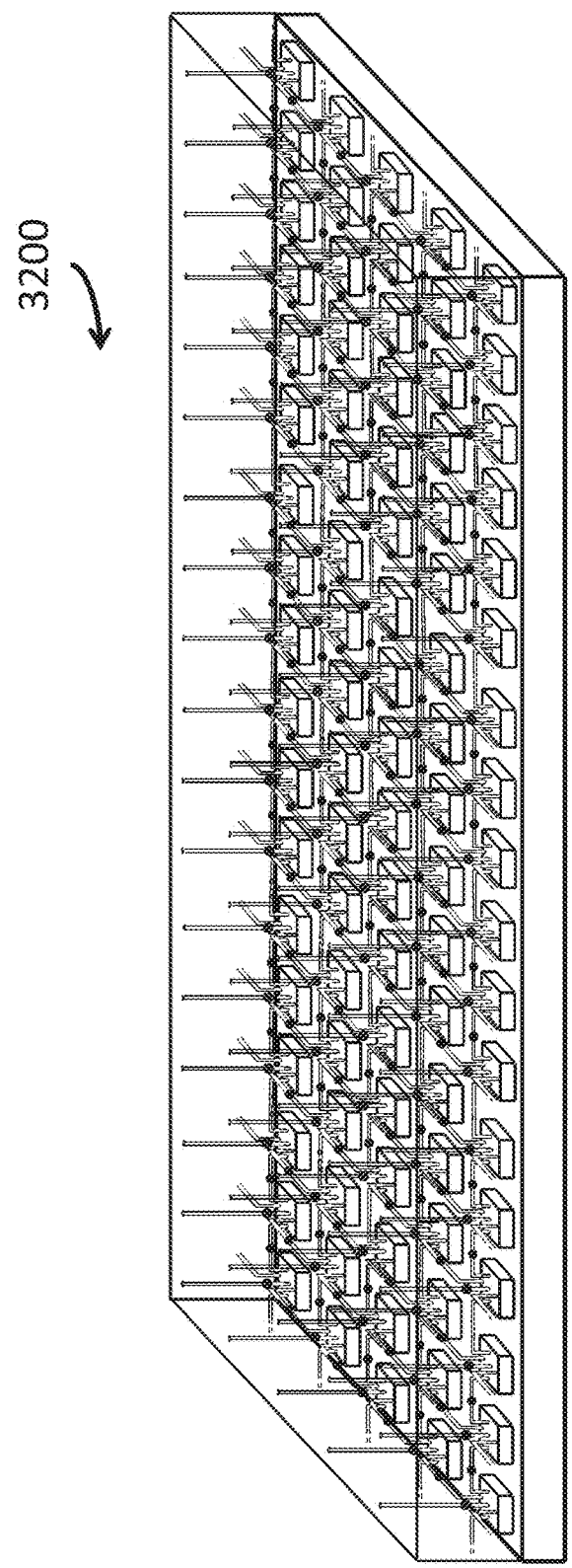
FIG. 32 depicts an embodiment in which at least the fluidics arrangements are comprised in an interfacing module.
Figure 33:
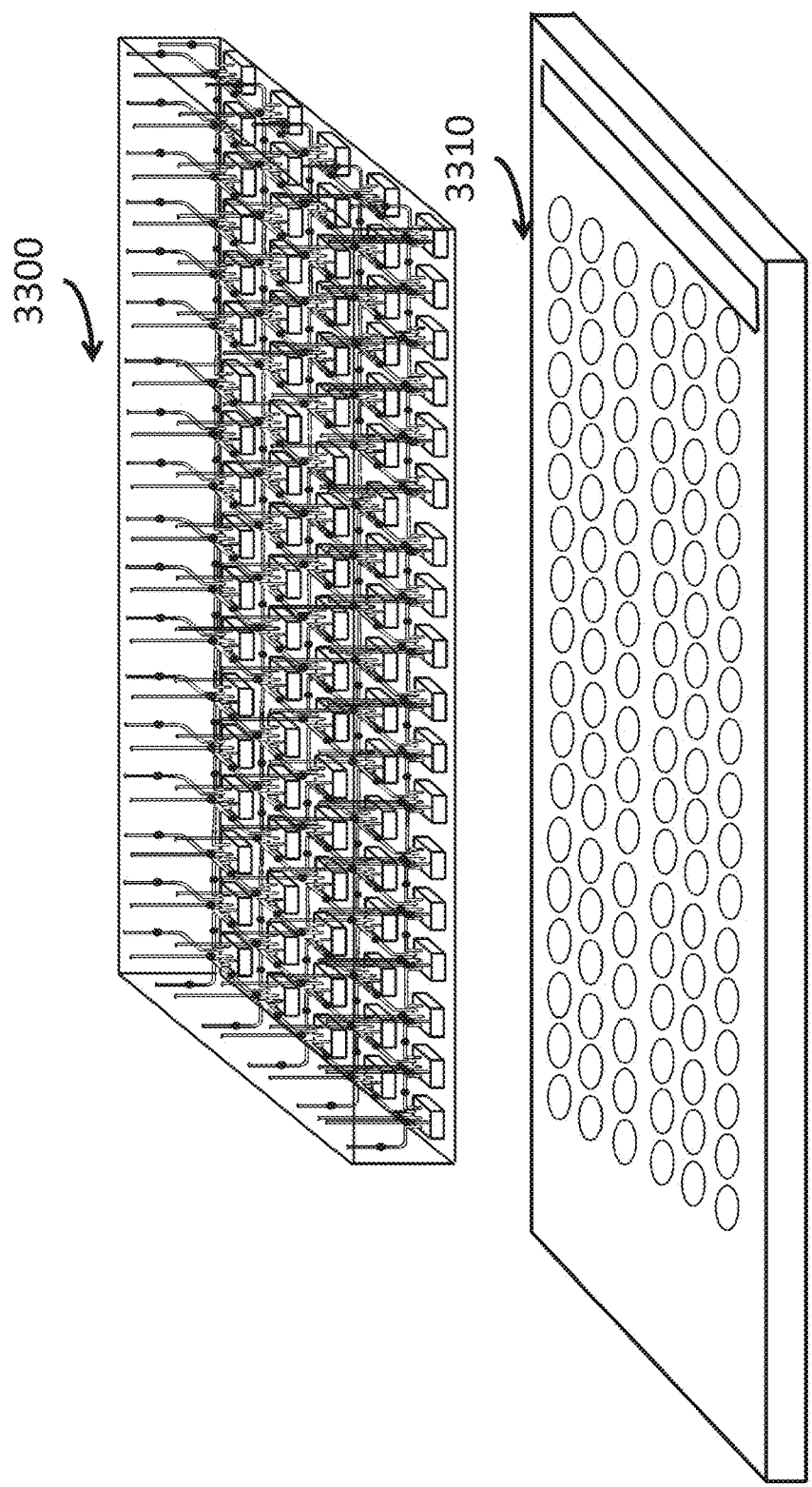
FIG. 33 depicts an embodiment in which the interfacing module can be configured to be inserted into either the base system or attached to the removable replaceable media element in either a fixed or replaceable arrangement.

FIG. 32 depicts a variation on the example arrangement of FIG. 29 wherein at least the fluidics arrangements are comprised in an interfacing module. FIG. 32 illustrates an interfacing module 3200 comprising fluidics. FIG. 33 depicts an example wherein the interfacing module 3300 (e.g., interfacing module 3200) can be configured to be inserted into either (e.g., at the choice of user or manufacturer product-design) the base unit or attached to the removable replaceable media element 3310 in either a fixed or replaceable arrangement.

Software

Figure 34:
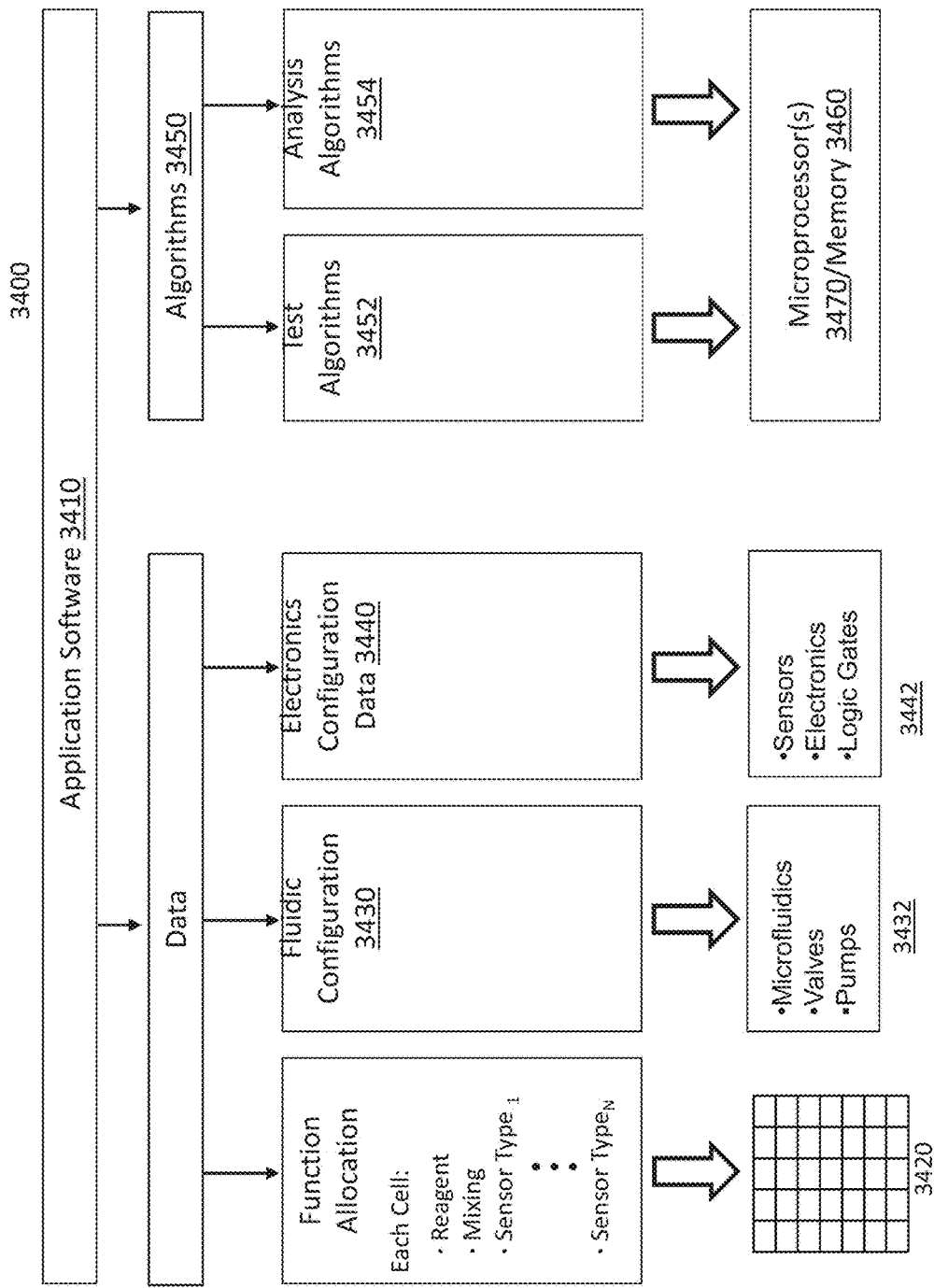
FIG. 34 depicts a representation of applications software that can include, for example, configuration data, assignment data, data used by algorithms, test algorithms, analysis algorithms, etc.

FIG. 34 depicts a representation of a system 3400 according to certain embodiments. System 3400 includes applications software 3410, which can include, for example, configuration data, assignment data, data used by algorithms, test algorithms, analysis algorithms, etc. A well (and reagent) configuration table 3420 that can be used to specify, among other things, what mode each well is to operate in. System 3400 includes fluidic configuration data 3430 that can be used to configure fluidic elements 3432, such as valves (and which can also include pumps). System 3400 includes electronic configuration data 3440 that used to configure electronic elements 3442, such as sensor interface electronics, logic gates, routing of sensor signals to A/D converters, mixed signal integrated circuits, digital processors, microprocessors, etc. System 3400 includes one or more algorithms 3450, such as test algorithms 3452 (e.g., standard or special operation of sensors and fluidics, etc.), as well as analysis algorithms 3454, e.g., used to produce the statistical analysis of the information provided by the sensors. Algorithms 3450 are stored in memory 3460 and executed by microprocessor 3470.

User Interface

Figure 35:
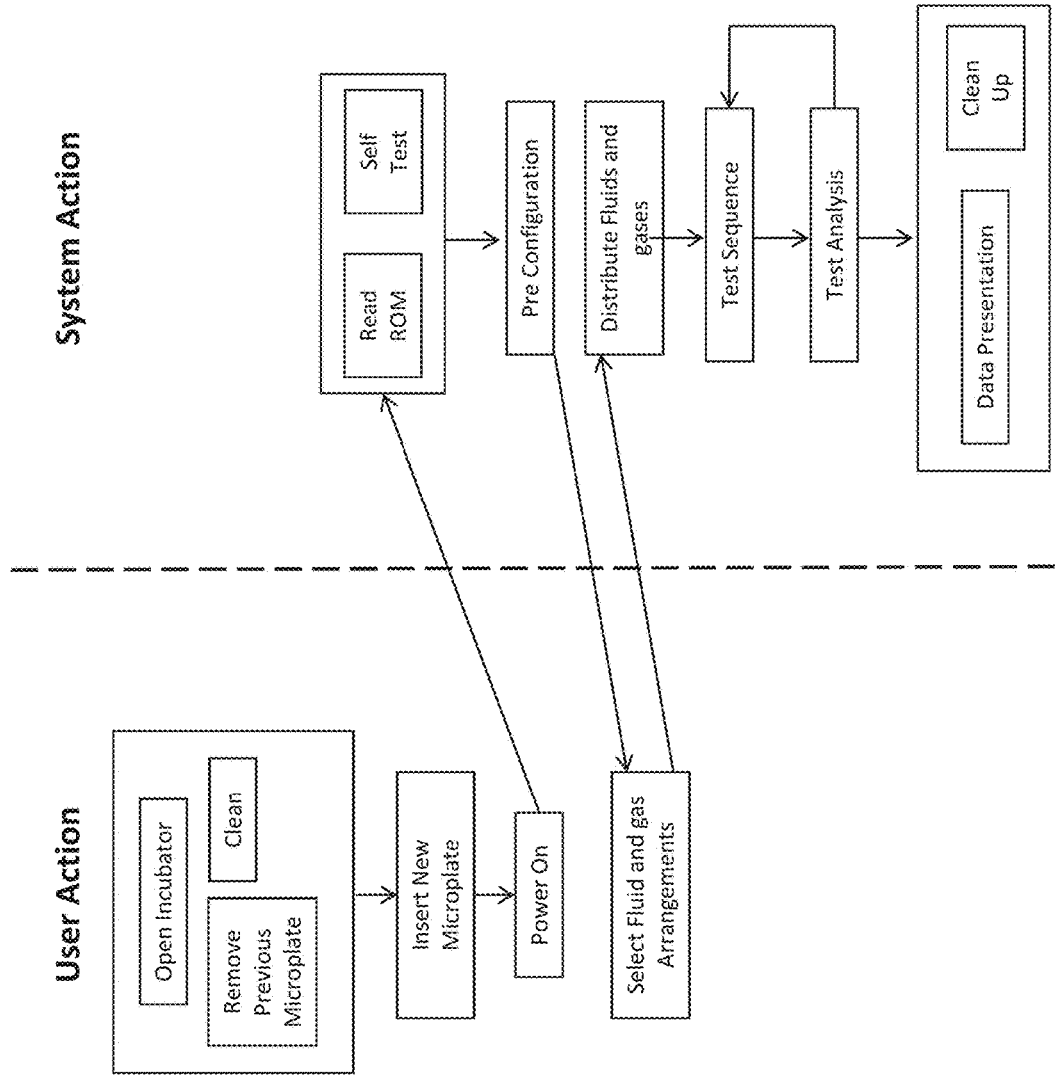
FIG. 35 depicts a representation of an example user experience scenario using an example implementation of the technology.

FIG. 35 depicts a representation of an overall example user experience scenario using an example implementation of the technology. The depicted steps, features, elements, event sequence, clustering, and flow are merely illustrative and are in no way limiting.

EXAMPLE APPLICATIONS ENABLED BY EMBODIMENTS

Figure 36:
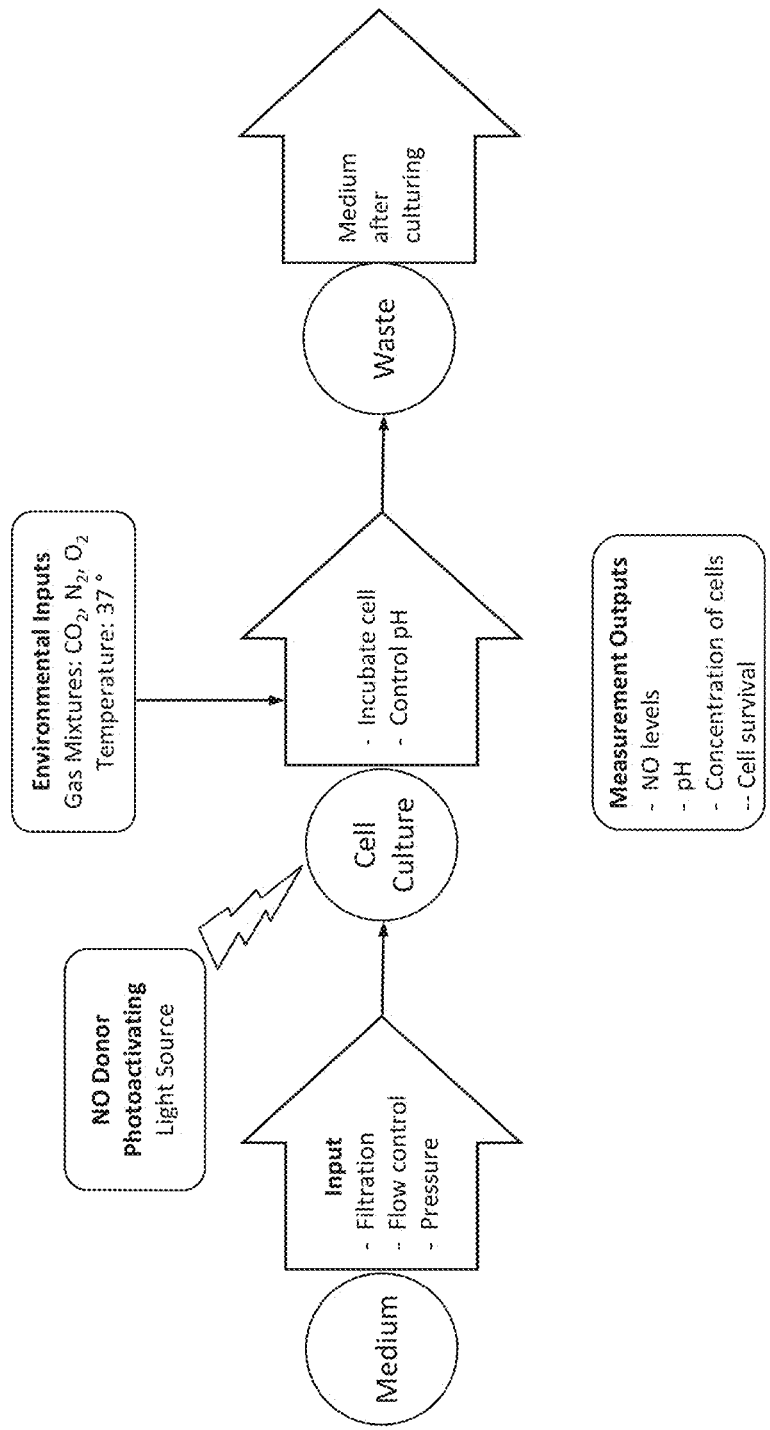
FIG. 36 depicts a representation of the strategy of an example experiment facilitated by various embodiments.
Figure 37:
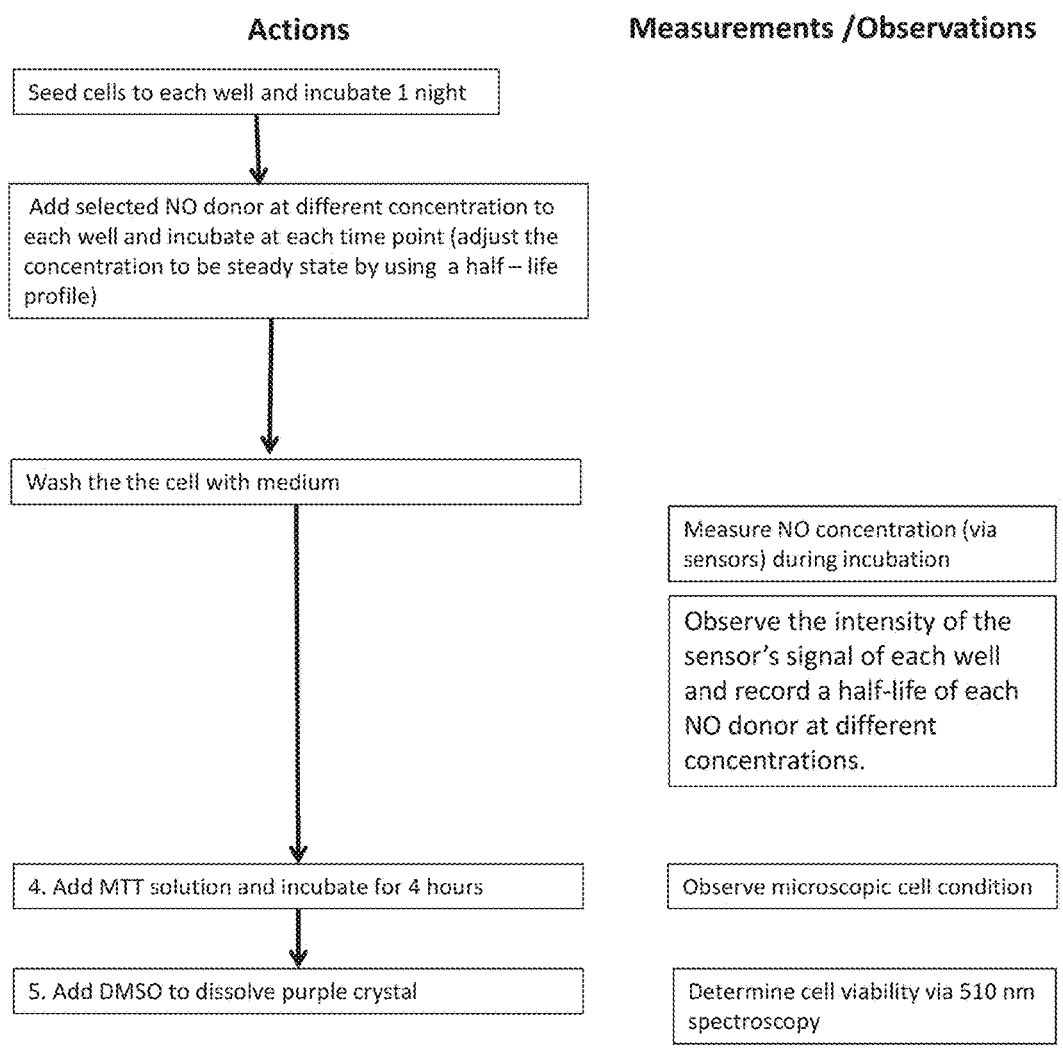
FIG. 37 depicts a flow chart of an example experiment leveraging various aspects of various embodiments.
Figure 38:
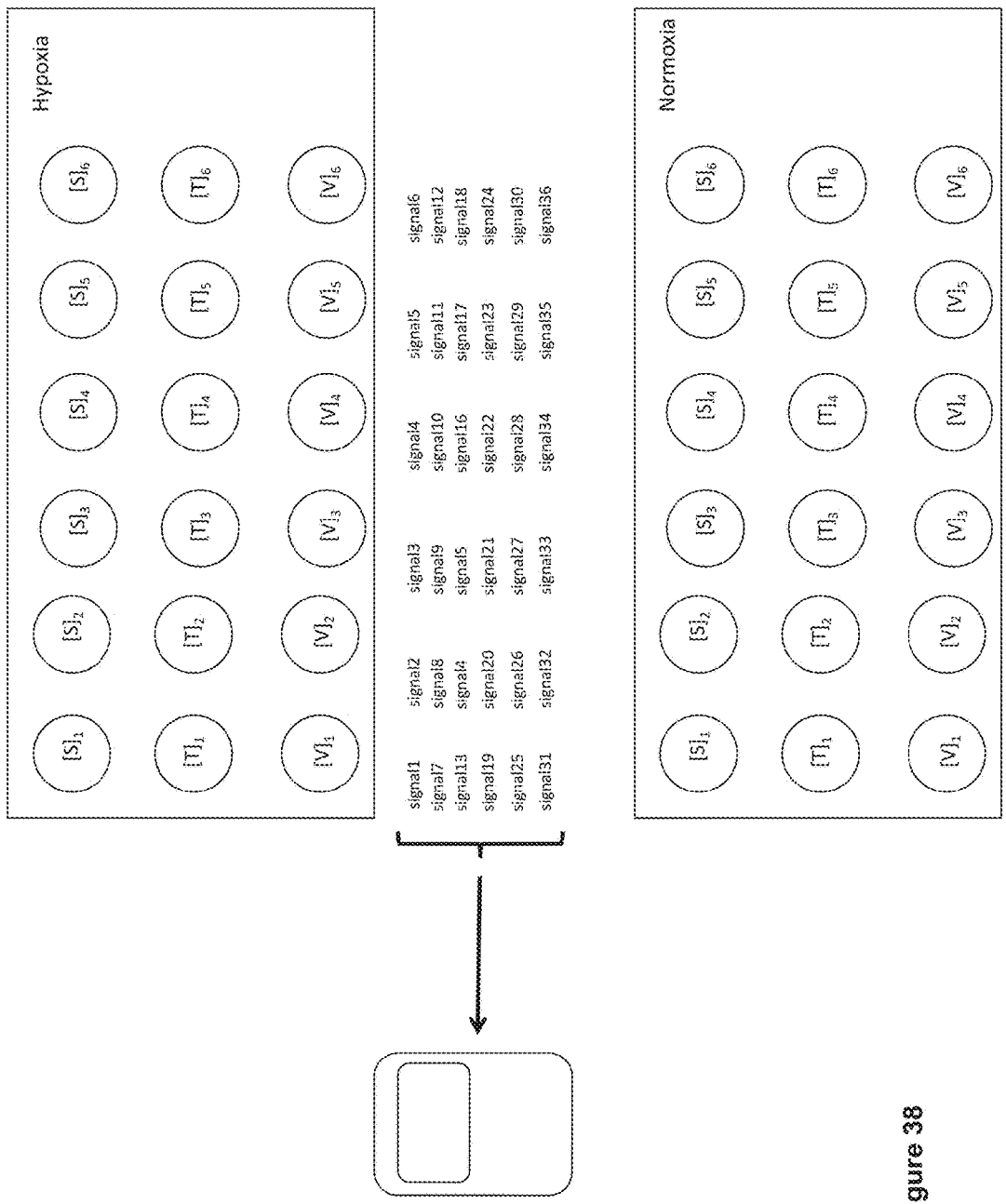
FIG. 38 depicts a representation of how measurement data obtained from parallel hypoxia and normoxia conditions are compared.
Figure 39:
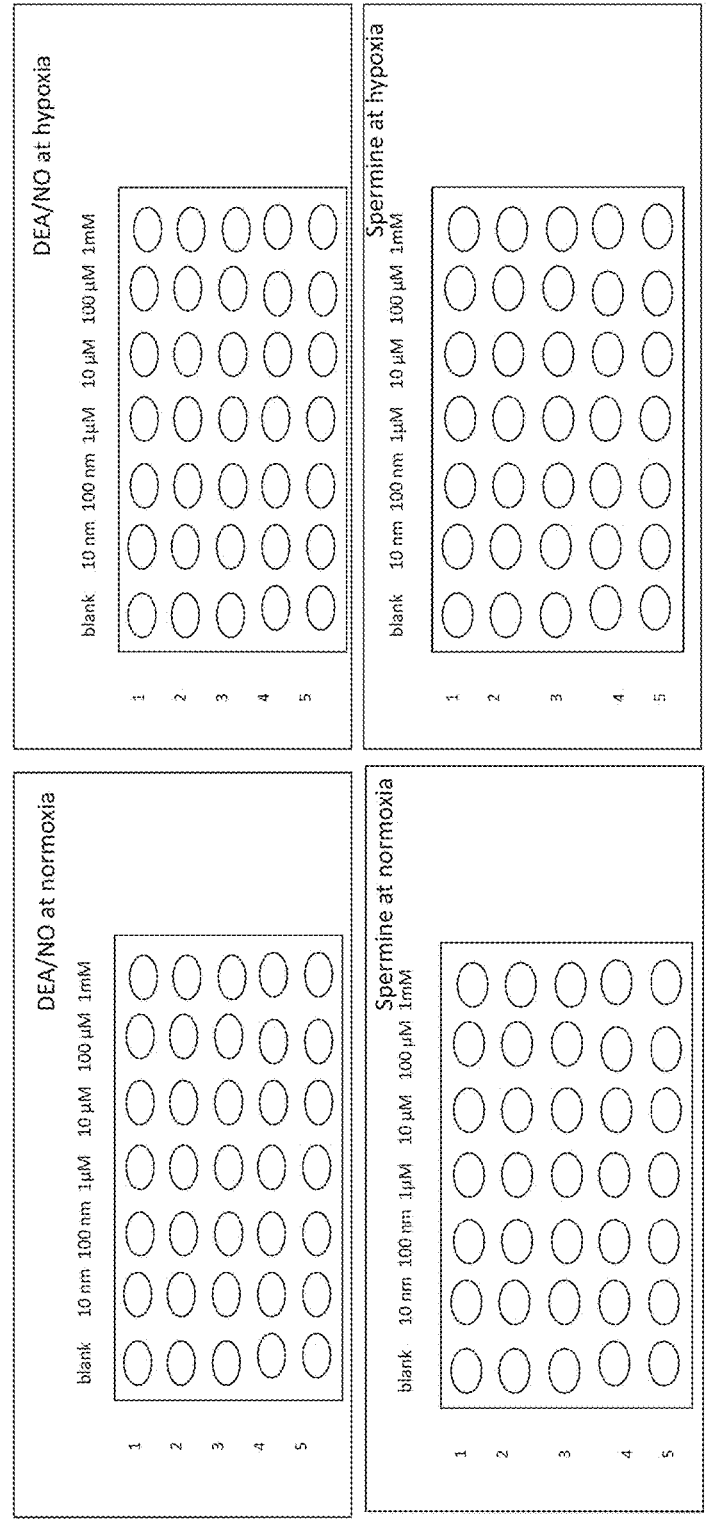
FIG. 39 depicts a representation of how NO donor material profiles can be studied.
Figure 40:
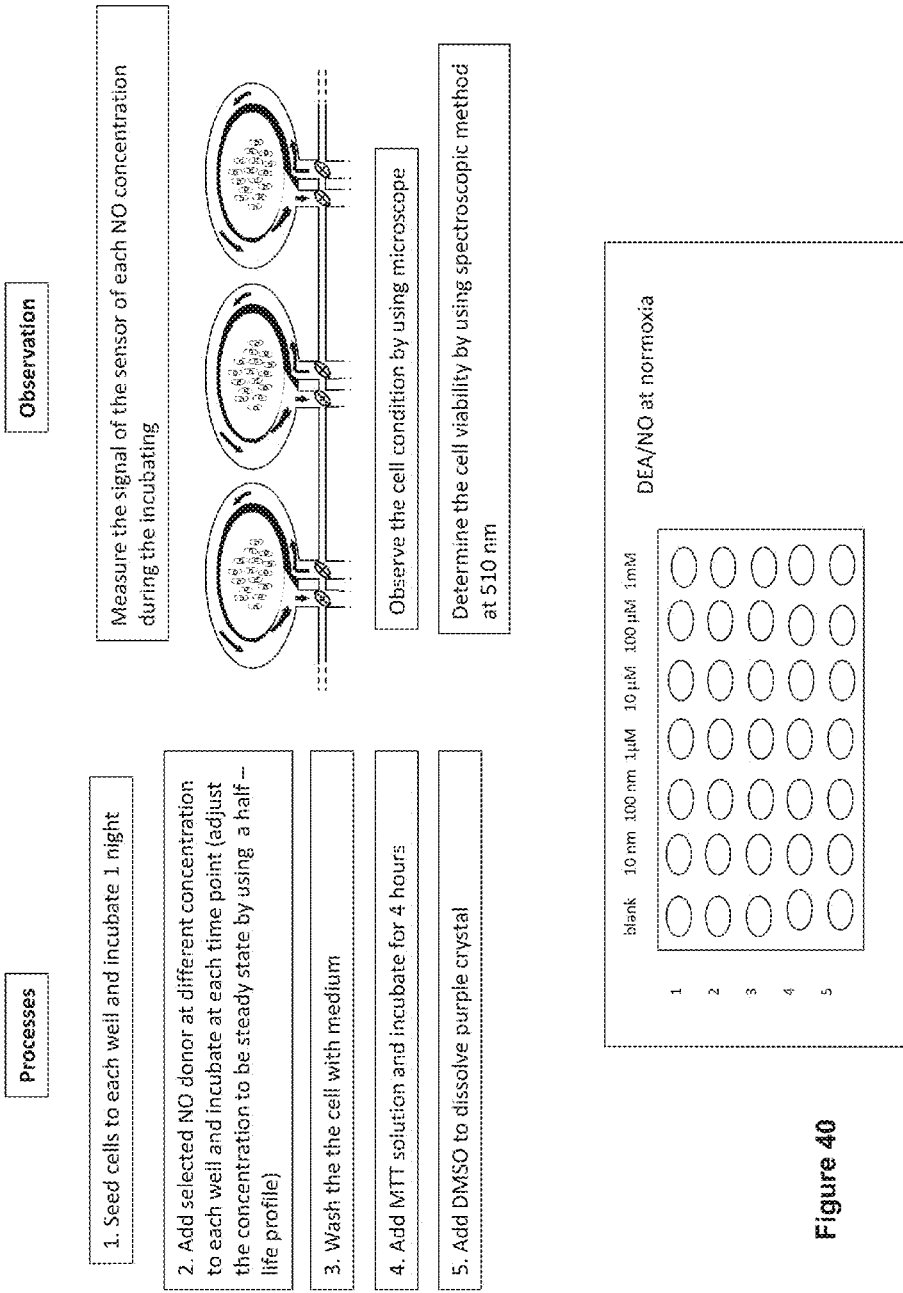
FIG. 40 depicts a representation of experimental processes for studying effect of NO on cell survival.

This section provides an example experiment showcasing example applications that are enabled by various embodiments described earlier and which otherwise, if they can even be performed at all, can be performed only with great laboratory skill, high experiment-corruption risk, and with poor efficiently As an overview, FIG. 36 depicts a representation of the strategy of an example experiment facilitated by various embodiments. FIG. 37 depicts a flow chart of an example experiment leveraging various aspects of various embodiments. FIG. 38 depicts a representation of how measurement data obtained from parallel hypoxia and normoxia conditions are compared. FIG. 39 depicts a representation of how NO donor material profiles can be studied. FIG. 40 depicts a representation of experimental processes for studying effect of NO on cell survival.

As is known, Nitric Oxide (NO) acts as double-edged sword, which induces and prevents cell death, depending on various factors. The mechanism for the NO regulation of cells is not fully understood. Various embodiments support the design and rapid conducting of intricate comparative experiment and therapy design methods leveraging viable hypothesis supported by current research findings. In comparison, conventional cell incubators cannot provide the variability and degrees of control necessary.

Various embodiments can be used to effectively determine the effects of NO by controlling the majority parameters such as the steady-state concentration of NO, the duration of NO exposure, and the local level of oxygen. Such experiment designs facilitated by various embodiments are structured to improve the poor understanding of NO regulation of cells, and further can be directly adapted for therapy design.

Embodiments of the present application directs these experiment design and therapy design methods to the study and treatment of cancer. In the embodiments discussed herein, although cancer cells are discussed, other types of cells can also be used. In an application, the effects of exogenous NO on inducible Nitric Oxide Synthase (iNOS) expression and signal transduction in ovarian cancer is applied to drug discovery and therapy design for ovarian and other cancers. An example framework of such experiments is provided in pending U.S. patent application Ser. No. 13/155,370 by one of the inventors, and the example framework provided therein is considered here as an example for showcasing the value provided by various embodiments over the value available from current and previous cell incubator technologies.

In the context of the example experimental framework provided in pending U.S. patent application Ser. No. 13/155,370, various embodiments support the design and rapid conducting of intricate comparative experiments for the study of Nitric Oxide (NO) in the control of cell death for use in cancer therapies, the method comprising:

Establishing that long term exposure of cells to low concentration of exogenous nitric oxide causes a negative feedback mechanism to induce down regulation of inducible Nitric Oxide Synthase (iNOS) by choosing a first NO donor that can produce a relatively low level of NO concentration over a relatively long NO-production half-life, Applying that NO donor to a cell culture media at selected time points, measuring the levels of iNOS concentration and NO concentration to produce first measurements, and recording first data corresponding to the first measurements;

Establishing that high concentration of exogenous NO does not affect to the expression of iNOS but instead will cause apoptosis of cells by choosing a second NO donor that can produce a relatively high level of NO concentration over a relatively short NO-production half-life, applying that NO donor to a cell culture media at selected time points, Measuring NO concentrations to produce second measurements, and recording second data corresponding to the second measurements; and establishing that for a given level of NO concentration, the expression of iNOS down-regulates more in hypoxic conditions than in normal oxygen conditions by choosing a third NO donor that generates a relatively low concentration of NO, Applying that NO donor to a cell culture media at selected time points, measuring the levels of iNOS and NO concentration to produce third measurements, Recording third data corresponding to the third measurements, and comparing the iNOS response between normal and hypoxic environments, wherein at least one of the first data, second data, and third data are used to create a cancer therapy that manipulates exogenous NO in a hypoxic area of cancer cells.

Various embodiments support methods for designing a cancer therapy by manipulating the concentration and duration of Nitric Oxide (NO) for the control of cell death, the method comprising:

Using a first NO donor to produce a relatively low level of NO concentration over a relatively long NO-production half-life, Applying that NO donor to a cell culture media at selected time points, measuring the levels of inducible Nitric Oxide Synthase (iNOS) and NO concentration to produce first measurements, and recording first data corresponding to the first measurements;

Using a second NO donor to produce a relatively high level of NO concentration over a relatively short NO-production half-life, applying that NO donor to a cell culture media at selected time points, measuring the levels of iNOS and NO concentration to produce second measurements, and recording second data corresponding to the second measurements; and Using a third NO donor to produce a relatively low concentration of NO, applying that NO donor to a cell culture media at selected time points, measuring the levels of iNOS and NO concentration to produce third measurements, recording third data corresponding to the third measurements, and comparing the iNOS response between normal and hypoxic environments, wherein at least one of the first data, second data, and third data are used to create a cancer therapy that manipulates exogenous NO in a hypoxic area of cancer cells.

Such a cancer therapy comprises an agent manipulates exogenous NO in the hypoxic area of cancer cells.

Various embodiments support the design methods for a cancer therapy, the method comprising:

Using experimental measurements to find ranges of Nitric Oxide (NO) concentrations and exposure durations which cause apoptosis of cancer cells residing in a hypoxic environment;

Identifying an agent that can produce said ranges of Nitric Oxide (NO) concentrations and exposure durations, and Deploying the agent into a hypoxic area comprised by cancer cells, wherein the agent manipulates the concentration and duration of Nitric Oxide (NO) within said ranges to invoke apoptosis of the cancer cells.

Much circumstantial evidence suggests a hypothesis that low NO concentration causes the progression of cancer cells, but high NO concentration induces cancer cells apoptosis. However, no evidence has isolated the factor or process that controls the negative feedback of NO to iNOS expression. Candidates for such factor or process can be argued to prominently include the local molecular concentration and temporal duration of NO exposure events.

The NO mechanism is not clearly elucidated as to the conditions and processes wherein NO induces cancer cell progression or wherein NO promotes cell death. Accordingly, experiment designers using conventional cell incubators are faced with the prospect of trying to find a needle in haystack in trying to answer how NO regulation on tumor cells.

Due to in fact that iNOS plays a role in cancer progression and metastasis [12] and one of all pathways that regulate cancer progression is negative feedback of NO to iNOS, it can be hypothesized that long term exposure of cancer cells to low concentration of exogenous NO might reduce iNOS expression by negative feedback effect. In contrast, high concentration and short term of NO exposure might not regulate iNOS expression and retards the survival of cancer cells. Another hypothesis that can be made is that low concentration of NO causes down-regulation of iNOS under hypoxia more than in normoxia. Since high level of oxygen in the environment, normoxic condition increases metabolism of NO. Understanding mechanisms controlling the balance between the NO related protective and destructive action can therefore be potentially be a crucial modification of the regimen of exogenous NO for alternative tumor therapy.

Quantitative Measurement of Nitric Oxide Via Spectroscopic Method NO Kit

NO contained in a sample is metabolized to nitrate and nitrite, and then nitrate is converted to nitrite by nitrate reductase. The nitrite will react with Griess reagent, an azo compound, which causes the color to turn purple which can thus be detected by spectrophotometer FIG. 41 depicts the principle of operation of such an NO quantitative kit. In this manner, the concentration NO resulting from the NO metabolite (nitrite) can be determined. However, NADPH, a crucial cofactor for nitrate reductase, decreases the sensitivity of this method by interfering the Griess reaction. To increase the sensitivity, lactate dehydrogenase (LDH) can be added to the step prior to Griess reaction so as to address the NADPH scavenged cofactor.

Electrochemical NO Detection

NO is a highly reactive molecule and can be oxidized to be other reactive oxygen species such as superoxide anion ($O_2^-$ and the hydroxyl radical (.OH), peroxynitrite (ONOO—). Electron transfer between the "active" electrode and the molecule causes an electrical current. The electrical current, redox current, is proportional to the concentration of the molecules. Therefore the redox current is amplified and then it can indicate the concentration of NO in Amperometric analysis. Shibuki invented the first NO-sensitive probe in 1990 [4]. The improvement of the NO probe has focused on the sensitivity, selectivity and reliability. However the main problem the electron exchange with the chemical species is very slow; consequently it induces a low response time and poor sensitivity. There are two solutions for solving the difficulty. First one is increasing the applied potential—gaining the energy of the electrons. In fact, this method reduces a signal to noise ratio and leads to the loss of selectivity, even though it increases the response rate of electrons. Second strategy is using a catalyst to reduce the activation energy. This strategy minimizes the energy gap between the working electrode and the related chemical; hence, it improves the electron transfer and increases the signal to noise ratio and the selectivity [5,6]. From the study of Brovkovych et all, 1990, the catalyst using in reducing the energy gap is porphyrin. They develop phophyrin microsensors based on coated carbon fibre. Phorphyrin coating diminished the potential to 0.7 V and improves the response significantly [7].

The electrochemical NO detection's systems are commercial available, such as, Amino—700 from the Innovative Instruments, Inc. and ISO-NO system from WPI Inc. These systems embody NO permeable membrane to reduce interference from other oxidized molecules. The electrical current responds to changes of temperature [8]. Despite this NO application, the electrochemical detection is also used in other molecules, such as, oxygen and oxygen derivatives, carbon dioxide, hydrogen sulfide glucose, and ATP.

An example of measuring NO concentration by using electrochemical NO detection is Jean A. Cardinale's experiment which measured Nitric oxide concentrations using an Apollo 4000 Free Radical Analyzer with ISO NOP sensors (World Precision Instruments, Sarasota, Fla.). To determine the concentrations of NO, this study created a standard curve for conversion of pA (the electric current density unit) to nM (concentration) by titrating of concentration of a standard potassium nitrite solution to a solution of 0.1 M KI (potassium iodide) in 0.1 M $H_2SO_4$ (sulfuric acid). The reaction was performed at 37° C. [21].

Fluorescence Indicator of NO

Many substances such as diaminofluoresceins (DAF-2) react with NO and form a fluorescent complex. The reaction in the presence of oxygen creates a bright green fluorescent triazolo derivative. In addition, other NO indicators such as diaminorhodamine (DaR), or diaminoantraquinone (DAQ or DAA) chemically react with NO irreversibly. From the study of glial cell culture, the signal of DAF-2-NO complex is extremely small, in the range of 8 nM [9]. In addition, the results modulation of neurotransmission requires NO concentration as 0.5-10 nM [8].

Fluorescence Resonance Energy Transfer (FRET) Detection of NO

Pairs of fluorophores act as donor of photons and the other as their acceptor. The FRET indicator such as Cyan and yellow mutants of the green fluorescence proteins (GFP) were used to measure the concentration of biological active molecules. A deep blue light from the indicators is used to excite the cyan fluorescence protein to emit blue photons. Consequently, the yellow fluorescence protein traps the blue photon. As a result, the ratio between the fluorescence signals, initiated by the cyan and yellow proteins depends on the configuration of the molecule and the distances between them; and may be used as an index of FRET intensity. The first discovery of an NO-sensitive FRET-based probe was made by Honda and his colleagues [31]. The study explained that cGMP dependent protein kinase (PKG) acts as NO sensor between two GFP mutants. In fact, PKG is sensitive to cGMP, which depends on the activation of sGC. Therefore, this phenomenon is reported as NO-mediated effects.

Measurement of NO Effects in Retro-Dialysis Experiments

Micro-dialysis experiments are able to determine NO metabolites. However, the limitation of the experiments is slow [10].

Detection of NO by Electron-Paramagnetic Resonance (EPR)

EPR Spectroscopy is responsive to NO trapping invoked by a stable complex, and can be used to indicate the NO trapping location. In the meantime, it is able to estimates the concentration of NO at different locations and is accordingly useful to identify the release of NO [8]. Further, because most stable molecules have all electrons paired, ordinary chemical solvents and matrices do not give rise to EPR spectra, simplifying and significantly improving the noise environment in the measurement.

MTT Colorimetric Cell Assay for Measurement of Cellular Proliferation

To study the cellular proliferation of cancer cell lines, each type of cancer cell line can be incubated with selective NO donor at the concentration that will release a steady optimal concentration. Cell lines can be sampling at each time point for studying cellular proliferation by using MTT reagent. The inhibition rate (RT) of the selective NO donor can be calculated from the absorbance reading, which can be taken using a microtiter plate reader, according to the following formula:

$$\% IR = (1 - OD_{experiment} / OD_{control}) \times 100$$

The results of such a test show when the culture cells have the highest % IR (that is, the time point at which NO will start to inhibit cellular proliferation) and what concentration will cause the maximum of % IR associated with the concentration of cell death. In addition, the results also identify the range of NO concentration and time exposure for which the cells survive.

Microfluidic Cell Assay

Immunoassays is a technique that detects fluorescent signal from the interaction between antigen-antibody. This assay can be utilized to the proteins and molecules' detection. Generally, the assay is performed in 96-well microtiter plates and requires multiple interactions and washing steps, and a long incubation period. However, to perform an assay, large volume of expensive reagents, time consuming and inconvenience are problematic. Therefore, an embodiment of microfluidic technology such as lab-on-a-chip and micro total analysis system has been developed to replace the immunoassay's problems.

Due to in fact that NO has a short half-life, unstable, and we determine the response of iNOS to the concentration of NO during the period of time, NO quantitation measurement is one part of the crucial experiments of this research. NO releasing was measured by observing the converse of NO to nitrite and nitrate in the tissue culture media and this method is also available in the commercial as NO quantitation kit.

Experiment Design

To test the above hypothesis, one can for example pursue the following example specific aims:

Example Aim 1

Determine if level of NO and time of NO exposure regulate the expression of iNOS and apoptosis.

An example working hypotheses is that long term of cells exposing to low concentration of exogenous nitric oxide causes a negative feedback mechanism inducing down regulation of iNOS and promotes tumor progression. As is well known, low NO concentration reduces apoptosis. Thus, low concentration of exogenous NO causes down regulation of iNOS resulting in a reduced ability to produce NO from iNOS. The lower level of NO resulting from down-regulated iNOS will prolong the lifetime of cancer cells. FIG. 42 summarized the relationship between NO exposure concentration and duration (control variables in the experiment) and cell survival time.

Due to in fact that NO levels are needed to regulate in low ranges, the experiment of this study requires in process measurement of NO concentrations during cell culture. Hence, an incubator embodiment provides the convenience, accuracy, and precision of NO concentration monitoring during cell incubating. For instance, NO donor is added to each cell culture well. The sensors beneath the cell culture wells measure the levels of NO. In the meantime, NO donor is added to the cells, when NO levels are dropped out of range of desire (NO levels are detected by the sensor of incubator) to maintain steady state of low concentration of NO. Finally, the cell responses including iNOS expression are able to determine after incubation time and concentration of NO are completed.

In addition, cellular survival can be assessed using a MTT assay described above. It can be predicted that the MTT assay will demonstrate a low value of the inhibition rate (% IR) resulting from a long period of low level of NO exposure.

Therefore, to determine the cell responses to NO concentration such as MTT assay, the fluidic plate of incubator embodiment allows the operation of the reaction occurs while the cells are incubated in the regulated condition. Reactant fluids are moved and mixed in the fluidic plate in regulated environment. In addition, optical embodiment measures absorbance of the final product of the reaction.

Most reports have shown that high concentrations of NO have a destructive effect. In despite of low concentration, it can be predicted that concentrations of NO high enough to cause cell apoptosis will not affect to the negative feedback mechanism of iNOS. Therefore, it can be predicted that the expression of iNOS (for example, as measured by Western Blot or other methods) will not change after the cells are exposed to high level of exogenous NO, however, this same high concentration will give high value of % RT from MTT assay.

Due to in fact that NO levels are needed to regulate in high ranges, the experiment of this study requires in-process measurement of NO concentrations during cell culture. Hence, embodiments of the present application provide the convenience, accuracy, and precision of NO concentration monitoring during cell incubating. For instance, NO donor is added to each cell culture well. The sensors beneath the cell culture wells measure the levels of NO. In the meantime, NO donor is added to the cells, such that NO levels drop out of range of desire (NO levels are detected by the sensors of incubator) to maintain steady state of low concentration of NO. Finally, the cell responses including MTT assay and iNOS expression are able to be determined after incubation time and concentration of NO are completed.

In addition, cellular survival can be assessed using a MTT assay described above. It can be predicted that the MTT assay will demonstrate a low value of the inhibition rate (% IR) resulting from a long period of low level of NO exposure.

Most reports have shown that high concentrations of NO have a destructive effect. In despite of low concentration, it can be predicted that concentrations of NO high enough to cause cell apoptosis will not affect to the negative feedback mechanism of iNOS. Therefore, it can be predicted that the expression of iNOS (for example, as measured by Western Blot or other methods) will not change after the cells are exposed to high level of exogenous NO, however, this same high concentration will give high value of RT from MTT assay.

Example Aim 2

A high level of oxygen in the cellular environment causes a normoxic condition which increases metabolic use of NO. However, low levels of oxygen cause a hypoxic condition that will maintain NO in the cellular environment because hypoxic conditions retards NO degradation. Therefore, it can be predicted that the duration of NO exposure under hypoxia will be longer than time of NO exposure under normoxia. Increasing time of NO exposure will cause down-regulation of iNOS by negative feedback effect. One can observe iNOS expression, for example, using a Western Blot method.

Such work facilitated by various embodiments demonstrates how NO plays role in apoptosis mechanism in cell by presenting the expression of iNOS as negative feedback effect. Consequently, such work facilitated by various embodiments also demonstrates how different of the level of NO and time affect to iNOS expression in cancer cells. Understanding the effect of exogenous NO to apoptosis pathway can directly aid in specifying improved carcinogenic therapy and efficient drug development.

Embodiments of the present application comprise an incubator system with chambers of the fluidic cell culture plates, which consists of an individual gaseous regulator, thus allowing for the study of comparing the cells responses to NO in normoxic and hypoxic condition at the same time.

Figure 42B:
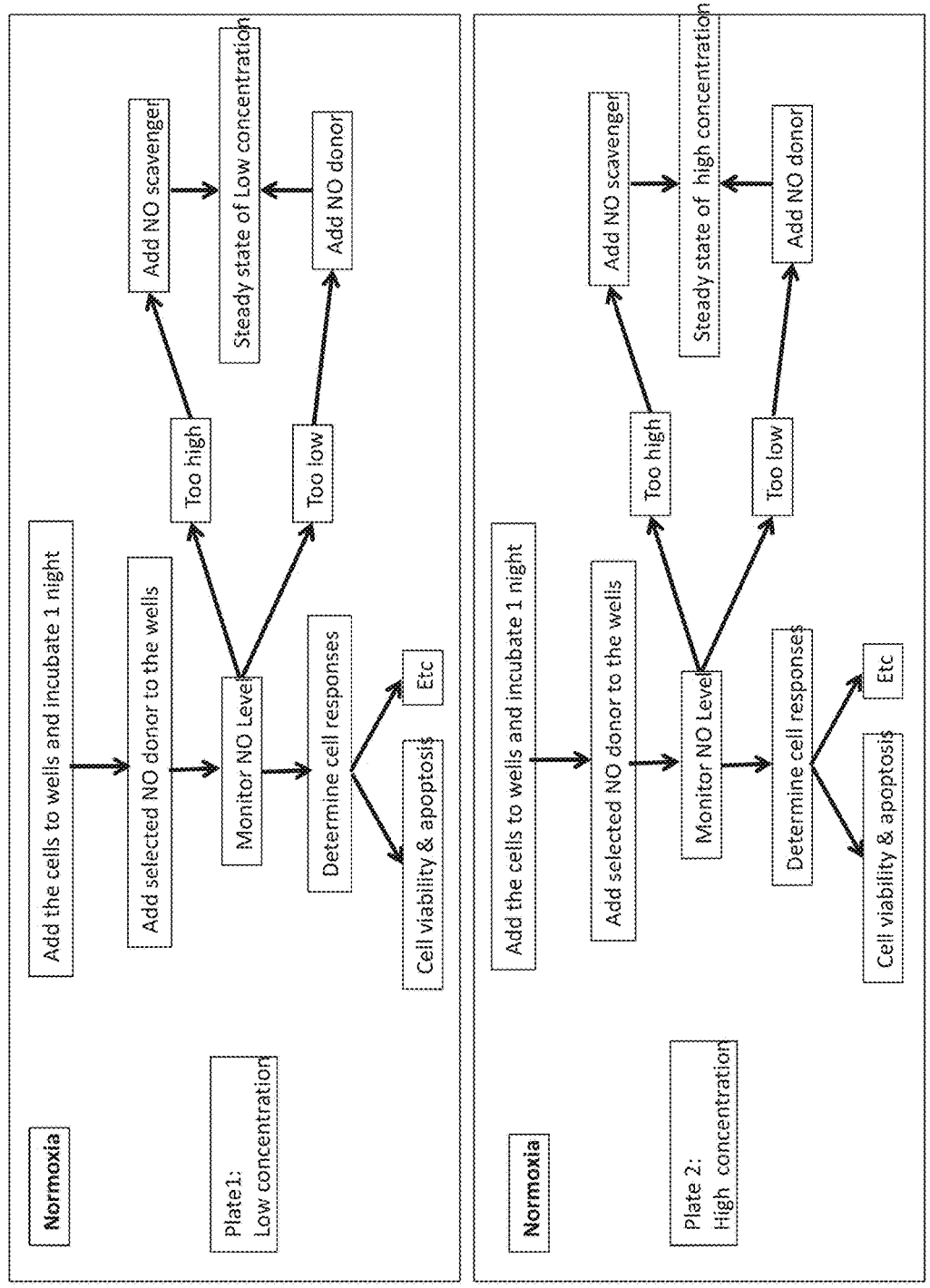
FIG. 42b illustrates a method for determining cell response to normoxic conditions.
Figure 42C:
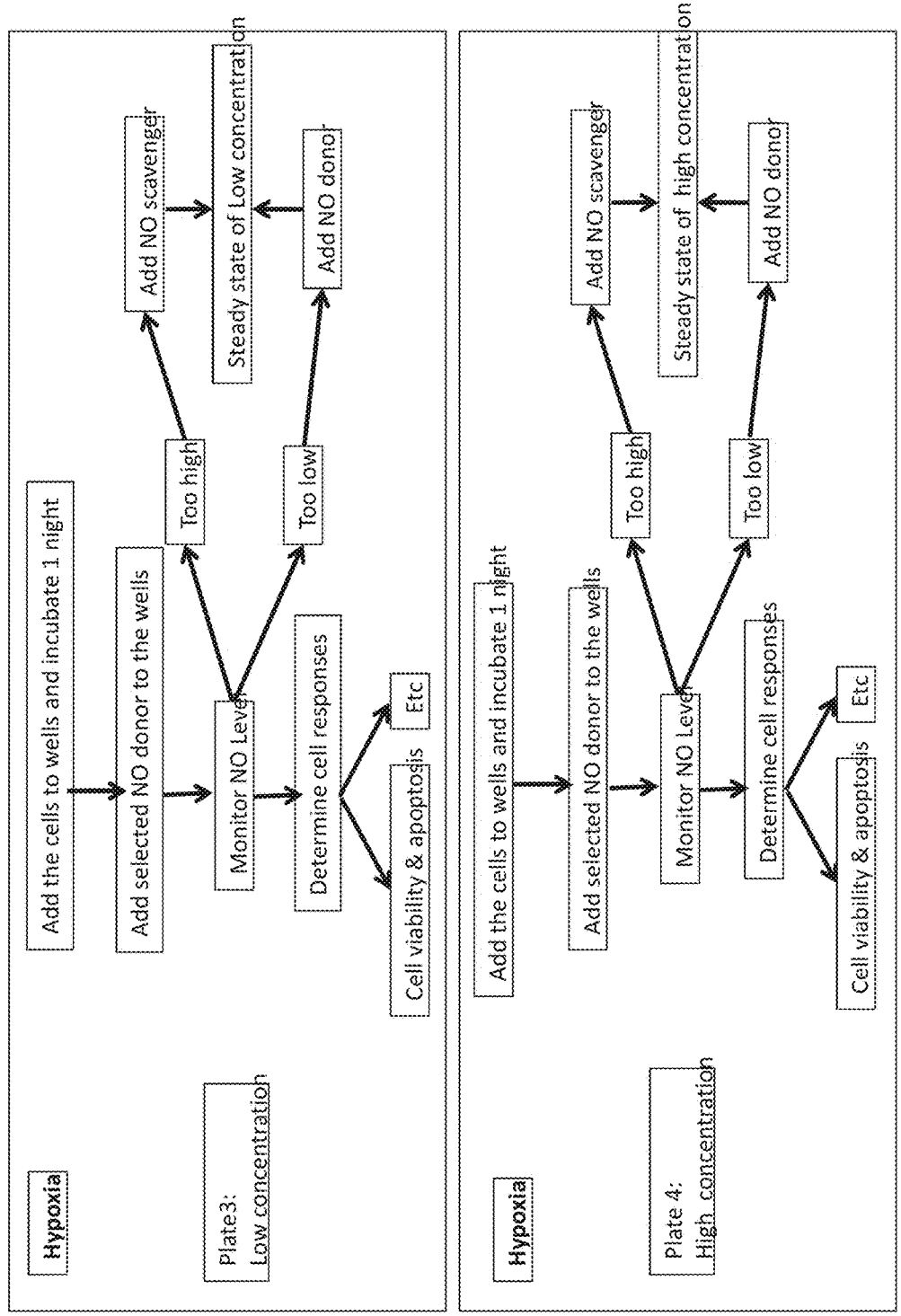
FIG. 42c illustrates a method for determining cell response to hypoxic conditions.

FIGS. 42b-c illustrate methods for comparing cell responses to NO in normoxic (low concentration and/or high concentration) and hypoxic (low concentration and/or high concentration), which can be conducted simultaneously according to some embodiments. As illustrated in FIGS. 42b and 42c, according to some embodiments, incubator system enables the test sample and control sample to be run simultaneously so that the experimenter can observe different response for normoxia and hypoxia.

Figure 42D:
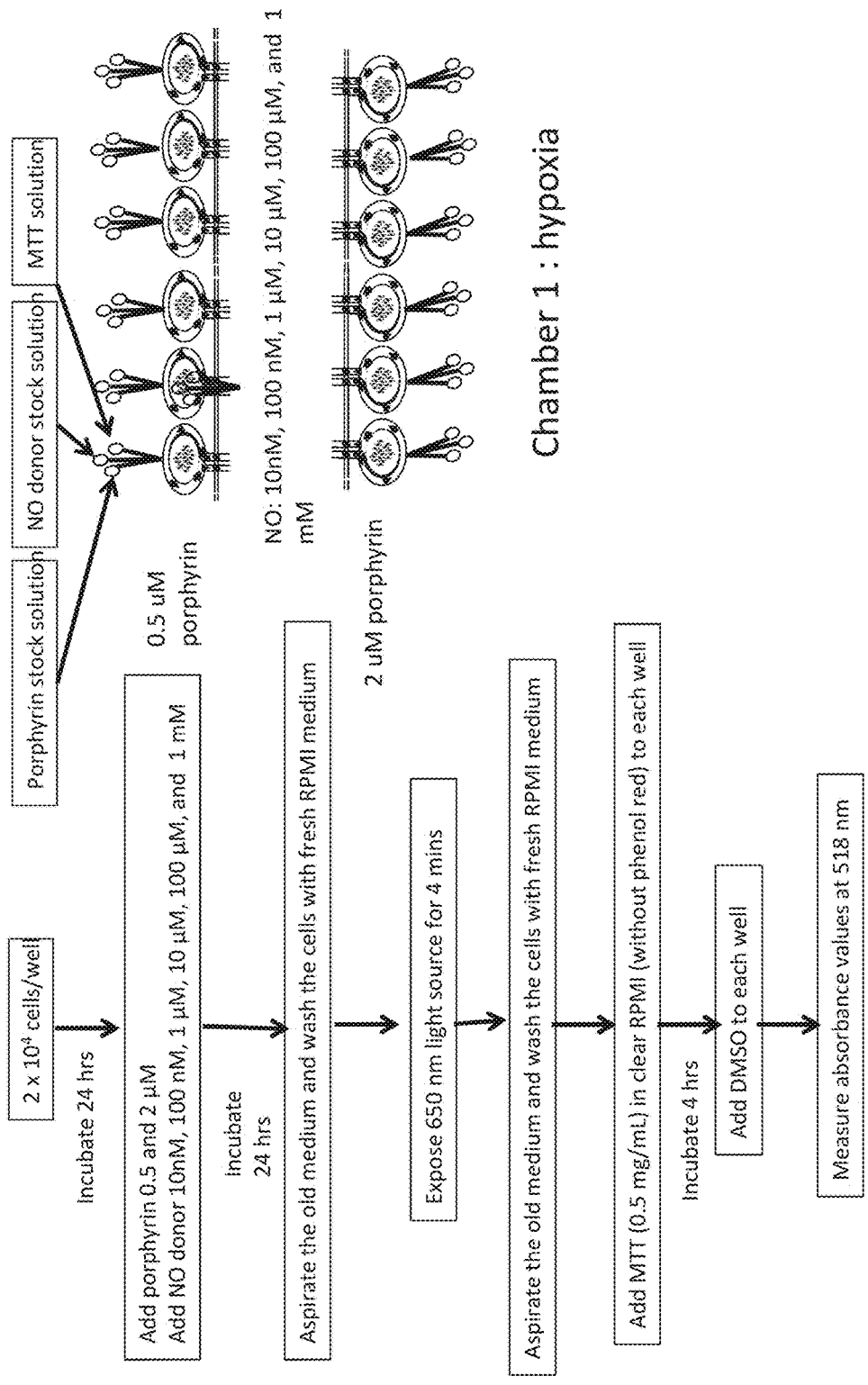
FIG. 42d illustrates a method for determining cell response to hypoxic conditions.

FIG. 42d illustrates a method for comparing cell responses to NO in hypoxic conditions, where a low concentration 0.5 µM porghryin stock solution and a high concentration 2 µM porghryin stock solution are applied, as well as various NO donor concentrations (10 nM, 100 nM, 1 µM, 10 µM, 100 µM, and 1 mM) are applied.

Example Experiment Method Leveraging Various Embodiments

The main reagents are NO donor compounds, such as DEA/NO, DETA/NO, Sper/NO, PABA/NO, SNP, GTN, SNAP, and GSNO. An NO quantitative kit can be used to detect the concentration of NO. Cancer cell lines can be, for example, ovarian cancer cells such as OVCAR-3. The antibodies for such an experiment can employ, for example, iNOS rabbit poly-clonal and IgG 1:1500. As described earlier, and MTT reagent can be used to analyze for cellular proliferation, for example using a microtiter-plate reader.

Ovarian cancer cell lines, OVCAR-3 can be cultured in RPMI medium 1640 (Life technologies, Gland Island, N.Y.) containing 10% FBS (HyClone) and 1% of penicillin-streptomycin. A gas mixture comprising 94% nitrogen, 5% carbon dioxide, and 1% oxygen can be used to create a hypoxia condition; and a gas mixture comprising 95% air with 5% carbon dioxide can be used to create a normoxia condition in humidified atmosphere. The cells can be placed in well plates in Roswell Park Memorial Institute (RPMI) culturing media at a density of 1×104 cell/mL. The medium can be bubbled in advance with 100% $N_2$ before use so as to create a hypoxia condition. The cells can be then be cultured for an adequate duration to attain stability, for example for 48 hours, before use in the experimental procedures made possible by various embodiments.

In general, the cell culture requires mixing and washing steps; thus, the cells are transferred to a fume hood sterilely. The steps of mixing and washing induce a discontinued the growth condition which may affect to the results. For instance, the cells are cultured at 37° C. and hypoxia condition; but, since changing the media that needs to do in the fume hood, the temperature and the gaseous portion are changed. Though, minimizing the time of working outside the incubator may reduce the effect of environmental changes on the cells' response, the environmental breaking of would be a major concern of human errors. In addition, the processes of washing and mixing may disturb a cell attachment; especially, the washing step has an effect on a cell population. Therefore, if even feasible, such experimental procedures requires a skillful operator for reducing this error. However, the various incubator embodiments described earlier readily facilitate all aspects of these experimental procedures.

Various incubator embodiments described earlier provide selective segregated controlled support of cell culture environments and processes, all of which can be controlled in detail by computer algorithm. Various incubator embodiments described earlier provide regulators that control the growth conditions such as temperature, humidity, gaseous portion and sterility as provided by other incubators available in the marketplace. However, various incubator embodiments described earlier additionally provide a plurality of controlled environments, and microfluidic systems allowing fluids such as cell culture media and other materials to be selectively transferred to individually controlled cell culture wells without moving the cell culture microplates from the incubator. As a result, the growth condition does not change during culturing, mixing and washing steps. Also, the mixing and washing processes are controlled by the computer system, and the pressure of flowing solutions does not disturb the cell attachment. In these example ways, as well as many others, the various incubator embodiments described earlier prevent vast numbers of problems and susceptibilities to human errors, and can additionally significantly reduce the amount of training required to perform experiments such as this example as well as far more complex ones.

Measurement of the Concentration of Nitric Oxide for Nitrite Production

Figures 43A, 43B:
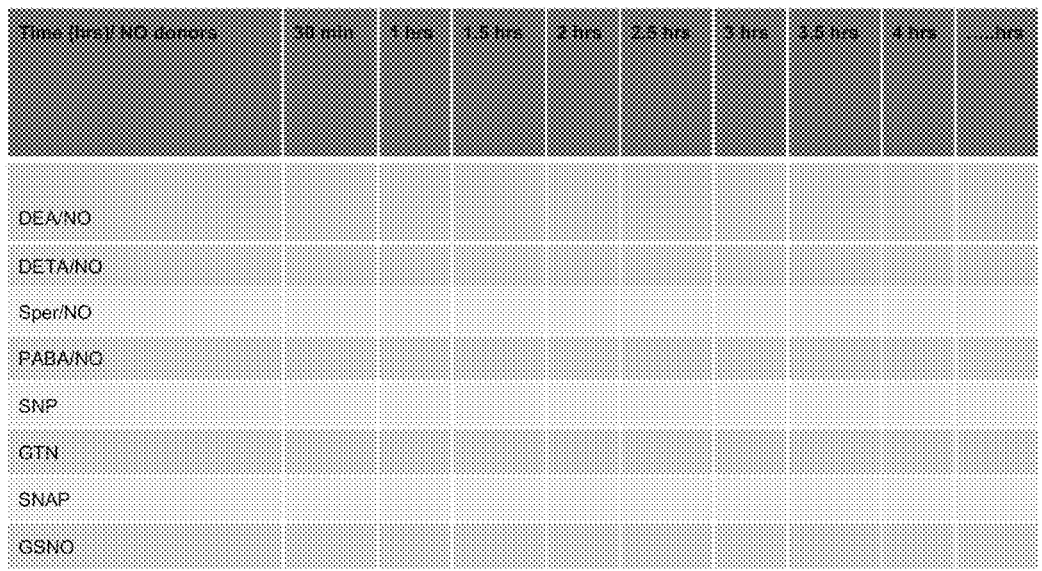
FIG. 43a and FIG. 43b depict representative tables useful in the study of the releasing kinetics in hypoxic and normal conditions of various NO donors.

The releasing kinetic in hypoxic and normal conditions of various NO donors such as DEA/NO, DETA/NO, Sper/NO, PABA/NO, SNP, GTN, SNAP, and GSNO can be studied by using NO quantitative kit as suggested by the tables depicted in FIG. 43a and FIG. 43b. Such example experiment-data collection tables provide for capturing of cell exposure to different concentrations of NO from several kinds of NO donors at each time point in normal condition and hypoxic conditions. After choosing the right NO donor for testing each hypothesis, NO kit will be used for study a half-life and NO production at each concentration in hypoxic and normal environments. The results of this test will answer how much of NO donor and when NO donor will be added to the culture media to get the right total concentration of NO and maintain the steady state NO level, respectively.

Figure 44:
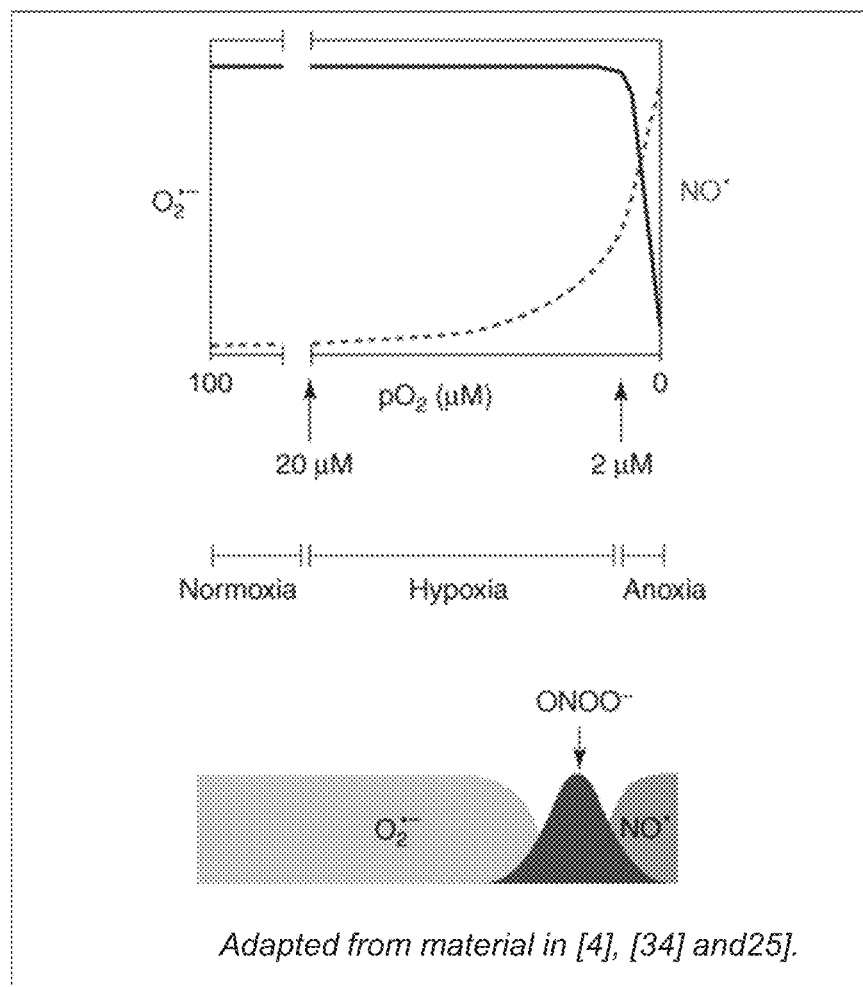
FIG. 44 depicts an example representation of the effect of oxygen concentration ($pO_2$) on $O_2$—NO and ONOO— production.

FIG. 44 depicts an example representation of the effect of oxygen concentration (pO$_2$) on O$_2$—, NO° and ONOO— production [4],[34]. Whereas O$_2$— is the dominant free radical species under normoxia, both ONOO— and O$_2$— are available under hypoxic conditions. Mitochondrially generated NO is expected to be the major mitochondrial free radical species produced under anoxic conditions [25].

The study of Douglas D. Thomas et al. describe the method of NO and O2 quantification. The steady-state concentration of NO was verified by two methods; electrochemically and by a NO gas analyzer [22]. The signals were calibrated by using argon-purged 100 mM phosphate buffer solutions of saturated NO after measuring NO concentration (using 2,2'-azino-bis(ethylbenzothiazoline-6-sulfonic acid at 660 nm, 12,000 M$^{-1}$·cm$^{-1}$) [22]. NO donors were exposed concurrently when culture media was changed to between hypoxia or normoxia conditions. Efimenko et al. observed the responses of cells from exposing the cells to NO and other reactive species under hypoxia and nomoxia condition by using hypoxic incubator. The cell properties were analyzed immediately after cells had been taken off the hypoxia incubator [23]. The NO concentration was determined using standard Griess reagent and the absorbance was measured at 560 nm using a Tecan plate reader. These studies have demonstrated that the concentrations of O2 are involved to a generating of O$_2^-$, NO° and ONOO$^-$. Under nomoxia, the majority of the reactive oxygen species is O$_2^-$, however, under hypoxia, NO$^\square$ and ONOO$^-$ are dominant [25].

Accordingly, an experiment that supports the hypothesis comprises these interacting factors requiring detailed consideration.
1. Concentration of O$_2$; hypoxia and normoxia,
2. Concentrations of NO at steady state and other oxygen reactive species,
3. Types of NO donors,
4. Time of exposure.

Concentration of O$_2$; Hypoxia and Normoxia

To study the cell responses to the gaseous environment, the cells are incubated in normoxia or hypoxia incubators and are taken instantaneously for the cell analysis. For that reason, the errors from cell transferring might occur; even though, a skillful person operates this procedure. In addition, due to a single chamber of incubator, comparing the responses of two samples—one for normoxia and another for hypoxia study-, the experiments are not be able to proceed concomitantly; unless there are more than one incubator.

Various incubator embodiments described earlier provides microfluidic systems within the microplate and monitoring features within the microplate and incubator so that rapid careful transferring of microplates out of the incubator and rapid evaluation or treatment is not required. The cell culture environment can be selectively specified and constantly regulated to a desired condition—normia or hypoxia. Moreover, the incubator consists of multiple chambers of microfluidic plate and every chamber is sealed with a cap. Due to in fact that separate groups or even individual wells of cell culture can be provided a distinct gaseous condition, the samples exposing to normoxia and hypoxia can be experimental studied in a concurrent and immediately comparative fashion. For example, various incubator embodiments described earlier provide explicit support for the study of the cell responses of different kinds of NO donor of both hypoxia and normoxia environment occurs at the same time; in contrast, conventional cell incubators provide explicit barriers if not complete impediments to such study and experiments.

Concentrations of NO at Steady State and Other Oxygen Reactive Species

Figure 45:
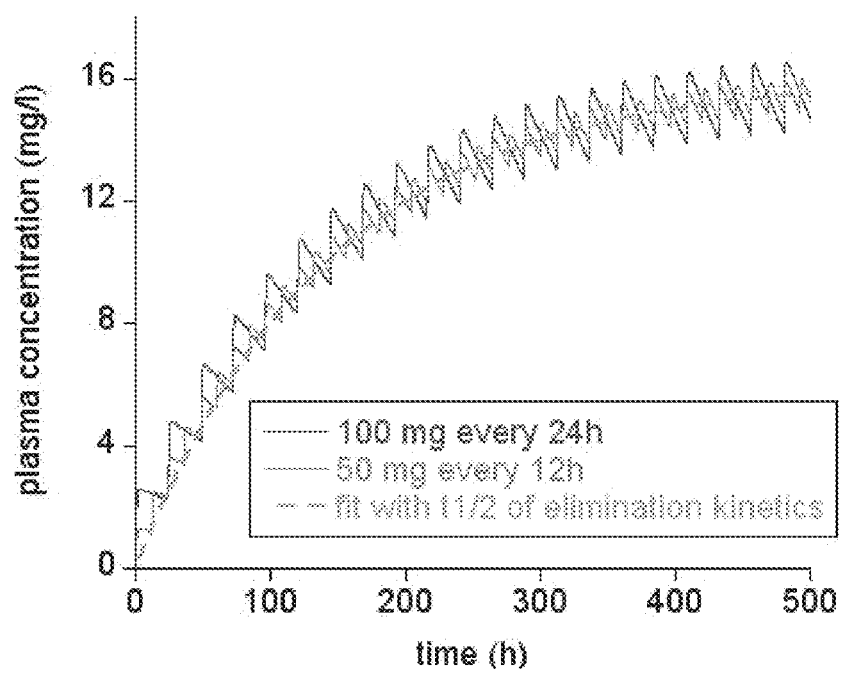
FIG. 45 demonstrates the results of a simulation of Phenobarbital plasma concentration during repeated oral administration for the application schemes indicated. Based on Vd=38 L, CL=0.26 L/h (t½=100 h), F=1.
Figure 46:
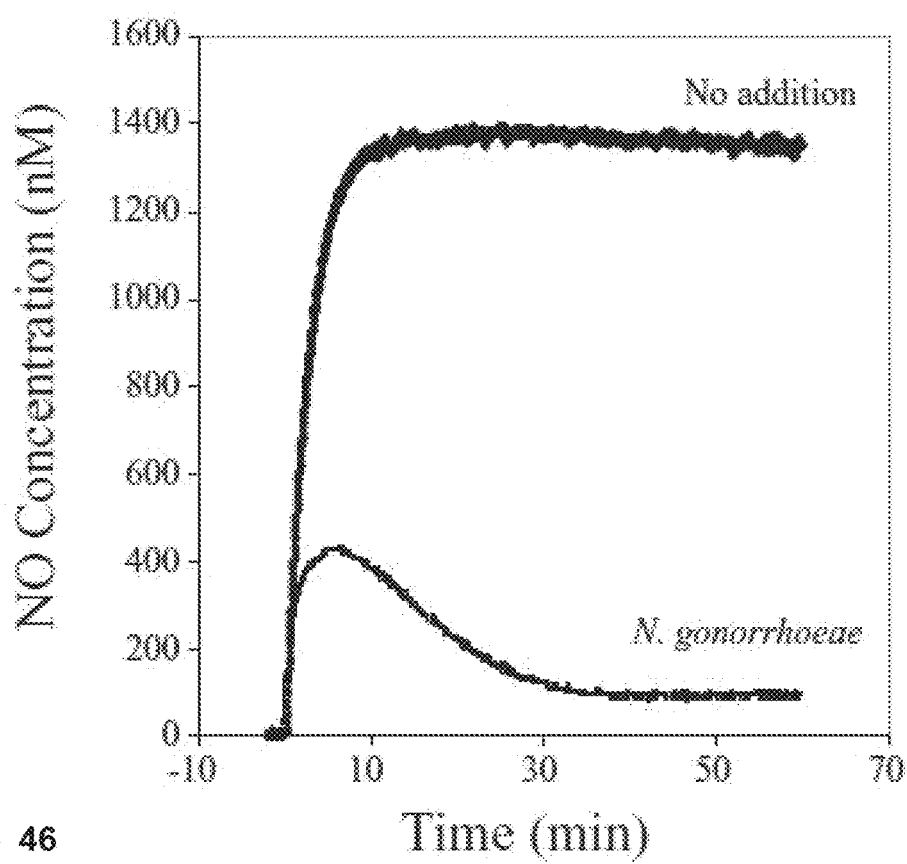
FIG. 46 demonstrates steady state NO concentration showing NO generation from DETA/NO in the absence and presence of anaerobically grown *N. gonorrhoeae*.

In general, maintaining the level of the target drug in blood stream requires the information of a half-life of the drug. The regimen of the drug should be optimal, so it will help the concentration of the drug level is in steady stead. For example, to maintain the concentration of Phenobarbital, having a half-life as 100 hours, in steady state, the oral administration is repeat every 24 hr (for dosage of 100 mg), or every 12 hr (for dosage of 50 mg). FIG. 45, adapted from [20] demonstrates the results of a simulation of Phenobarbital plasma concentration during repeated oral administration for the application schemes indicated. Based on Vd=38 L, CL=0.26 L/h (t½=100 h), F=1. FIG. 46, adapted from [27], demonstrates steady state NO concentration showing NO generation from DETA/NO in the absence and presence of anaerobically grown *N. gonorrhoeae*. Here DETA/NO was added to GCK to a final concentration of 0.3 mM in the absence or presence (OD=0.025) of *N. gonorrhoeae* strain F62 and the NO concentration was monitored as described in the experimental procedures [26]. The study of Garthwaite et al. could control the constant steady state concentration of NO over time by balancing NO release from a NONOate, NO donor, with consumption by a scavenger [28].

To study the effect of concentration of NO and time of cell exposure on the cell responses, monitoring concentration of NO during cell incubation is required. In fact, a half-life of NO depends on NO donors. Also, NO donors have distinct behavioral NO releasing. Furthermore, NO production is relevant to the concentration of surrounding $O_2$ because NO is able to react with $O_2$ and create other oxygen reactive species.

Previous studies have developed NO delivery systems for controlled steady state levels of NO and $O_2$ to imitate biological environments [29, 30]. However, the measuring the concentration of NO during cell culture is not convenient and can induce human errors because the cells needed to be transfer to an NO probe outside the incubator's environmental control, and as a result introduces significant risk of changing the biological environments. In contrast, the various incubator embodiments described earlier provide the convenience of NO determination and minimizes the human errors and risks from changing the biological environment during short-term transferring of cell cultures outside of the incubator environment. Further, various incubator embodiments described earlier include biosensors provided within cell culture wells on microplates plates, making it possible to measure the levels of NO or other oxygen reactive species during cell incubation. Therefore, the incubated cells are continuously determined NO levels or other species in the environmental control incubator, and translocation the cell cultures outside the incubator is not required. In addition, various incubator embodiments described earlier not only permits the control of NO levels, but also can be used to prevent the production of other oxygen reactive species by individual control of gas environments and monitoring by sensors in the cell culture wells.

Types of NO Donors and Exposure Time

The cell responses depends on the concentration of NO and time of cell exposure. Additionally, each kind of NO donor has a different NO releasing behavior. To compare the releasing behavior of each kind of NO donor or the response of cells to NO concentration and time of NO exposure, multiple samples have to be measured concomitantly. Due to in fact that comparing the samples may reduce the environmental errors, various incubator embodiments described earlier support the multiple determinations leveraging multiple units of cell cultures (in the form of multiple separately controlled microplates, or multiple separately groups of wells within a microplate, or even multiple separately individual wells), each containing individual gaseous control and sensors. Therefore, studying the effects of NO exposure parameters on cell responses by varying concentration of NO and time of cell exposure and the type of NO donors is advantageously enabled and supported via various incubator embodiments described earlier.

MTT Assay for Cellular Proliferation

To study the cellular proliferation of cancer cell lines, each type of cancer cell line will be incubated with selective NO donor at the concentration that will release steady optimal concentration. The cell lines will be sampling at each time point as table 2 for studying cellular proliferation by using MTT reagent. The inhibition rate (RT) of the selective NO donor can be calculated from the absorbance reading, which will be taken using a microtiter plate reader as stated by the following formula:

% $IR = (1 - OD_{experiment}/OD_{control}) \times 100$

The results of this test will show when the culture cells will have the highest % IR (what time point that NO will started inhibit cellular proliferation is) and what concentration will cause the maximum of % IR (the concentration of cell death). In addition, the results will present the range of the concentration of NO and time that cells can survive.

The study of Thomas observed the reduction of Alamar blue to its fluorescence product ($\lambda_{Ex/Em}$=550/590 nm) for determining cell proliferation after the cell lines were seed into 96 well microtiter plates and treated in serum-free medium with NO donors for 24 hours [22]. Sato et al. quantified the number of early apoptotic and dead cells using flow cytometry with FITC-conjugated annexin V and propidium iodide (PI). Annexin V- FITC- and PI-strained cells were excited by a 488 nm laser light, and they were collected in the FITC (515-545 nm) and PI (600-620 nm) channels according to emission wavelength.

To determine cell proliferation, the previous findings have used the spectroscopic method, such as UV-Visible (MTT assay), and fluorescence [10, 22]. The methods also contain mixing and washing steps. Consequently, the sample is translocated from an incubator to a fume hood for mixing and washing, and to a spectroscopic microplate reader for measuring an absorbance of an interested final product. As a result, the process of cell proliferative determination contains complex steps. According to the incubator embodiment, the microfluidic system, assigned to design the cell culture plate, is applied to resolve this problem. For example, the microfluidic system allows the MTT solution, from the storage, react with mitochondria reductase and produce the purple crystals. Then the solvent flows from the solvent storage to dissolve the purple crystals to be purple solution, which is observed by the spectroscopic apparatus implanted in the incubator. Therefore, the present application provides the convenience of automatic washing and mixing processes, and allows the reaction occur during incubation period.

Additional Example Embodiments of the Present Application

In one aspect, the present application provides the optimal biological environment such as temperature, gaseous portion, and humidification, wherein the apparatus comprises multiple-chamber controllers. Each chamber provides individual environmental controlled system and individual biosensor detection, and is operated independently. Furthermore, for the microplate comprises replaceable sensing optimizes the cells for attaching and growing.

In certain embodiments, the incubator is able to read the signal from the chemical reaction or the cells responses by electrochemical and optical biosensors within or attached to the microplate.

In certain embodiments, biosensors monitor chemical reactions during cell culture, for instance measuring NO levels during cell incubation.

In certain embodiments, the microfluidic system allows solution or analyte automatically flow through the target location; therefore, the washing and mixing steps are controlled by a computer program.

In certain embodiments, the incubator comprises at least one selective wavelength light source, which is beneficial for a certain experiment, such as the experiment that requires the particular wavelength for a reaction.

In certain embodiments, the incubator comprises multiple chambers of the environmental control—each individual chamber has isolated temperature and gas portion's controls, which allows cells to grow at different condition; and every chamber is able to operate concurrently and independent of each other.

In certain embodiments, the incubator comprises multiple chambers of isolated sensors. The isolated sensors consist a semiconducting material, sensitive to chemical and biological changes. Moreover, the isolated sensors are available for studies of various concentrations, chemical reactions, and cell responses. As a result, every isolated sensor is able to operate concomitantly.

In certain embodiments, the incubator comprises multiple chambers of isolated light sources, which are beneficial for selective wavelength chemical reactions.

In certain embodiments, a plurality of chemical compounds are selected to degrade and release chemical moieties of interest at different wavelengths, allowing a plurality of light sources to initiate or modulate multiple reactions of an experiment at the same time.

In certain embodiments, the isolated sensors each comprise at least one layer of a semiconducting material, wherein the semiconducting material and the selective detection material form at least a portion of each selective sensor, and wherein each selective sensor is configured to provide a variation in an electrical signal responsive to the target agent.

In certain embodiments, each of the isolated selective sensors is connected to an electrical connection. In certain embodiments, the removable medium apparatus further comprises an electrical interface arrangement on the microplate, wherein the electrical interface arrangement is electrically linked to the electrical connections of each of the isolated electrical sensors and is further configured for electrically linking to a host electrical interface within the incubator.

In certain embodiments, at least two of the selective sensors respond to different target agents in the analyte. In certain embodiments, at least two of the selective sensors comprise a different selective detection material from each other, and wherein the different selective detection materials respond to the same target agent in the analyte. In certain embodiments, the selective sensors are of the same nature.

In certain embodiments, at least two of the selective sensors are of different nature. In certain embodiments, the microplate comprises at least one optical sensor and electrochemical sensor.

In certain embodiments, the microplate bottom allows optical propagation through it for a range of wavelengths usable by at least one optical sensing arrangement.

In certain embodiments, the microplate bottom does not allow optical propagation through it for a range of wavelengths employed by at least one optical sensing arrangement.

In certain embodiments, the microplate bottom further comprises an optical filter.

In certain embodiments, the microplate bottom further comprises an optical element. In certain embodiments, the fluid analyte is a raw or processed sample.

In certain embodiments, at least one of the selective sensors is an electrochemical sensors, part of a field effector transistor, or a photodiode. In certain embodiments at least one of the selective sensor materials comprises a molecularly imprinted material.

In certain embodiments, the molecularly imprinted material is a molecularly imprinted polymer. In certain embodiments, at least one of the selective sensor materials comprises an enzyme or a membrane.

In certain embodiments, the removable medium apparatus further comprises a deposit of a reagent.

In certain embodiments, the reagent is a pH buffer material, or cell culture media, or other reagents.

In certain embodiments, the readable medium is attached to the substrate by printing at least one material on the substrate.

In certain embodiments, the readable medium is a separately manufactured label that is adhered to the substrate.

In certain embodiments, the readable medium comprises one or more of: information usable to operate a testing procedure, information usable to perform a statistical analysis, data information, serial number information, information specifying at least one algorithm, parameters used by at least one algorithm, optical encoded data, or magnetic strip.

In certain embodiments, the microplate further comprises a fluidic interface arranged for providing fluid transfer for the receiving arrangement within the base unit.

In certain embodiments, the microplate is attached to a microplate cap so that the resulting arrangement is configured to comprise a fluid channel.

In certain embodiments, the microplate further comprises arrangements associated with at least one optical sensor.

In certain embodiments, the microplate cap further comprises arrangements associated with at least one optical sensor.

In certain embodiments, the microplate provides a fluidic interface arranged for providing fluid transfer for the receiving arrangement within the incubator.

In certain embodiments, the microplate allows optical propagation through it for a range of wavelengths usable by at least one optical sensing arrangement.

In certain embodiments, the microplate cap does not allow optical propagation through it for a range of wavelengths employed by at least one optical sensing arrangement.

In certain embodiments, the microplate cap further comprises an optical filter.

In certain embodiments, the microplate cap further comprises an optical element.

In certain embodiments, fluid routed through microfluidics in the microplate comprises one or more of cells, viruses, suspensions, slurries, emulsions, micelles, or dissolved gases.

In certain embodiments, the incubator of the sensor device comprises at least one computational processor for executing software and a receiving arrangement for receiving, aligning, or physically supporting the removable medium apparatus.

In certain embodiments, the incubator further comprises an electrical interface arrangement for electrically connecting to the removable medium apparatus.

In certain embodiments, the incubator comprises interface electronics for connecting to the electrical interface arrangement for producing sensor measurement signals, each sensor measurement signal comprising a measurement value, the measurement value being one from a range of collection of permitted values.

In certain embodiments, the incubator comprises a medium reader for reading encoded data on a readable medium on the removable medium apparatus. In certain embodiments, the sensor device further comprises a fluidic interface arrangement for connecting to the removable medium apparatus.

In certain embodiments, the microplate comprises a fluid system comprising controllable valves that can be controlled by the computational processor and connected to the fluidic interface arrangement.

Certain embodiments also provide a method of using any one of the sensor devices described herein for detecting a target agent in a fluid analyte, comprising 1) allowing the fluid analyte to be in contact with the selective detection material on the removable medium apparatus; and 2) detecting a detectable signal from the selective sensor on the removable medium apparatus, wherein a variation of the detectable signal prior to and after the contact of the fluid analyte is indicative of the presence of the target analyte.

Also provided by the present application is a method of using any one of the sensor devices described herein for determining the amount of a target agent in a fluid analyte, comprising: 1) allowing the fluid analyte to be in contact with the selective detection material on the removable medium apparatus, and 2) detecting a detectable signal from the selective sensors on the removable medium apparatus, wherein the change of the detectable signal after the contact of the fluid analyte correlates with the amount of the target agent in the fluid analyte.

In certain embodiments, the methods are used for detecting the cell responses and monitor the concentration of the interested substances during cell culture.

In certain embodiments, the methods are used for a biological or chemical assay in the controlled environment of the incubator.

The present application also provides a method of making a microplate for providing replaceable sensing function to an external base unit, the apparatus comprising a plurality of isolated selective sensors on the surface of a substrate, wherein each of the isolated regions the semiconducting material and selective detection material form at least portions of a selective sensor, the method comprising: depositing an array of isolated regions of semiconducting material on the surface of a substrate, the isolated regions comprising at least one layer of semiconducting material; depositing at least one layer of a selective detection material on each of the isolated regions in the array.

In certain embodiments, the method further comprises providing an electrical connection to each of the isolated regions of semiconducting material.

In certain embodiments, the deposition is accomplished by inkjet-printing.

In certain embodiments, the deposition is accomplished by functional printing.

CLOSING

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

The foregoing description, for purpose of explanation, has been described with reference to specific embodiments. However, the illustrative discussions above are not intended to be exhaustive or to limit the present application to the precise forms disclosed. Many modifications and variations are possible in view of the above teachings. The embodiments were chosen and described in order to best explain the principles of the present application and its practical applications, to thereby enable others skilled in the art to best utilize the present application and various embodiments with various modifications as are suited to the particular use contemplated.

While the present application has been described in detail with reference to disclosed embodiments, various modifications within the scope of the present application will be apparent to those of ordinary skill in this technological field. It is to be appreciated that features described with respect to one embodiment typically can be applied to other embodiments.

The present application can be embodied in other specific forms without departing from the spirit or essential characteristics thereof. The present embodiments are therefore to be considered in all respects as illustrative and not restrictive, the scope of the present application being indicated by the appended claims rather than by the foregoing description, and all changes which come within the meaning and range of equivalency of the claims are therefore intended to be embraced therein.

Although exemplary embodiments have been provided in detail, various changes, substitutions and alternations could be made thereto without departing from spirit and scope of the disclosed subject matter as defined by the appended claims. Variations described for the embodiments may be realized in any combination desirable for each particular application. Thus particular limitations and embodiment enhancements described herein, which may have particular advantages to a particular application, need not be used for all applications. Also, not all limitations need be implemented in methods, systems, and apparatuses including one or more concepts described with relation to the provided embodiments. Therefore, the present application properly is to be construed with reference to the claims.

REFERENCES

[1] Konishi, T., Konishi, T., Konishi, T., & Konishi, T. (2006). influence of temperature on growth of *legionella pneumophila* biofilm determined by precise temperature gradient incubator journal of bioscience and bioengineering. *Journal of bioscience and bioengineering*, 101(6), 478-484.

[2] Jennie P., M., & Penelope E., R. (1998). *Introduction to cell and tissue culture: Theory and technique*. (pp. 25-26). New York, N.Y.: Plenum Press.

[3] Lindemann, Corey T.; McGuire, Travis; Sarhadiangardabad, Ara; Siam, Ali; and Tsionis, Elias, "Transportable Incubator for Cell Culture" (2007). Capstone Design Program: Mechanical Engineering. Paper 105. http://hdl.handle.net/2047/d10011778

[4] Shibuki, K. (1990). An electrochemical microprobe for detecting nitric oxide release in brain tissue. *Neurosci. Res.*, 9, 69-76.

[5] Wink, D. A. (1995). A discussion of electrochemical techniques for the detection of nitric oxide. *Methods*, 7, 71-77.

[6] Wink, D. A., Ford, P. C. (1995). Nitric oxide reactions important to biological systems: a survey of some kinetics investigations. *Methods*, 7, 14-20.

[7] Brovkovych, V., Stolarczyk, E., Oman, J., Tomboulian, P., Malinski, T. (1999). Direct electrochemical measurement of nitric oxide in vascular endothelium. *J. Pharm. Biomed. Anal.*, 19, 135-143.

[8] S. Wang, J. F. R. Paton, S. Kasparov. (2006). The challenge of real-time measurements of nitric oxide release in the brain. *Autonomic Neuroscience: Basic and Clinical.*, 126-127, 59-67.

[9] Roychowdhury, S., Luthe, A., Keilhoff, G., Wolf, G., Horn, T. F. (2002). Oxidative stress in glial cultures: detection by DAF-2 fluorescence used as a tool to measure peroxynitrite rather than nitric oxide. *Glia*, 38, 103-114.

[10] Sato, Y., Christ, G. J., Horita, H., Adachi, H., Suzuki, N., Tsukamoto, T. (1999). The effects of alterations in nitric oxide levels in the paraventricular nucleus on copulatory behavior and reflexive erections in male rats. *J. Urol.*, 162, 2182-2185.

[11] Tarn, M. F., Pamme, N. (2011). Microfluidic platforms for performing surface-based clinical assays. *Expert Rev. Mol. Diagn.*, 11(7), 711-720.

[12] Fulstone, R., Coughlan C. M., Wiktorowicz J. E., Lengsfeld, C. S. (2012). A microliter incubator array for understanding culture condition selectivity. *Advances in Bioscience and Biotechnology*, 3, 87-91.

[13] Jeanette, Fenwick, Stephen, Harbottle, Mary, Herbert, and Jame, Walker. 2010. Laboratory apparatus with incubator. US. Patent 20100291664, Filed Oct. 27, 2006, and Issued Jun. 20, 2010.

[14] Goffe, Randal A. 1999. Cell culture incubator. U.S. Pat. No. 5,958,763, filed Aug. 4, 1998, and issued Sep. 28, 1999.

[15] Randy Yerden. 2003. Cell culture incubator with Dynamic oxygen control. U.S. Pat. No. 0,092,178, filled Nov. 15, 2001, and issued May 15, 2003.

[16] James, Anderson, Amy, Bishop. 2011. Apparatus and method for incubating cell culture. U.S. Pat. No. 7,906,324, filed May 12, 2006, and issued Mar. 15, 2011.

[17] Mitsuhiro, OURA, Reruo, Okano, Tatsuya, Shimizu, Hirotsugu, Kubo, Katsuyoshi, Suzuki, Sunao, Takeda. 2012. Cell incubator and incubation condition monitoring system. U.S. Pat. No. 0,214,225, filed Feb. 19, 2012, and issued Aug. 23, 2012.

[18] Mitsuhiro, OURA, Reruo, Okano, Tatsuya, Shimizu, Hirotsugu, Kubo, Katsuyoshi, Suzuki, Sunao, Takeda. 2012. Cell culture apparatus. U.S. Pat. No. 0,252,110, filed Mar. 28, 2012, and issued Oct. 24, 2012.

[19] Butts, Charles G. 2006. Ultraviolet sterilization of CO2 cell-culture incubator internal environments. U.S. Pat. No. 6,297,047, filed Aug. 25, 1999, and issued Oct. 2, 2001

[20] Buclin, T., Nicod, M., Kellenberger, S., Martin, K., Martin, K., & Martin, K. (2009). *"drug administration of a fixed dose at a regular time interval, through a given route."*. Retrieved from http://sepia.unil.ch/pharmacology/index.php?id=70

[21] Cardinale, J. A., Clark V. L. (2005). Determinants of nitric oxide steady-state levels during anaerobic respiration by *Neisseria gonorrhoeae*. *Molecular Microbiology*, 58 (1), 177-188.

[22] Thomas, D. D., Espey M. G., Ridnour, L. A., Hofseth L. J., Mancardi, D., Harris, C. C., Wink D. A. (2004). Hypoxic inducible factor 1, extracellular signal-regulated kinase, and p53 are regulated by distinct threshold concentrations of nitric oxide. *PNAS*, 101 (24), 8894-8899.

[23] Efimenko, A., Starostina, E., Kalinina N., Efimenko, S. A., et al. (2011). Angiogenic properties of aged adipose derived mesenchymal stem cells after hypoxic conditioning. *Journal of Translational Medicine*, 9 (10).

[24] Sato, T., Oku, H., Tsuruma, K., Katsumura, K., Shimazawa, M., Hara, H., Sugiyama, T., IkedaT. (2010). Effect of Hypoxia on Susceptibility of RGC-5 Cells to Nitric Oxide. *Investigative Ophthalmology & Visual Science*, 51 (5), 2575-2586.

[25] Poyton, R. O., Ball, K. A., Castello, P. R. (2009). Mitochondrial generation of free radicals and hypoxic signaling. *Trends in Endocrinology and Metabolism*, 20 (7), 332-340.

[26] Cardinale, J. A., Clark, V. L. (2005). Determinants of nitric oxide steady-state levels during anaerobic respiration by *Neisseria gonorrhoeae*. *Molecular Microbiology*, 58 (1), 177-188.

[27] Dendroulakis, V., Russell, B. S., Elmquist, C. E., Trudel, L. J., Wogan, G. N., Deen, W. M., Dedon, P. C. (2012). A system for exposing molecules and cells to biologically relevant and accurately controlled steady-stateconcentrations of nitric oxide and oxygen, *Nitric Oxide*, 27(3), 161-8.

[28] Griffiths, C., Wykes, V., Bellamy, T. C., Garthwaite, J. (2003). A New and Simple Method for Delivering Clamped Nitric Oxide Concentrations in the Physiological Range: Application to Activation of Guanylyl Cyclase-Coupled Nitric Oxide Receptors. *Mol. Pharm.*, 64, 1349.

[29] Lewis, R. S., Deen, W. M. (1996) Stirred reactor with continuous nitric oxide sampling for use in kinetic studies. *Methods Enzymol.* 268, 247-259.

[30] Wang, C., Deen, W. M. (2003). Nitric oxide delivery system for cell culture studied. *Ann. Biomed. Eng.*, 31, 65-79.

[31] Honda, A., Adams, S. R., Sawyer, C. L., Lev-Ram, V., Tsien, Dostmann, W. R. (2001). Spatiotemporal dynamics of guanosine 3',5'-cyclic monophosphate revealed by a genetically encoded, fluorescent indicator *Proc Natl Acad Sci USA*, 98, 2437-2442.

What is claimed is:

1. A environment-localizing cap system for use with a sensor-provisioned microplate for processing samples, the system comprising:

a plurality of wells arranged into an array, forming an array of wells, each of the wells including a chamber and further including at least one associated electrical sensor;

a plurality of environment-localizing caps including plurality of seals arranged into an array, forming an array of environment-localizing caps, the array of environment-localizing caps arranged to align with the array of wells so that each of the caps separately cover a top surface of a different associated well in the array of wells and separately seals the top surface of the different associated well in the array of wells, wherein each cap directly seals the entire top surface of the different associated well, wherein each seal overlaps a portion of a top of the microplate, a plurality of electrical conductors in the microplate for interconnecting with the electrical sensors; and a plurality of fluidic structures coupled to the plurality of environment-localizing caps, a first subset of the plurality of fluidic structures arranged to carry at least fluids incoming to at least a first well through the environment-localizing cap associated with the at least the first well, and a second subset of the plurality of fluidic structures arranged to carry at least fluids outgoing from at least a second well through the environment-localizing cap associated with the at least the second well, wherein the plurality of environment-localizing caps are linked by fluidic connections to the plurality of fluidic structures within the plurality of environment-localizing caps, wherein the array of environment-localizing caps fitted with the array of wells create a separate controlled fluidic and gas environment in each well.

2. The system of claim 1, the microplate wells interconnected with fluidics and gas exchange structures within the microplate to interface with the plurality of wells and reagent deposits.

3. The microplate of claim 2, wherein the first or second subset of the plurality of fluidic structures couples to a bottom side of the one of the plurality of wells.

4. The system of claim 1, wherein the array of environment-localizing caps further comprises an electrical interface arranged to electrically connect with the electrical conductors in the microplate.

5. The system of claim 1, wherein at least one of the environment-localizing caps further comprise individually-controlled arrangements for providing well-specific optical stimulation.

6. The system of claim 1, wherein at least one of the environment-localizing caps further comprise individually-controlled arrangements for dispensing a well-specific quantity dispensing of oxygen.

7. The system of claim 1, wherein at least one of the environment-localizing caps further comprise individually-controlled arrangements for dispensing a well-specific quantity of a pharmaceutical agent.

8. The system of claim 1, wherein at least one of the environment-localizing caps further comprise individually-controlled arrangements for dispensing a well-specific quantity of an infectious agent.

9. The system of claim 1, wherein at least one of the environment-localizing caps further comprise individually-controlled arrangements for dispensing a well-specific quantity of a toxin.

10. The system of claim 1, wherein at least one of the environment-localizing caps further comprise individually-controlled arrangements for dispensing a well-specific quantity of a liquid.

11. The system of claim 1, wherein at least one of the environment-localizing caps further comprise individually-controlled arrangements for dispensing a well-specific quantity of a gas.

12. The system of claim 1, wherein at least one of the wells in the microplate further comprise arrangements for individually-controlling the wall temperature of the well.

13. A cell incubation system, comprising:
an incubator compartment for receiving a microplate for processing samples, the microplate comprising:
a plurality of wells, each of the plurality of wells including a collection chamber and further including at least one associated electrical sensor;
a plurality of environment-localizing caps including a plurality of seals arranged into an array, forming an array of environment-localizing caps, the array of environment-localizing caps arranged to align with the array of wells so that each of the caps separately covers a top surface of a different associated well in the array of wells and separately seal the entire top surface of the different associated well in the array of wells, wherein each seal overlaps a portion of a top of the microplate, wherein each cap directly seals the top surface of the different associated well, a plurality of electrical conductors in the microplate for interconnecting with the electrical sensors; and
a plurality of fluidic structures coupled to the plurality of environment-localizing caps, a first subset of the plurality of fluidic structures arranged to carry at least fluids incoming to at least a first well through the environment-localizing cap associated with the at least the first well, and a second subset of the plurality of fluidic structures arranged to carry at least fluids outgoing from at least a second well through the environment-localizing cap associated with the at least the second well, wherein the plurality of environment-localizing caps are linked by fluidic connections to the plurality of fluidic structures within the plurality of environment-localizing caps.

14. The cell incubation system of claim 13, the microplate wells interconnected with fluidics and gas exchange structures within the microplate to interface with the plurality of wells and reagent deposits.

15. The cell incubation system of claim 14, wherein the first or second subset of the plurality of fluidic structures couples to a bottom side of the one of the plurality of wells.

16. The cell incubation system of claim 13, wherein the array of environment-localizing caps further comprises an electrical interface arranged to electrically connect with the electrical conductors in the microplate.

17. The cell incubation system of claim 13, wherein at least one of the environment-localizing caps further comprise individually-controlled arrangements for providing well-specific optical stimulation.

18. The cell incubation system of claim 13, wherein at least one of the environment-localizing caps further comprise individually-controlled arrangements for dispensing a well-specific quantity dispensing of oxygen.

19. The cell incubation system of claim 13, wherein at least one of the environment-localizing caps further comprise individually-controlled arrangements for dispensing a well-specific quantity of a pharmaceutical agent.

20. The cell incubation system of claim 13, wherein at least one of the environment-localizing caps further comprise individually-controlled arrangements for dispensing a well-specific quantity of an infectious agent.

21. The cell incubation system of claim 13, wherein at least one of the environment-localizing caps further comprise individually-controlled arrangements for dispensing a well-specific quantity of a toxin.

22. The cell incubation system of claim 13, wherein at least one of the wells in the microplate further comprise arrangements for individually-controlling the wall temperature of the well.

23. The cell incubation system of claim 13, wherein at least one of the environment-localizing caps further comprise individually-controlled arrangements for dispensing a well-specific quantity of a liquid.

24. The cell incubation system of claim 13, wherein at least one of the environment-localizing caps further comprise individually-controlled arrangements for dispensing a well-specific quantity of a gas.

* * * * *